(12) United States Patent
Or et al.

(10) Patent No.: US 8,609,648 B2
(45) Date of Patent: Dec. 17, 2013

(54) HEPATITIS C VIRUS INHIBITORS

(75) Inventors: Yat Sun Or, Watertown, MA (US); Lu Ying, Shanghai (CN); Xiaowen Peng, Auburndale, MA (US); Datong Tang, Newton, MA (US); Ce Wang, Waltham, MA (US); Yao-Ling Qiu, Andover, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 444 days.

(21) Appl. No.: 12/816,171

(22) Filed: Jun. 15, 2010

(65) Prior Publication Data

US 2011/0008288 A1   Jan. 13, 2011

Related U.S. Application Data

(60) Provisional application No. 61/222,586, filed on Jul. 2, 2009.

(51) Int. Cl.
| | | |
|---|---|---|
| A01N 43/42 | (2006.01) |
| A01N 43/00 | (2006.01) |
| A61K 31/00 | (2006.01) |
| A61K 31/535 | (2006.01) |
| C07D 513/02 | (2006.01) |
| C07D 515/02 | (2006.01) |
| C07D 267/02 | (2006.01) |
| C07D 281/02 | (2006.01) |
| C07D 291/08 | (2006.01) |
| C07D 413/00 | (2006.01) |

(52) U.S. Cl.
USPC .............. 514/210.18; 514/299; 514/233.2; 514/253.04; 514/314; 546/114; 546/116; 544/127; 544/328; 540/490; 540/491

(58) Field of Classification Search
USPC .......... 546/114, 116; 544/127, 328; 514/299, 514/233.2, 253.04, 210.18, 314; 540/490, 540/491
See application file for complete search history.

(56) References Cited

U.S. PATENT DOCUMENTS

| | | | |
|---|---|---|---|
| 5,935,982 A | 8/1999 | Dykstra et al. | |
| 7,141,574 B2 | 11/2006 | Beaulieu et al. | |
| 8,088,368 B2 * | 1/2012 | Guo et al. | 424/85.4 |
| 2006/0003942 A1 | 1/2006 | Tung et al. | |
| 2006/0058317 A1 | 3/2006 | Gravestock et al. | |
| 2007/0299068 A1 | 12/2007 | Karp et al. | |
| 2009/0047247 A1 | 2/2009 | Qiu et al. | |
| 2009/0202478 A1 | 8/2009 | Bachand et al. | |
| 2009/0202483 A1 | 8/2009 | Bachand et al. | |
| 2010/0221214 A1 | 9/2010 | Or et al. | |
| 2010/0221215 A1 | 9/2010 | Qiu et al. | |
| 2010/0221216 A1 | 9/2010 | Or et al. | |
| 2010/0226882 A1 | 9/2010 | Or et al. | |
| 2010/0226883 A1 | 9/2010 | Qiu et al. | |
| 2010/0233120 A1 | 9/2010 | Bachand et al. | |
| 2010/0233122 A1 | 9/2010 | Qiu et al. | |
| 2010/0260708 A1 | 10/2010 | Belema et al. | |
| 2010/0260715 A1 | 10/2010 | Or et al. | |
| 2010/0266543 A1 | 10/2010 | Qiu et al. | |
| 2010/0310512 A1 | 12/2010 | Guo et al. | |

FOREIGN PATENT DOCUMENTS

| | | |
|---|---|---|
| WO | 2006133326 A1 | 12/2006 |
| WO | 2008021927 A2 | 2/2008 |
| WO | 2008021928 A2 | 2/2008 |
| WO | 2008021936 A2 | 2/2008 |
| WO | 2008144380 A1 | 11/2008 |
| WO | 2009020825 A1 | 2/2009 |
| WO | 2009020828 A1 | 2/2009 |
| WO | 2009102318 A1 | 8/2009 |
| WO | 2009102325 A1 | 8/2009 |
| WO | 2009102568 A1 | 8/2009 |
| WO | 2009102633 A1 | 8/2009 |
| WO | 2009102694 A1 | 8/2009 |
| WO | 2010017401 A1 | 2/2010 |
| WO | 2010039793 A1 | 4/2010 |
| WO | 2010065668 A1 | 6/2010 |
| WO | 2010065674 A1 | 6/2010 |
| WO | 2010065681 A1 | 6/2010 |
| WO | 2010096302 A1 | 8/2010 |
| WO | 2010096777 A1 | 8/2010 |
| WO | 2010111483 A1 | 9/2010 |
| WO | 2010111534 A1 | 9/2010 |

(Continued)

OTHER PUBLICATIONS

U.S. Appl. No. 12/816,148, Or, et al.
U.S. Appl. No. 12/851,350, Or, et al.
U.S. Appl. No. 12/879,025, Qiu, et al.
U.S. Appl. No. 12/879,026, Or, et al.

(Continued)

*Primary Examiner* — Niloofar Rahmani
(74) *Attorney, Agent, or Firm* — Roy P. Issac; Carolyn S. Elmore; Elmore Patent Law Group, P.C.

(57) ABSTRACT

The present invention discloses compounds of Formula (I), or pharmaceutically acceptable salts, esters, or prodrugs thereof:

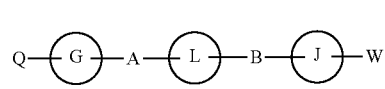

which inhibit RNA-containing virus, particularly the hepatitis C virus (HCV). Consequently, the compounds of the present invention interfere with the life cycle of the hepatitis C virus and are also useful as antiviral agents. The present invention further relates to pharmaceutical compositions comprising the aforementioned compounds for administration to a subject suffering from HCV infection. The invention also relates to methods of treating an HCV infection in a subject by administering a pharmaceutical composition comprising the compounds of the present invention.

8 Claims, No Drawings

(56) References Cited

FOREIGN PATENT DOCUMENTS

| WO | 2010111673 A1 | 9/2010 |
| WO | 2010117635 A1 | 10/2010 |
| WO | 2010117704 A1 | 10/2010 |
| WO | 2010132538 A1 | 11/2010 |
| WO | 2010138368 A1 | 12/2010 |
| WO | 2010138488 A1 | 12/2010 |
| WO | 2010138790 A1 | 12/2010 |
| WO | 2010138791 A1 | 12/2010 |

OTHER PUBLICATIONS

U.S. Appl. No. 12/879,027, Qiu, et al.
U.S. Appl. No. 12/879,028, Or, et al.
U.S. Appl. No. 12/879,029, Qiu, et al.
U.S. Appl. No. 12/879,031, Or, et al.
Bressanelli, et al., "Crystal Structure of the RNA-dependent RNA Polymerase of Hepatitis C Virus," PNAS, 96 (23):13034-13039, 1999.
International Search Report for PCT/US10/38699, dated Aug. 13, 2010.

\* cited by examiner

HEPATITIS C VIRUS INHIBITORS

RELATED APPLICATION

This application claims the benefit of U.S. Provisional Application No. 61/222,586 filed Jul. 2, 2009. The entire teachings of the above application are incorporated herein by reference.

TECHNICAL FIELD

The present invention relates to novel antiviral agents. More specifically, the present invention relates to compounds which can inhibit the function of the NS5A protein encoded by Hepatitis C Virus (HCV), compositions comprising such compounds, methods for inhibiting HCV viral replication, and methods for treating or preventing HCV infection, and processes for making the compounds.

BACKGROUND OF THE INVENTION

Infection with HCV is a major cause of human liver disease throughout the world. In the US, an estimated 4.5 million Americans are chronically infected with HCV. Although only 30% of acute infections are symptomatic, greater than 85% of infected individuals develop chronic, persistent infection. Treatment costs for HCV infection have been estimated at $5.46 billion for the US in 1997. Worldwide over 200 million people are estimated to be infected chronically. HCV infection is responsible for 40-60% of all chronic liver disease and 30% of all liver transplants. Chronic HCV infection accounts for 30% of all cirrhosis, end-stage liver disease, and liver cancer in the U.S. The CDC estimates that the number of deaths due to HCV will minimally increase to 38,000/year by the year 2010.

Due to the high degree of variability in the viral surface antigens, existence of multiple viral genotypes, and demonstrated specificity of immunity, the development of a successful vaccine in the near future is unlikely. Alpha-interferon (alone or in combination with ribavirin) has been widely used since its approval for treatment of chronic HCV infection. However, adverse side effects are commonly associated with this treatment: flu-like symptoms, leukopenia, thrombocytopenia, depression from interferon, as well as anemia induced by ribavirin (Lindsay, K. L. (1997) Hepatology 26 (suppl 1): 71S-77S). This therapy remains less effective against infections caused by HCV genotype 1 (which constitutes ~75% of all HCV infections in the developed markets) compared to infections caused by the other 5 major HCV genotypes. Unfortunately, only ~50-80% of the patients respond to this treatment (measured by a reduction in serum HCV RNA levels and normalization of liver enzymes) and, of responders, 50-70% relapse within 6 months of cessation of treatment. Recently, with the introduction of pegylated interferon (Peg-IFN), both initial and sustained response rates have improved substantially, and combination treatment of Peg-IFN with ribavirin constitutes the gold standard for therapy. However, the side effects associated with combination therapy and the impaired response in patients with genotype 1 present opportunities for improvement in the management of this disease.

First identified by molecular cloning in 1989 (Choo, Q-L et al (1989) Science 244:359-362), HCV is now widely accepted as the most common causative agent of post-transfusion non-A, non-B hepatitis (NANBH) (Kuo, G et al (1989) Science 244:362-364). Due to its genome structure and sequence homology, this virus was assigned as a new genus in the Flaviviridae family. Like the other members of the Flaviviridae, such as flaviviruses (e.g. yellow fever virus and Dengue virus types 1-4) and pestiviruses (e.g. bovine viral diarrhea virus, border disease virus, and classic swine fever virus) (Choo, Q-L et al (1989) Science 244:359-362; Miller, R. H. and R. H. Purcell (1990) Proc. Natl. Acad. Sci. USA 87:2057-2061), HCV is an enveloped virus containing a single strand RNA molecule of positive polarity. The HCV genome is approximately 9.6 kilobases (kb) with a long, highly conserved, noncapped 5' nontranslated region (NTR) of approximately 340 bases which functions as an internal ribosome entry site (IRES) (Wang C Y et al 'An RNA pseudoknot is an essential structural element of the internal ribosome entry site located within the hepatitis C virus 5' noncoding region' RNA—A Publication of the RNA Society. 1(5): 526-537, 1995 July). This element is followed by a region which encodes a single long open reading frame (ORF) encoding a polypeptide of ~3000 amino acids comprising both the structural and nonstructural viral proteins.

Upon entry into the cytoplasm of the cell, this RNA is directly translated into a polypeptide of ~3000 amino acids comprising both the structural and nonstructural viral proteins. This large polypeptide is subsequently processed into the individual structural and nonstructural proteins by a combination of host and virally-encoded proteinases (Rice, C. M. (1996) in B. N. Fields, D. M. Knipe and P. M. Howley (eds) Virology $2^{nd}$ Edition, p 931-960; Raven Press, N.Y.). There are three structural proteins, C, E1 and E2. The P7 protein is of unknown function and is comprised of a highly variable sequence. There are several non-structural proteins. NS2 is a zinc-dependent metalloproteinase that functions in conjunction with a portion of the NS3 protein. NS3 incorporates two catalytic functions (separate from its association with NS2): a serine protease at the N-terminal end, which requires NS4A as a cofactor, and an ATP-ase-dependent helicase function at the carboxyl terminus. NS4A is a tightly associated but non-covalent cofactor of the serine protease. NS5A is a membrane-anchored phosphoprotein that is observed in basally phosphorylated (56 kDa) and hyperphosphorylated (58 kDa) forms. While its function has not fully been elucidated, NS5A is believed to be important in viral replication. The NS5B protein (591 amino acids, 65 kDa) of HCV (Behrens, S. E. et al (1996) *EMBO J.* 151 2-22) encodes an RNA-dependent RNA polymerase (RdRp) activity and contains canonical motifs present in other RNA viral polymerases. The NS5B protein is fairly well conserved both intra-typically (~95-98% amino acid (aa) identity across 1b isolates) and inter-typically (~85% aa identity between genotype 1a and 1b isolates). The essentiality of the HCV NS5B RdRp activity for the generation of infectious progeny virions has been formally proven in chimpanzees (A. A. Kolykhalov et al. (2000) *Journal of Virology*, 74(4): 2046-2051). Thus, inhibition of NS5B RdRp activity (inhibition of RNA replication) is predicted to be useful to treat HCV infection.

Following the termination codon at the end of the long ORF, there is a 3' NTR which roughly consists of three regions: an ~40 base region which is poorly conserved among various genotypes, a variable length poly(U)/polypyrimidine tract, and a highly conserved 98 base element also called the "3' X-tail" (Kolykhalov, A. et al (1996) J. Virology 70:3363-3371; Tanaka, T. et al (1995) Biochem Biophys. Res. Commun. 215744-749; Tanaka, T. et al (1996) J. Virology 70:3307-3312; Yamada, N. et al (1996) Virology 223:255-261). The 3' NTR is predicted to form a stable secondary structure which is essential for HCV growth in chimps and is believed to function in the initiation and regulation of viral RNA replication.

Compounds useful for treating HCV-infected patients are desired which selectively inhibit HCV viral replication. In particular, compounds which are effective to inhibit the function of the NS5A protein are desired. The HCV NS5A protein is described, for example, in Tan, S.-L., Katzel, M. G. *Virology* 2001, 284, 1; and in Rice, C. M. *Nature* 2005, 435, 374.

Based on the foregoing, there exists a significant need to identify compounds with the ability to inhibit HCV. A general strategy for the development of antiviral agents is to inactivate virally encoded proteins, including NS5A, that are essential for the replication of the virus. The relevant patent disclosures describing the synthesis of HCV NS5A inhibitors are: US 2009/0202478; US 2009/0202483; WO 2009/020828; WO 2009/020825; WO 2009/102318; WO 2009/102325; WO 2009/102694; WO 2008/144380; WO 2008/021927; WO 2008/021928; WO 2008/021936; WO 2006/133326; WO 2004/014852; WO 2008/070447; WO 2009/034390; WO 2006/079833; WO 2007/031791; WO 2007/070556; WO 2007/070600; WO 2008/064218; WO 2008/154601; WO 2007/082554; and WO 2008/048589; the contents of each of which are expressly incorporated by reference herein.

SUMMARY OF THE INVENTION

The present invention relates to novel antiviral compounds represented herein below, pharmaceutical compositions comprising such compounds, and methods for the treatment or prophylaxis of viral (particularly HCV) infection in a subject in need of such therapy with said compounds. Compounds of the present invention interfere with the life cycle of the hepatitis C virus and are also useful as antiviral agents.

In its principal aspect, the present invention provides a compound of Formula (I)

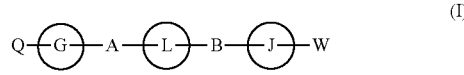

or a pharmaceutically acceptable salt thereof, wherein:

A and B are each independently absent or selected from the group consisting of O, optionally substituted $C_1$-$C_4$ alkyl, optionally substituted $C_2$-$C_4$ alkenyl, and optionally substituted $C_2$-$C_4$ alkynyl;

Ring L is a monocyclic or polycyclic group independently selected from the group consisting of aryl, heteroaryl, heterocyclic, $C_3$-$C_8$ cycloalkyl, and $C_3$-$C_8$ cycloalkenyl, each optionally substituted;

Ring G and ring J are each independently an optionally substituted 5- or 5/6-fused membered heteroaryl; wherein the 5-membered heteroaryl contains one or more nitrogen, and wherein the 6-membered ring of said 5/6-fused membered heteroaryl is attached to one of A, B and ring L, and is aryl or heteroaryl;

W is selected from

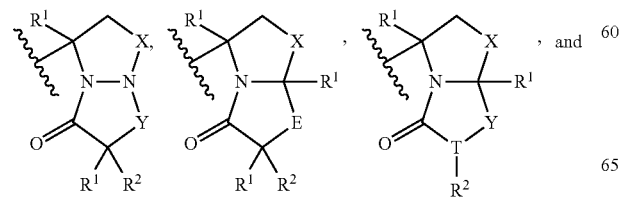

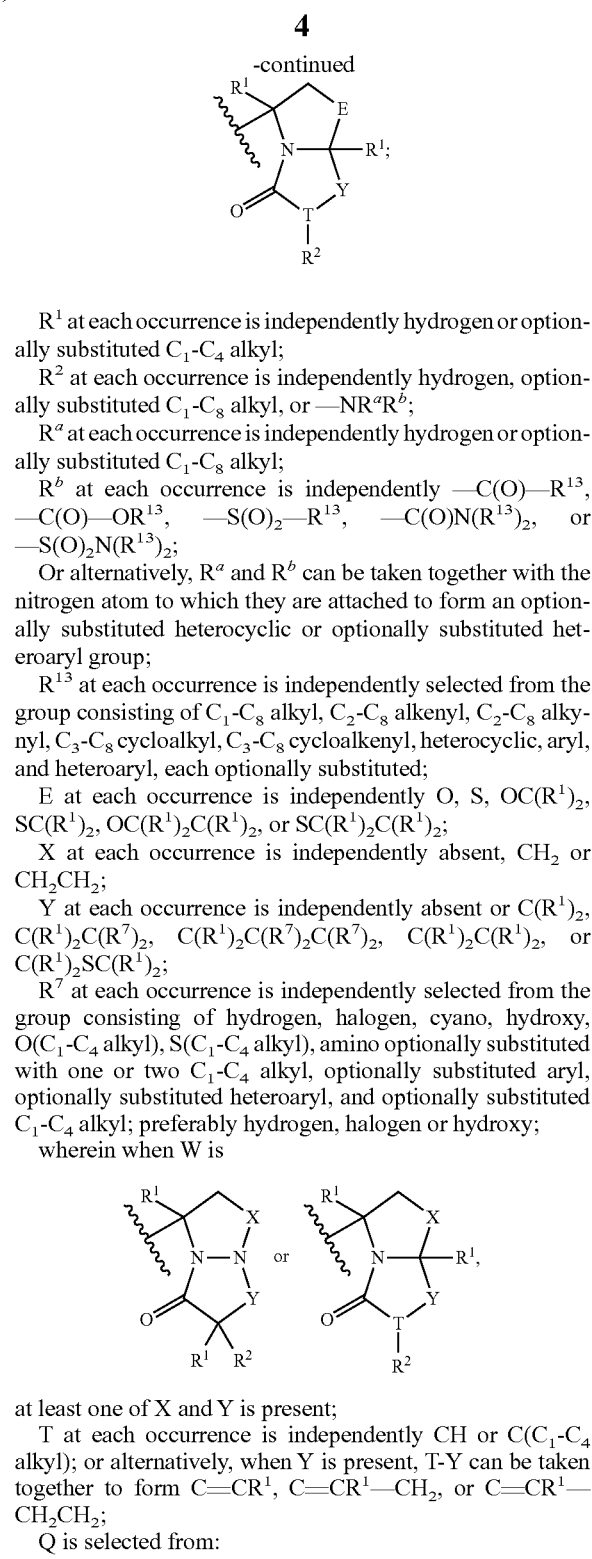

$R^1$ at each occurrence is independently hydrogen or optionally substituted $C_1$-$C_4$ alkyl;

$R^2$ at each occurrence is independently hydrogen, optionally substituted $C_1$-$C_8$ alkyl, or $-NR^aR^b$;

$R^a$ at each occurrence is independently hydrogen or optionally substituted $C_1$-$C_8$ alkyl;

$R^b$ at each occurrence is independently $-C(O)-R^{13}$, $-C(O)-OR^{13}$, $-S(O)_2-R^{13}$, $-C(O)N(R^{13})_2$, or $-S(O)_2N(R^{13})_2$;

Or alternatively, $R^a$ and $R^b$ can be taken together with the nitrogen atom to which they are attached to form an optionally substituted heterocyclic or optionally substituted heteroaryl group;

$R^{13}$ at each occurrence is independently selected from the group consisting of $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, heterocyclic, aryl, and heteroaryl, each optionally substituted;

E at each occurrence is independently O, S, $OC(R^1)_2$, $SC(R^1)_2$, $OC(R^1)_2C(R^1)_2$, or $SC(R^1)_2C(R^1)_2$;

X at each occurrence is independently absent, $CH_2$ or $CH_2CH_2$;

Y at each occurrence is independently absent or $C(R^1)_2$, $C(R^1)_2C(R^7)_2$, $C(R^1)_2C(R^7)_2C(R^7)_2$, $C(R^1)_2C(R^1)_2$, or $C(R^1)_2SC(R^1)_2$;

$R^7$ at each occurrence is independently selected from the group consisting of hydrogen, halogen, cyano, hydroxy, $O(C_1$-$C_4$ alkyl), $S(C_1$-$C_4$ alkyl), amino optionally substituted with one or two $C_1$-$C_4$ alkyl, optionally substituted aryl, optionally substituted heteroaryl, and optionally substituted $C_1$-$C_4$ alkyl; preferably hydrogen, halogen or hydroxy;

wherein when W is

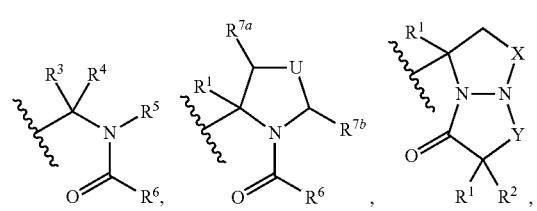

at least one of X and Y is present;

T at each occurrence is independently CH or $C(C_1$-$C_4$ alkyl); or alternatively, when Y is present, T-Y can be taken together to form $C=CR^1$, $C=CR^1-CH_2$, or $C=CR^1-CH_2CH_2$;

Q is selected from:

-continued

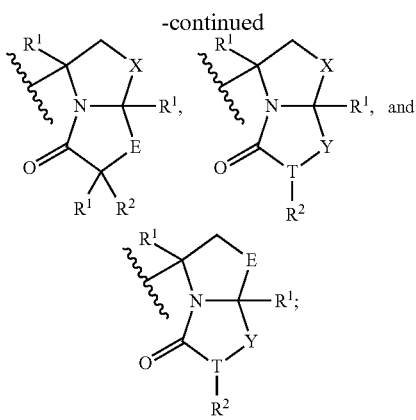

wherein when Q is

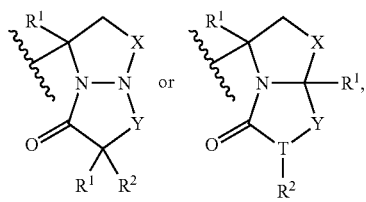

at least one of X and Y is present:

U is absent or selected from the group consisting of O, S, S(O), SO₂, NC(O)—(C₁-C₄ alkyl), C(O), protected carbonyl, OCH₂, OCH₂CH₂, SCH₂, SCH₂CH₂, C(R⁷)₂, and C(R⁷)₂C (R⁷)₂; preferably C(R⁷)₂;

R³ and R⁴ are each independently selected from the group consisting of hydrogen, optionally substituted C₁-C₈ alkyl, optionally substituted C₂-C₈ alkenyl, and optionally substituted C₃-C₈ cycloalkyl; preferably hydrogen or optionally substituted C₁-C₄ alkyl; or alternatively, R³ and R⁴ can be taken together with the carbon atom to which they are attached to form optionally substituted C₃-C₈ cycloalkyl or optionally substituted heterocyclic;

R⁵ is hydrogen, optionally substituted C₁-C₈ alkyl, or optionally substituted C₃-C₈ cycloalkyl; preferably hydrogen or optionally substituted C₁-C₄ alkyl;

R⁶ occurrence selected from the group consisting of optionally substituted O(C₁-C₈ alkyl), optionally substituted amino, —NR¹¹NRᵃRᵇ or R¹²;

R¹¹ occurrence is selected from the group consisting of hydrogen, C₁-C₈ alkyl, C₂-C₈ alkenyl, C₂-C₈ alkynyl, C₃-C₈ cycloalkyl, C₃-C₈ cycloalkenyl, heterocyclic, aryl, and heteroaryl, each optionally substituted;

R¹² at each occurrence is independently selected from the group consisting of hydrogen, C₁-C₈ alkyl, C₂-C₈ alkenyl, C₂-C₈ alkynyl, C₃-C₈ cycloalkyl, C₃-C₈ cycloalkenyl, heterocyclic, aryl, and heteroaryl, each optionally substituted; preferably optionally substituted C₁-C₈ alkyl; also preferably C₁-C₈ alkyl optionally substituted with amino, hydroxy, protected amino or O(C₁-C₄ alkyl); and R⁷ᵃ and R⁷ᵇ at each occurrence are each independently selected from the group consisting of hydrogen, optionally substituted aryl, and optionally substituted C₁-C₄ alkyl; or alternatively, CHR⁷ᵃ—U or CHR⁷ᵇ—U can be taken together to form a group selected from CH═CH, optionally substituted C₃-C₈ cycloalkyl, optionally substituted aryl, or optionally substituted heterocyclic; or yet alternatively, U, R⁷ᵃ, and R⁷ᵇ can be taken together with the carbon atoms to which they are attached to form a bridged 5- to 7-membered ring.

Each preferred group stated above can be taken in combination with one, any or all other preferred groups.

In another aspect, the present invention provides a pharmaceutical composition comprising a therapeutically effective amount of a compound or combination of compounds of the present invention, or a pharmaceutically acceptable salt thereof, in combination with a pharmaceutically acceptable carrier or excipient.

In yet another aspect, the present invention provides a method of inhibiting the replication of a RNA-containing virus comprising contacting said virus with said pharmaceutical composition. Particularly, this invention is directed to methods of inhibiting the replication of HCV.

In still another aspect, the present invention provides a method of treating or preventing infection caused by an RNA-containing virus comprising administering to a patient in need of such treatment with said pharmaceutical composition. Particularly, this invention is directed to methods of treating or preventing infection caused by HCV.

Yet another aspect of the present invention provides the use of a compound or combination of compounds of the present invention, or a therapeutically acceptable salt thereof, as defined hereinafter, in the preparation of a medicament for the treatment or prevention of infection caused by RNA-containing virus, specifically HCV.

DETAILED DESCRIPTION OF THE INVENTION

The present invention relates to compounds of Formula (I) as illustrated above, or a pharmaceutically acceptable salt thereof.

The compounds of the invention have utility in inhibiting the replication of RNA-containing virus, including, for example, HCV. Other compounds useful for inhibiting the replication of RNA-containing viruses and/or for the treatment or prophylaxis of HCV infection have been described in copending U.S. application Ser. No. 12/702,673 filed Feb. 9, 2010 entitled "Linked Dibenzimidiazole Antivirals"; U.S. application Ser. No. 12/702,692 filed Feb. 9, 2010 entitled "Linked Dibenzimidiazole Derivatives"; U.S. application Ser. No. 12/702,802 filed Feb. 9, 2010 entitled "Linked Dibenzimidiazole Derivatives"; U.S. application Ser. No. 12/707,190 filed Feb. 17, 2010 entitled "Linked Diimidazole Antivirals"; U.S. application Ser. No. 12/707,200 filed Feb. 17, 2010 entitled "Linked Diimidazole Antivirals"; U.S. application Ser. No. 12/707,210 filed Feb. 17, 2010 entitled "Hepatitis C Virus Inhibitors"; U.S. application Ser. No. 12/714,583 filed Mar. 1, 2010 entitled "Novel Benzimidazole Derivatives"; and U.S. application Ser. No. 12/714,576 filed Mar. 1, 2010 entitled "Hepatitis C Virus Inhibitors"; U.S. Provisional Application Ser. No. 61/187,374 filed Jun. 16, 2009 entitled "Hepatitis C Virus Inhibitors"; U.S. Provisional Application Ser. No. 61/222,586 filed Jul. 2, 2009 entitled "Hepatitis C Virus Inhibitors"; U.S. Provisional Application Ser. No. 61/241,489 filed Sep. 11, 2009 entitled "Hepatitis C Virus Inhibitors"; U.S. Provisional Application Ser. No. 61/241,578 filed Sep. 11, 2009 entitled "Hepatitis C Virus Inhibitors"; U.S. Provisional Application Ser. No. 61/241, 595 filed Sep. 11, 2009 entitled "Hepatitis C Virus Inhibitors"; U.S. Provisional Application Ser. No. 61/241,617 filed Sep. 11, 2009 entitled "Hepatitis C Virus Inhibitors"; U.S. Provisional Application Ser. No. 61/241,577 filed Sep. 11, 2009 entitled "Hepatitis C Virus Inhibitors"; U.S. Provisional Application Ser. No. 61/241,598 filed Sep. 11, 2009 entitled "Hepatitis C Virus Inhibitors"; U.S. Provisional Application Ser. No. 61/286,178 filed Dec. 14, 2009 entitled "Hepatitis C Virus Inhibitors"; U.S. Provisional Application Ser. No. 61/297,918 filed Jan. 25, 2010 entitled "Hepatitis C Virus Inhibitors"; U.S. Provisional Application Ser. No. 61/314,304 filed Mar. 16, 2010 entitled "Hepatitis C Virus Inhibitors"; U.S. Provisional Application Ser. No. 61/322,438 filed Apr. 9, 2010 entitled "Hepatitis C Virus Inhibitors"; U.S. Provisional Application Ser. No. 61/351,327 filed Jun. 4, 2010 entitled "Hepatitis C Virus Inhibitors"; and the contents of each of which are expressly incorporated by reference herein.

In another embodiment, the present invention relates to compounds of Formula (I), or a pharmaceutically acceptable salt thereof; wherein W is selected from:

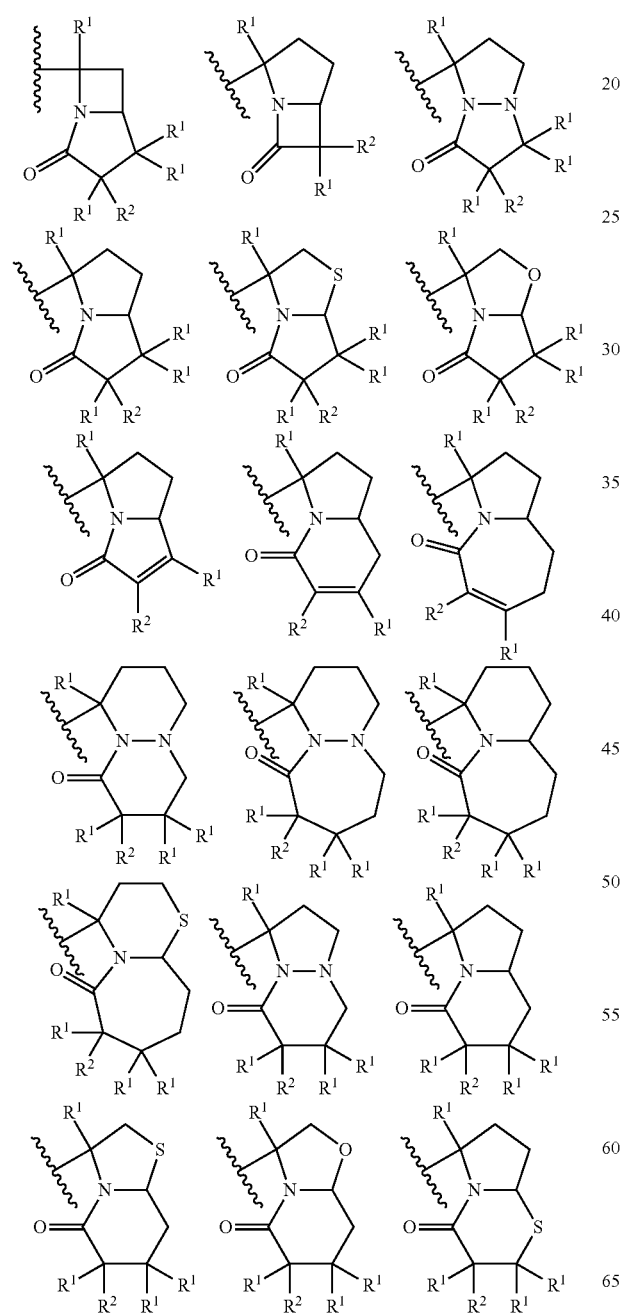

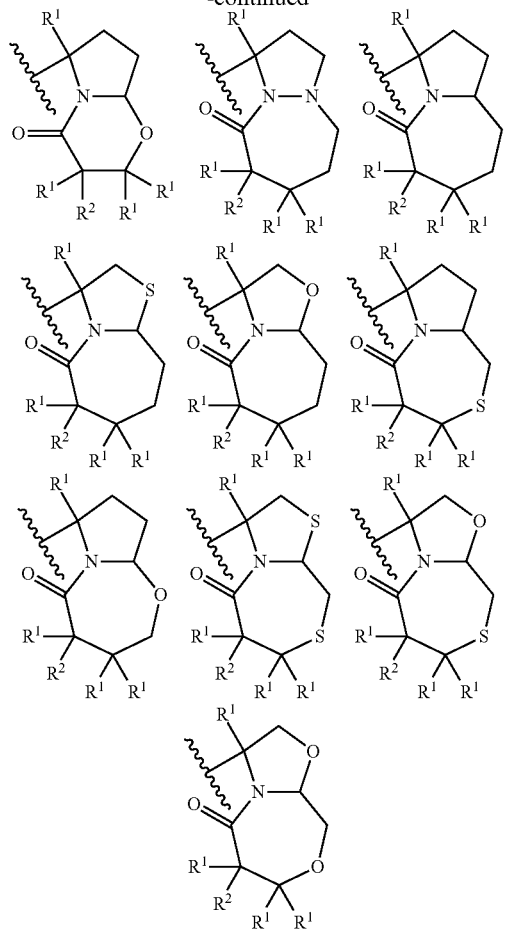

wherein $R^1$ and $R^2$ are as previously defined.

In yet another embodiment, the present invention relates to compounds of Formula (I), or a pharmaceutically acceptable salt thereof; wherein G and J are each independently an optionally substituted five-membered heteroaryl containing one or more nitrogen, and are each C-attached.

In still another embodiment, the present invention relates to compounds of Formula (I), or a pharmaceutically acceptable salt thereof; wherein ring G and ring J are each independently an optionally substituted 5/6-membered fused heteroaryl; wherein the 5-membered ring of said 5/6-membered fused heteroaryl is a heteroaryl containing one or more nitrogens and wherein the 5-membered ring is C-attached to group Q or W, and wherein the 6-membered ring of said 5/6 membered fused aryl is aryl or heteroaryl and is C-attached to one of A, B, and ring L.

In yet another embodiment, the present invention relates to compounds of Formula (I), or a pharmaceutically acceptable salt thereof; wherein one of G and J is a 5-membered heteroaryl containing one or more nitrogen and is C-attached, and the other is an optionally substituted 5/6-membered fused heteroaryl; wherein the 5-membered ring of said 5/6-membered fused heteroaryl contains one or more nitrogen and is C-attached to group Q or W, and wherein the 6-membered ring of said 5/6-membered fused heteroaryl is aryl or heteroaryl and is C-attached to one of A, B, and ring L.

In still another embodiment, the present invention relates to compounds of Formula (I), or a pharmaceutically acceptable salt thereof; wherein ring G and ring J are each independently selected from the following heteroaryl groups:

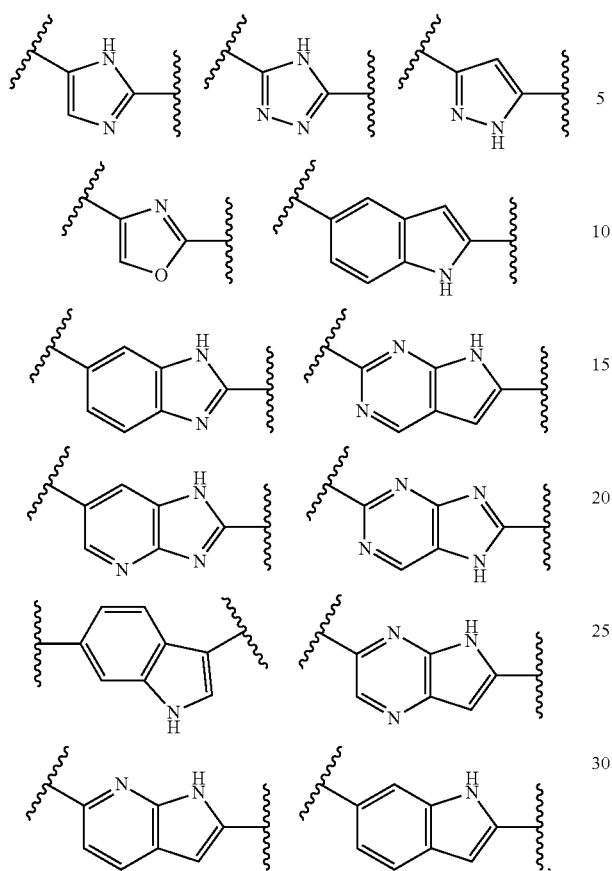

wherein each of the above said heteroaryl groups is optionally substituted.

In yet another embodiment, the present invention relates to compounds of Formulae (Ia-1~Ia-6), or a pharmaceutically acceptable salt thereof:

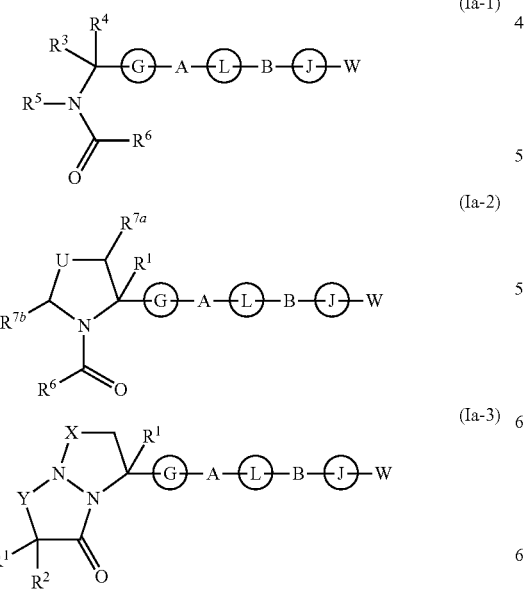

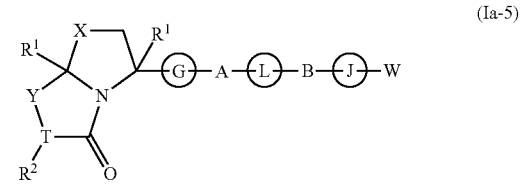

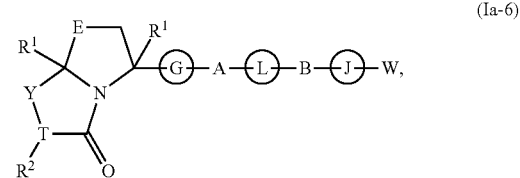

wherein A, B, E, ring G, ring J, ring L, T, U, W, X, Y, $R^1$, $R^2$, $R^3$, $R^4$, $R^5$, and $R^6$ are as previously defined.

In yet another embodiment, the present invention relates to compounds of Formula (Ia-7), or a pharmaceutically acceptable salt thereof:

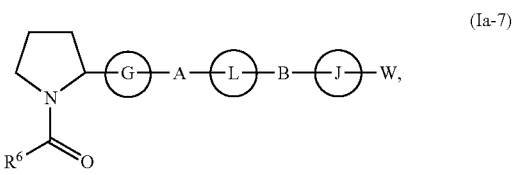

wherein A, B, ring G, ring J, ring L, W, and $R^6$ are as previously defined.

In yet another embodiment, the present invention relates to compounds of Formula (Ia-9), or a pharmaceutically acceptable salt thereof:

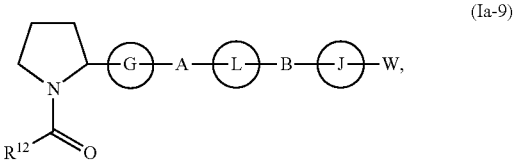

wherein A, B, ring G, ring J, ring L, W, and $R^{12}$ are as previously defined.

In still another embodiment, the present invention relates to compounds of Formula (Ia-10), or a pharmaceutically acceptable salt thereof:

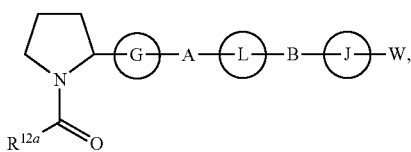

(Ia-10)

wherein A, B, ring G, ring J, ring L, and W are as previously defined and $R^{12a}$ is independently an optionally substituted $C_1$-$C_8$ alkyl optionally substituted with amino, hydroxy, protected amino or O($C_1$-$C_4$ alkyl).

In still another embodiment, the present invention relates to compounds of Formulae (Ib-1~Ib-4), or a pharmaceutically acceptable salt thereof:

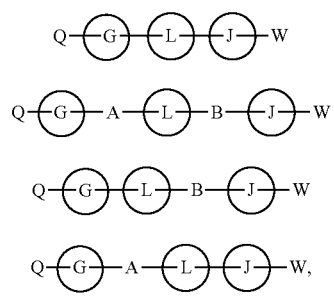

(Ib-1)
(Ib-2)
(Ib-3)
(Ib-4)

wherein ring G, ring J, ring L, Q, and W are as previously defined; in Formula Ib-2, A and B are each present; and wherein A and B are as previously defined.

In still another embodiment, the present invention relates to compounds of Formulae (Ib-5~Ib-6), or a pharmaceutically acceptable salt thereof:

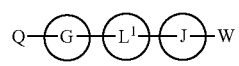

(Ib-5)

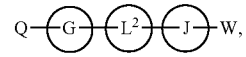

(Ib-6)

wherein ring G, ring J, Q, and W are as previously defined; ring $L^1$ is an optionally substituted aryl or heteroaryl; and ring $L^2$ is an optionally substituted bicyclic aryl or bicyclic heteroaryl; wherein the rings of said bicyclic aryl or bicyclic heteroaryl can be fused or covalently attached.

In still another embodiment, the present invention relates to compounds of Formula (Ib-7~Ib-8), or a pharmaceutically acceptable salt thereof:

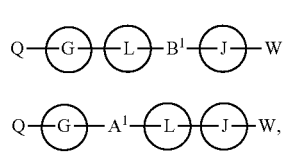

(Ib-7)
(Ib-8)

wherein ring G, ring J, ring L, Q, and W are as previously defined; $A^1$ and $B^1$ are each independently optionally substituted $C_2$-$C_4$ alkenyl or optionally substituted $C_2$-$C_4$ alkynyl.

Representative compounds of the present invention are those selected from compounds 1-376 compiled in the following tables:

TABLE 1

Compounds 1-219.

| Entry | |
|---|---|
| 1 | |
| 2 | |

TABLE 1-continued
Compounds 1-219.
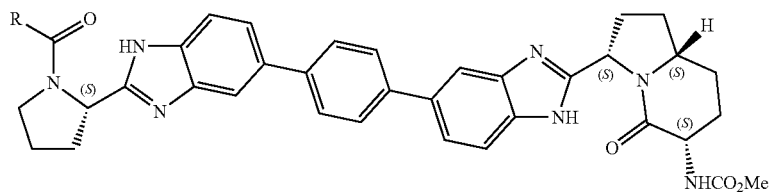
| Entry | R group |
|---|---|
| 3 | (S)-2-(dimethylamino)-2-phenylacetyl |
| 4 | (S)-2-hydroxypropanoyl |
| 5 | (S)-2-hydroxybutanoyl |
| 6 | propanoyl |
| 7 | methoxyacetyl |
| 8 | N,N-dimethylcarbamoyl |
| 9 | methoxycarbonyl |
| 10 | 4,6-dioxoheptanoyl |
| 11 | (S)-2-hydroxy-3-methylbutanoyl |

TABLE 1-continued
Compounds 1-219.
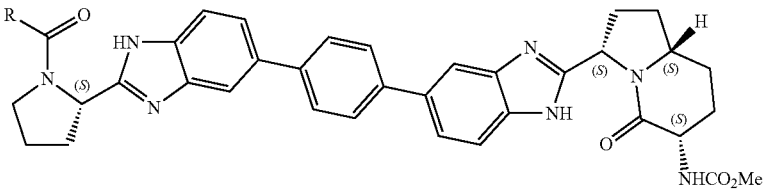
| Entry | R—C(O)— |
|---|---|
| 12 | 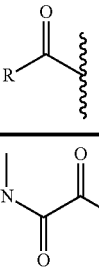 |
| 13 | 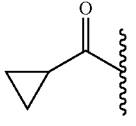 |
| 14 | 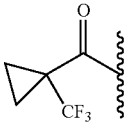 [SMILES: *C(=O)C1(C(F)(F)F)CC1] |
| 15 | 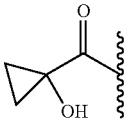 [SMILES: *C(=O)C1(O)CC1] |
| 16 | 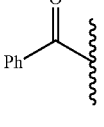 |
| 17 | 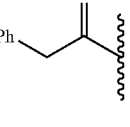 |
| 18 | 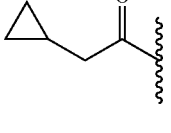 |
| 19 | 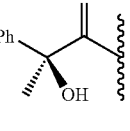 |
| 20 | 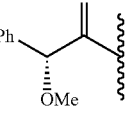 |

TABLE 1-continued

Compounds 1-219.

| Entry | R group structure |
|---|---|
| 21 | Ph-CH(OH)-C(=O)- (S configuration) |
| 22 | (pyridin-3-yl)-CH₂-C(=O)- |
| 23 | (pyridin-4-yl)-CH₂-C(=O)- |
| 24 | Ph-CH₂-CH(OH)-C(=O)- (S configuration) |
| 25 | (tetrahydrofuran-2-yl)-C(=O)- |
| 26 | (tetrahydrofuran-2-yl)-C(=O)- |
| 27 | (tetrahydrofuran-3-yl)-C(=O)- |
| 28 | (1-methylpiperidin-4-yl)-C(=O)- |

TABLE 1-continued

Compounds 1-219.

| Entry | R-C(O)- group |
|---|---|
| 29 | 4-tetrahydropyranyl-C(O)- |
| 30 | morpholine-N-C(O)- |
| 31 | trans-4-(Boc-NH)-cyclohexyl-C(O)- |
| 32 | cis-4-(Boc-NH)-cyclohexyl-C(O)- |
| 33 | 1-Boc-piperidin-4-yl-C(O)- |
| 34 | 1-(diethylamino)piperidin-4-yl-C(O)- |
| 35 | trans-4-(MeO2C-NH)-cyclohexyl-C(O)- |

TABLE 1-continued
Compounds 1-219.
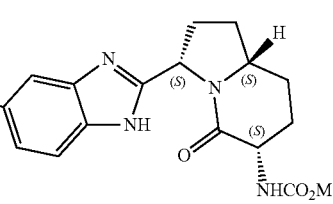
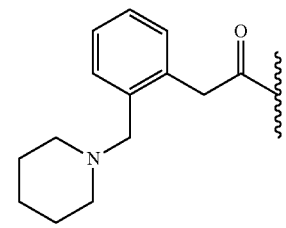 [SMILES: *C(=O)Cc1ccccc1CN1CCCCC1]
| Entry | |
|---|---|
| 36 | 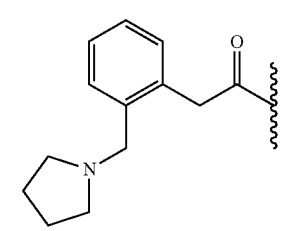 [SMILES: *C(=O)Cc1ccccc1CN1CCCC1] |
| 37 | 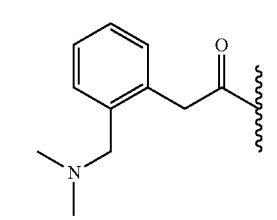 [SMILES: *C(=O)Cc1ccccc1CN(C)C] |
| 38 | 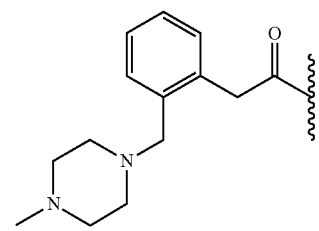 [SMILES: *C(=O)Cc1ccccc1CN1CCN(C)CC1] |
| 39 | |
| 40 | |

TABLE 1-continued
Compounds 1-219.
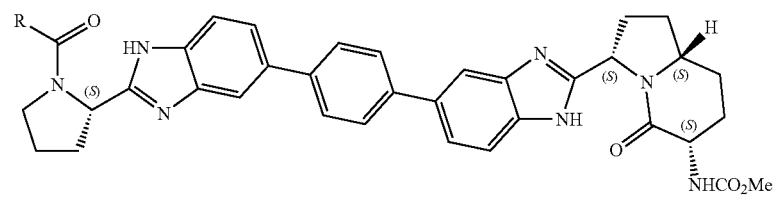
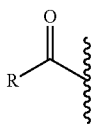
| Entry | |
|---|---|
| 41 | 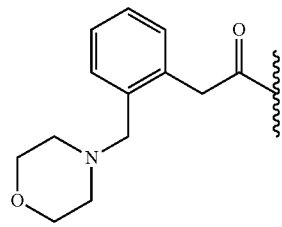 [SMILES: *C(=O)Cc1ccccc1CN1CCOCC1] |
| 42 | 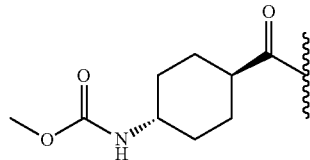 [SMILES: *C(=O)[C@H]1CC[C@H](NC(=O)OC)CC1] |
| 43 | 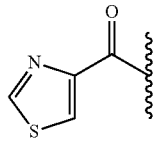 [SMILES: *C(=O)c1cscn1] |
| 44 | 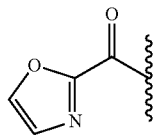 |
| 45 | 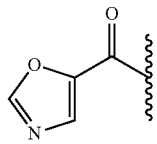 [SMILES: *C(=O)c1cnco1] |
| 46 | 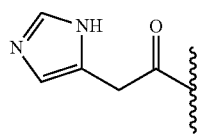 [SMILES: *C(=O)Cc1cnc[nH]1] |
| 47 | 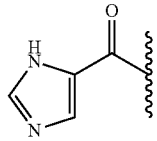 [SMILES: *C(=O)c1cnc[nH]1] |

TABLE 1-continued

Compounds 1-219.

| Entry | R-C(O)- group |
|---|---|
| 48 | 1-methyl-1H-imidazol-5-yl-C(O)- |
| 49 | (1H-tetrazol-5-yl)CH₂-C(O)- |
| 50 | 2-fluorophenyl-C(O)- |
| 51 | 4-(dimethylamino)phenyl-C(O)- |
| 52 | pyridin-4-yl-C(O)- |
| 53 | pyridin-3-yl-C(O)- |
| 54 | pyridin-2-yl-C(O)- |
| 55 | (S)-Ph-CH(OMe)-C(O)- |

TABLE 1-continued
Compounds 1-219.
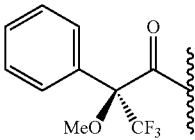
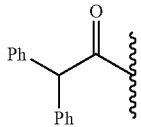
| Entry | |
|---|---|
| 56 | 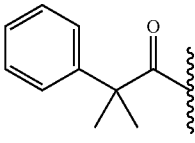 [SMILES: *C(=O)C(C)(C)c1ccccc1] |
| 57 | 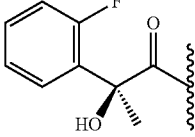 |
| 58 | 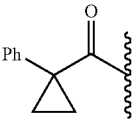 |
| 59 | 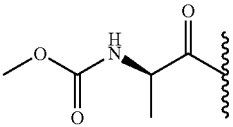 [SMILES: *C(=O)[C@@H](C)NC(=O)OC] |
| 60 | 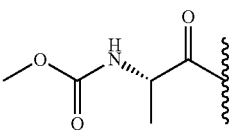 [SMILES: *C(=O)[C@H](C)NC(=O)OC] |
| 61 | 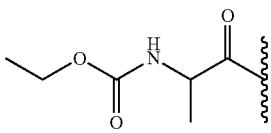 [SMILES: *C(=O)C(C)NC(=O)OCC] |
| 62 | |
| 63 | |

TABLE 1-continued
Compounds 1-219.
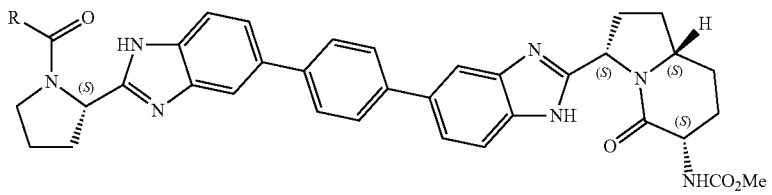
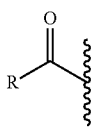
| Entry | |
|---|---|
| 64 | 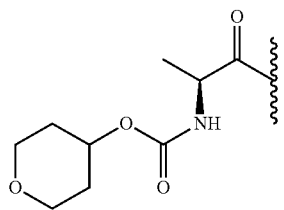 [SMILES: *C(=O)[C@H](C)NC(=O)OC1CCOCC1] |
| 65 | 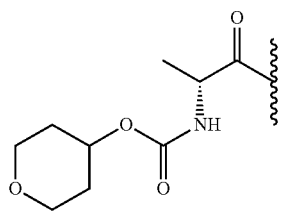 [SMILES: *C(=O)[C@@H](C)NC(=O)OC1CCOCC1] |
| 66 | 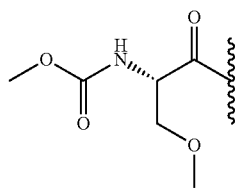 [SMILES: *C(=O)[C@H](COC)NC(=O)OC] |
| 67 | 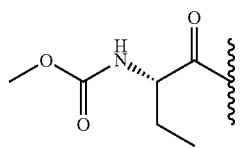 [SMILES: *C(=O)[C@H](CC)NC(=O)OC] |
| 68 | 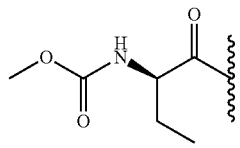 [SMILES: *C(=O)[C@@H](CC)NC(=O)OC] |
| 69 | 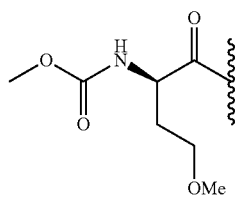 [SMILES: *C(=O)[C@@H](CCOC)NC(=O)OC] |

TABLE 1-continued

Compounds 1-219.

| Entry | R |
|-------|---|
| 70 | (2S,3R)-2-(methoxycarbonylamino)-3-hydroxybutanoyl |
| 71 | (2S,3S)-2-(methoxycarbonylamino)-3-hydroxybutanoyl |
| 72 | (2S,3R)-2-(methoxycarbonylamino)-3-methoxybutanoyl |
| 73 | (S)-2-(methoxycarbonylamino)pent-4-enoyl |
| 74 | (S)-2-(methoxycarbonylamino)pentanoyl |
| 75 | (S)-4-(dimethylamino)-2-(tert-butoxycarbonylamino)butanoyl |
| 76 | 2-(methoxycarbonylamino)-2-methylpropanoyl |

TABLE 1-continued

Compounds 1-219.

| Entry | |
|---|---|
| 77 | methyl carbamate, cyclopropyl |
| 78 | methyl carbamate, cyclopropyl (other stereochemistry) |
| 79 | methyl carbamate, C(CH₃)₂OH |
| 80 | methyl carbamate, CH₂CO₂Bn |
| 81 | methyl carbamate, CH₂CONH₂ |
| 82 | methyl carbamate, isopropyl |
| 83 | methyl carbamate, isopropyl |

TABLE 1-continued

Compounds 1-219.

| Entry | R-C(O)- group |
|---|---|
| 84 | methyl N-methyl-N-(carbamate)-Val-derived acyl group |
| 85 | (tetrahydropyran-4-yl)oxycarbonyl-Val-derived acyl group |
| 86 | (tetrahydropyran-4-yl)oxycarbonyl-Val-derived acyl group |
| 87 | ((3S)-tetrahydrofuran-3-yl)oxycarbonyl-Val-derived acyl group |
| 88 | methyl carbamate with diethylaminoethyl side chain |
| 89 | methyl carbamate with (2S,3R)-3-methyl-4-(OTBS) side chain |

TABLE 1-continued

Compounds 1-219.

| Entry | R—C(O)— group |
|---|---|
| 90 | methyl carbamate-NH-CH(CH(CH₃)CH₂-OTBS)-C(O)- |
| 91 | methyl carbamate-NH-CH(CH₂CH₂-N(Et)₂)-C(O)- (S) |
| 92 | methyl carbamate-NH-CH(tetrahydropyran-4-yl)-C(O)- (S) |
| 93 | methyl carbamate-NH-CH(tetrahydropyran-4-yl)-C(O)- |
| 94 | 1-(methoxycarbonylamino)cyclopropane-1-carbonyl |
| 95 | 1-(methoxycarbonylamino)cyclobutane-1-carbonyl |

TABLE 1-continued

Compounds 1-219.

| Entry | R-C(O)- group |
|---|---|
| 96 | 1-(methoxycarbonylamino)cyclopentyl carbonyl |
| 97 | (S)-2-(methoxycarbonylamino)-2-phenylacetyl |
| 98 | (S)-2-(2-chlorophenyl)-2-(methoxycarbonylamino)acetyl |
| 99 | (S)-2-acetamido-2-phenylacetyl |
| 100 | (S)-2-(3-methylureido)-2-phenylacetyl |
| 101 | (S)-2-(3,3-dimethylureido)-2-phenylacetyl |

TABLE 1-continued

Compounds 1-219.

| Entry | R group |
|---|---|
| 102 | (S)-2-phenyl-2-(3-ethylureido)acetyl |
| 103 | (S)-2-phenyl-2-(3-cyclopentylureido)acetyl |
| 104 | (S)-1-(methoxycarbonyl)azetidine-2-carbonyl |
| 105 | 1-Boc-azetidine-3-carbonyl |
| 106 | (S)-2-(methoxycarbonylamino)-3-(pyridin-2-yl)propanoyl |
| 107 | (S)-2-(methoxycarbonylamino)-3-(pyridin-3-yl)propanoyl |
| 108 | (S)-2-(methoxycarbonylamino)-3-(pyridin-4-yl)propanoyl |

TABLE 1-continued
Compounds 1-219.
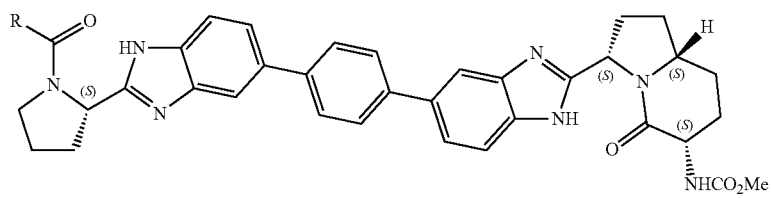
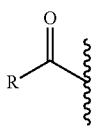
| Entry | |
|---|---|
| 109 | 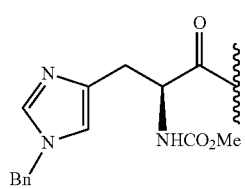 |
| 110 | 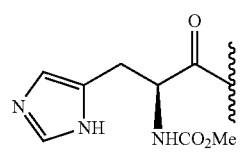 |
| 111 | 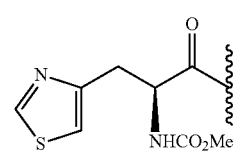 |
| 112 | 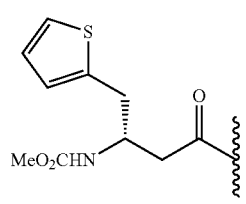 |
| 113 | 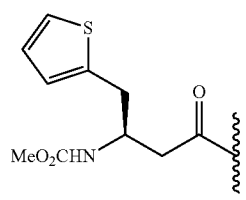 |
| 114 | 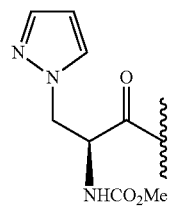 |

TABLE 1-continued

Compounds 1-219.

| Entry | R-C(O)- group |
|---|---|
| 115 | (1H-1,2,3-triazol-5-yl)methyl, α-NHCO₂Me |
| 116 | (1-methyl-1H-imidazol-2-yl)methyl, α-NHCO₂Me |
| 117 | (1-methyl-1H-imidazol-4-yl)methyl, α-NHCO₂Me |
| 118 | (S)-benzyl, α-NHCO₂Me |
| 119 | (R)-benzyl, α-NHCO₂Me |

TABLE 1-continued
Compounds 1-219.
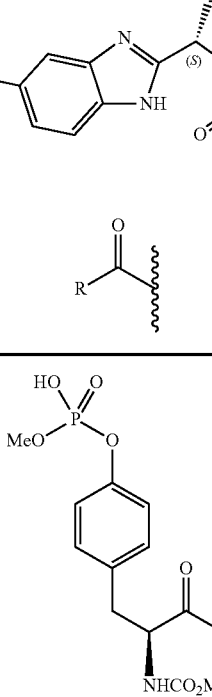
| Entry | |
|---|---|
| 120 | 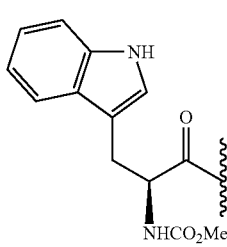 |
| 121 | 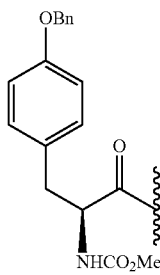 |
| 122 | 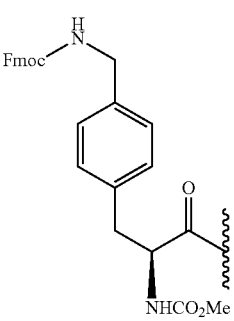 |
| 123 | |

TABLE 1-continued

Compounds 1-219.

| Entry | R group |
|---|---|
| 124 | (S)-2-oxo-oxazolidin-4-yl carbonyl |
| 125 | (R)-2-oxo-oxazolidin-4-yl carbonyl |
| 126 | (4S,5R)-5-methyl-2-oxo-oxazolidin-4-yl carbonyl |
| 127 | (1S,2S)-2-(methoxycarbonylamino)cyclopentyl carbonyl |
| 128 | (1S,2S)-2-(methoxycarbonylamino)pyrrolidin-2-yl carbonyl |
| 129 | (1S,2S)-2-(methoxycarbonylamino)cyclohexyl carbonyl |
| 130 | (1S,3S)-3-(methoxycarbonylamino)cyclopentyl carbonyl |

TABLE 1-continued

Compounds 1-219.

| Entry | R group structure |
|---|---|
| 131 | methyl carbamate-NH-cyclopentyl-C(O)- (trans substituted cyclopentane with NHCO₂Me and acyl groups) |
| 132 | methyl carbamate-NH-cyclohexyl-C(O)- (cis-1,2-disubstituted cyclohexane) |
| 133 | (R)-PhCH₂-CH(NHCO₂Me)-CH₂-C(O)- |
| 134 | (S)-PhCH₂-CH(NHCO₂Me)-CH₂-C(O)- |
| 135 | (2-F-C₆H₄)-CH₂-CH(NHCO₂Me)-CH₂-C(O)- |

TABLE 1-continued
Compounds 1-219.
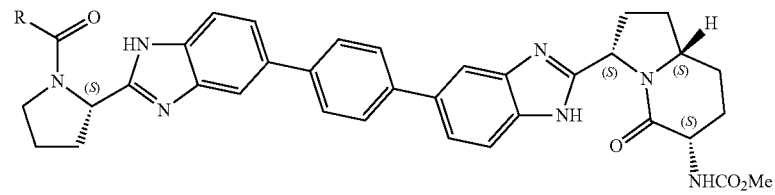
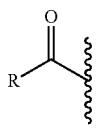
| Entry | |
|---|---|
| 136 | 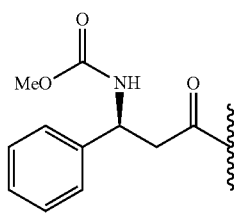 [SMILES: *C(=O)C[C@H](NC(=O)OC)c1ccccc1] |
| 137 | 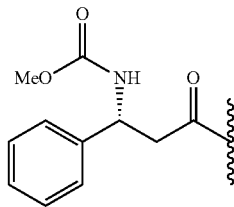 [SMILES: *C(=O)C[C@@H](NC(=O)OC)c1ccccc1] |
| 138 | 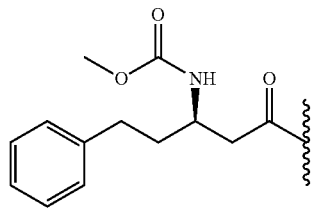 [SMILES: *C(=O)C[C@@H](CCc1ccccc1)NC(=O)OC] |
| 139 | 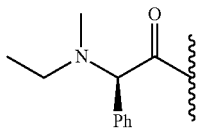 [SMILES: *C(=O)[C@@H](c1ccccc1)N(C)CC] |
| 140 | 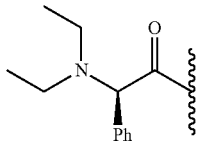 [SMILES: *C(=O)[C@@H](c1ccccc1)N(CC)CC] |
| 141 | 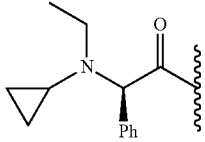 [SMILES: *C(=O)[C@@H](c1ccccc1)N(CC)C1CC1] |

TABLE 1-continued

Compounds 1-219.

| Entry | R |
|---|---|
| 142 | (phenyl)(7-azabicyclo[2.2.1]heptan-7-yl)methyl- carbonyl (S) |
| 143 | (phenyl)(7-azabicyclo[2.2.1]heptan-7-yl)methyl- carbonyl (R) |
| 144 | (4-methylpiperazin-1-yl)(phenyl)methylcarbonyl |
| 145 | (pyrrolidin-1-yl)(phenyl)methylcarbonyl |
| 146 | ((S)-3-fluoropyrrolidin-1-yl)(phenyl)methylcarbonyl |
| 147 | ((R)-3-fluoropyrrolidin-1-yl)(phenyl)methylcarbonyl |
| 148 | (4-phenylpiperidin-1-yl)(phenyl)methylcarbonyl |

TABLE 1-continued
Compounds 1-219.
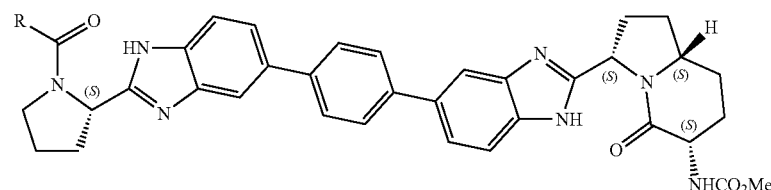
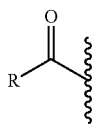
| Entry | |
|---|---|
| 149 | 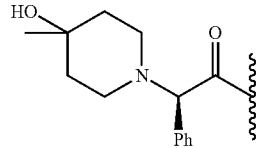 [SMILES: *C(=O)[C@@H](c1ccccc1)N1CCC(C)(O)CC1] |
| 150 | 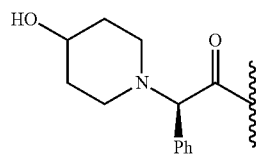 [SMILES: *C(=O)[C@@H](c1ccccc1)N1CCC(O)CC1] |
| 151 | 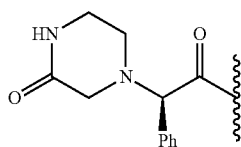 [SMILES: *C(=O)[C@@H](c1ccccc1)N1CCNC(=O)C1] |
| 152 | 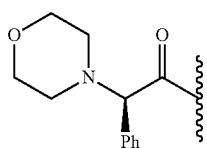 [SMILES: *C(=O)[C@@H](c1ccccc1)N1CCOCC1] |
| 153 | 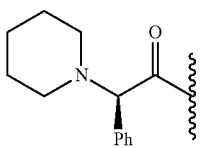 [SMILES: *C(=O)[C@@H](c1ccccc1)N1CCCCC1] |
| 154 | 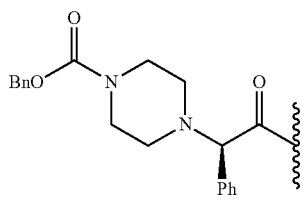 [SMILES: *C(=O)[C@@H](c1ccccc1)N1CCN(C(=O)OCc2ccccc2)CC1] |
| 155 | 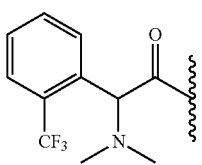 |

TABLE 1-continued
Compounds 1-219.
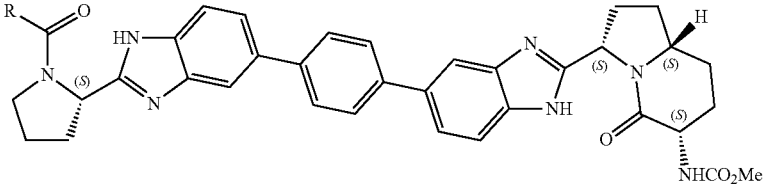
| Entry | |
|---|---|
| 156 | 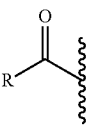 |
| 157 | 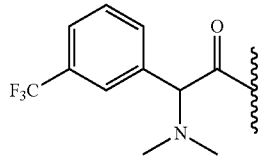 |
| 158 | 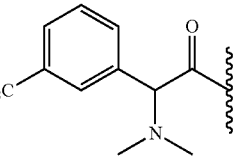 |
| 159 | 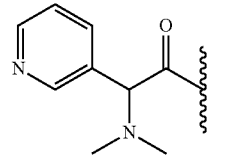 |
| 160 | 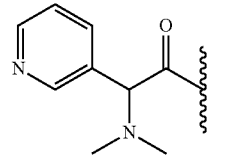 |
| 161 | 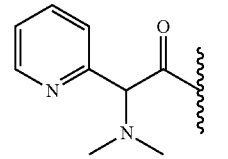 [SMILES: *C(=O)C(c1ccccn1)N(C)C] |
| 162 | 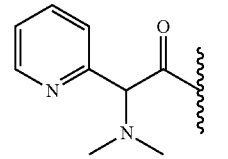 [SMILES: *C(=O)C(c1ccccn1)N(C)C] |

TABLE 1-continued

Compounds 1-219.

| Entry | R group |
|---|---|
| 163 | (S)-2-fluorophenyl, N(Me)₂ |
| 164 | 2-chlorophenyl, N(Me)₂ |
| 165 | 4-chlorophenyl, N(Me)₂ |
| 166 | (S)-2-fluorophenyl, N(Me)₂ |
| 167 | 2-fluorophenyl, N(Me)₂ |
| 168 | 3-fluorophenyl, N(Me)₂ |
| 169 | (S)-2-fluorophenyl, piperidinyl |

TABLE 1-continued

Compounds 1-219.

| Entry | |
|---|---|
| 170 | 4-nitrophenyl-CH(NMe₂)-C(=O)- |
| 171 | 2-methylthiazol-4-yl-CH(NMe₂)-C(=O)- |
| 172 | benzo[d]isoxazol-3-yl-CH(NMe₂)-C(=O)- |
| 173 | thiophen-2-yl-CH(NMe₂)-C(=O)- |
| 174 | thiophen-3-yl-CH(NMe₂)-C(=O)- |
| 175 | quinolin-3-yl-CH(NMe₂)-C(=O)- |
| 176 | benzo[b]thiophen-3-yl-CH(NMe₂)-C(=O)- |

TABLE 1-continued
Compounds 1-219.
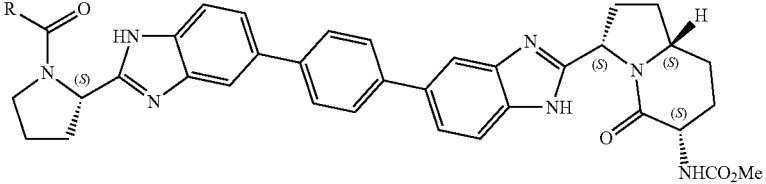
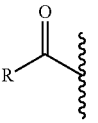
| Entry | |
|---|---|
| 177 | 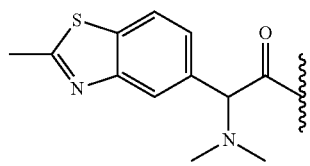 [SMILES: *C(=O)C(c1ccc2sc(C)nc2c1)N(C)C] |
| 178 | 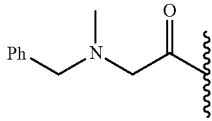 |
| 179 | 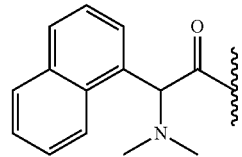 [SMILES: *C(=O)C(c1cccc2ccccc12)N(C)C] |
| 180 | 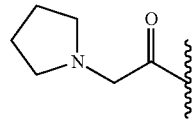 [SMILES: *C(=O)CN1CCCC1] |
| 181 | 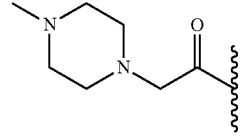 [SMILES: *C(=O)CN1CCN(C)CC1] |
| 182 | 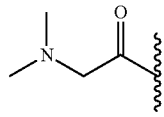 |
| 183 | 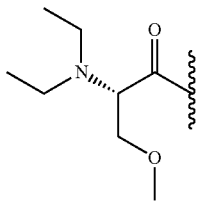 [SMILES: *C(=O)[C@H](COC)N(CC)CC] |
| 184 | 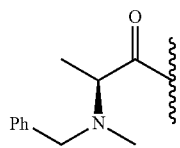 [SMILES: *C(=O)[C@H](C)N(C)Cc1ccccc1] |

TABLE 1-continued

Compounds 1-219.

| Entry | R group |
|---|---|
| 185 | CH₃-CH(N(CH₂CH₂CH₃)₂)-C(=O)- (S) |
| 186 | CH₃-CH(N(CH₂CH₂CH₃)₂)-C(=O)- (R) |
| 187 | CH₃-CH(N(CH₃)₂)-C(=O)- (S) |
| 188 | CH₃-CH(N(CH₃)₂)-C(=O)- (R) |
| 189 | CH₃C(=O)NH-CH(CH₃)-C(=O)- (S) |
| 190 | CH₃-CH(N(CH₂CH₃)₂)-C(=O)- (S) |
| 191 | CH₃-CH(N(CH₂CH₃)₂)-C(=O)- (R) |
| 192 | CH₃C(=O)NH-CH(CH₃)-C(=O)- (R) |

TABLE 1-continued

Compounds 1-219.

| Entry | R group |
|---|---|
| 193 | (diethylamino)(methoxymethyl)-CH-C(O)- |
| 194 | (diethylamino)(ethyl)-CH-C(O)- |
| 195 | (diethylamino)(ethyl)-CH-C(O)- |
| 196 | N-benzyl-N-methylamino-isopropyl-CH-C(O)- |
| 197 | (dimethylamino)(methyl)-CH-C(O)- |
| 198 | (diethylamino)(CH2C(O)NH2)-CH-C(O)- |
| 199 | (diethylamino)(isopropyl)-CH-C(O)- |

TABLE 1-continued

Compounds 1-219.

| Entry | R group structure |
|---|---|
| 200 | 2-imidazolinyl-NH-Val- (imidazoline NH, CH(iPr)) |
| 201 | 2-imidazolinyl-NH-Val- |
| 202 | 1-methyl-2-imidazolinyl-NH-Val- |
| 203 | 5-amino-1-methyl-1,2,4-triazol-3-yl-NH-Val- |
| 204 | 2-thiazolinyl-NH-Val- |
| 205 | 5-amino-1H-1,2,4-triazol-3-yl-NH-Val- |
| 206 | pyridin-3-yl-NH-Val- |

TABLE 1-continued

Compounds 1-219.

| Entry | R group |
|---|---|
| 207 | 4-pyrimidinyl-NH-CH(iPr)-C(O)- |
| 208 | (5-amino-1,2,4-oxadiazol-3-yl)-NH-CH(iPr)-C(O)- |
| 209 | Et₂N-CH(tBu)-C(O)- |
| 210 | Me₂N-CH(CH₂Ph)-C(O)- |
| 211 | pyrrolidine-2-carbonyl |
| 212 | 5-oxopyrrolidine-2-carbonyl (pyroglutamyl) |
| 213 | 5-pyrimidinyl-NH-CH(iPr)-C(O)- |

TABLE 1-continued
Compounds 1-219.
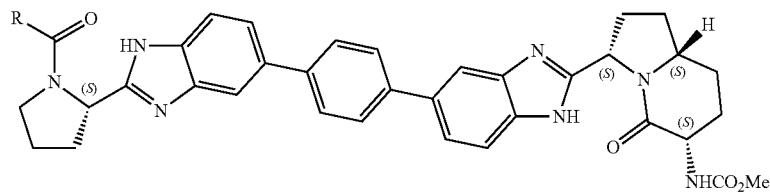
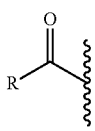
| Entry | |
|---|---|
| 214 | 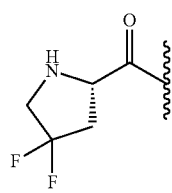 [SMILES: *C(=O)[C@@H]1CC(F)(F)CN1] |
| 215 | 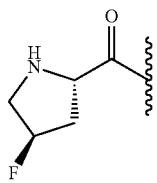 [SMILES: *C(=O)[C@@H]1C[C@@H](F)CN1] |
| 216 | 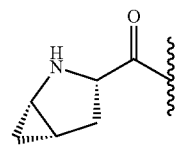 |
| 217 | 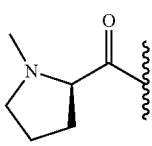 [SMILES: *C(=O)[C@H]1CCCN1C] |
| 218 | 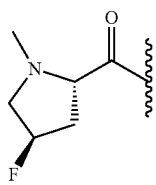 [SMILES: *C(=O)[C@@H]1C[C@@H](F)CN1C] |
| 219 | 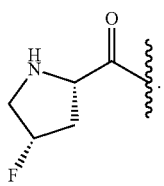 [SMILES: *C(=O)[C@@H]1C[C@H](F)CN1] |

TABLE 2

Compounds 220-237.

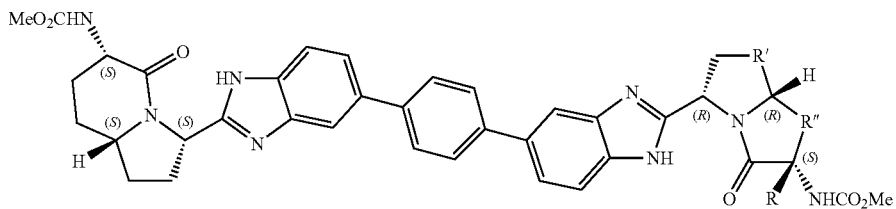

| Entry | R | R' | R" | Entry | R | R' | R" |
|---|---|---|---|---|---|---|---|
| 220 | H | $CH_2$ | $CH_2CH_2$ | 221 | H | $CH_2$ | $CH_2$ |
| 222 | Me | $CH_2$ | $CH_2CH_2$ | 223 | H | absent | $CH_2$ |
| 224 | H | O | $CH_2CH_2$ | 225 | H | $CH_2$ | absent |
| 226 | H | S | $CH_2CH_2$ | 227 | H | $CH_2$ | $OCH_2$ |
| 228 | H | O | $CH_2OCH_2$ | 229 | H | $CH_2$ | $SCH_2$ |
| 230 | H | S | $CH_2CMe_2$ | 231 | H | S | $CH_2SCH_2$ |
| 232 | H | $CH_2$ | $CH_2CH_2CH_2$ | 233 | H | $CH_2$ | $OCH_2CH_2$ |
| 234 | H | O | $CH_2CH_2CH_2$ | 235 | H | S | $CH_2CH_2CH_2$ |
| 236 | H | $CH_2$ | $CH_2CMe_2$ | 237 | $CHMe_2$ | O | $CH_2CH_2$. |

TABLE 3

Compounds 238-247.

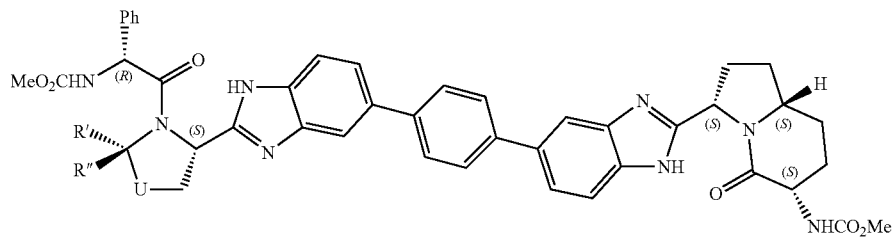

| Entry | R | R' | R" | U | Entry | R | R' | R" | U |
|---|---|---|---|---|---|---|---|---|---|
| 238 | Me | H | H | $CH_2$ | 239 | H | H | H | $CF_2$ |
| 240 | Me | H | H | S | 241 | H | H | H | ⁅F,H⁆ |
| 242 | Me | H | H | O | 243 | H | H | H | ⁅F,H⁆ |
| 244 | H | Ph | H | $CH_2$ | 245 | H | H | H | ⁅OH,H⁆ |
| 246 | H | H | Ph | $CH_2$ | 247 | H | H | H | ⁅OH,H⁆ |

TABLE 4
Compounds 248-251
248 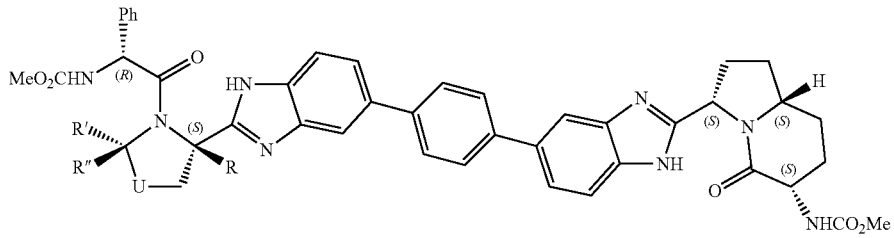
249 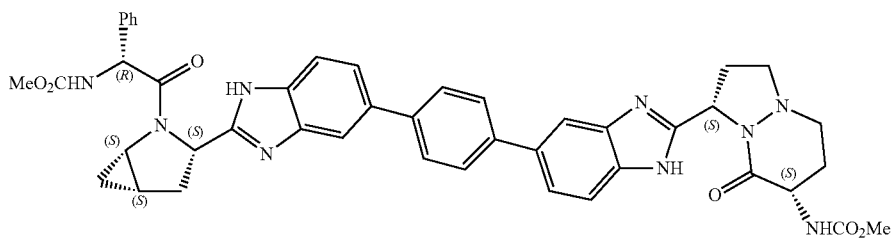
250 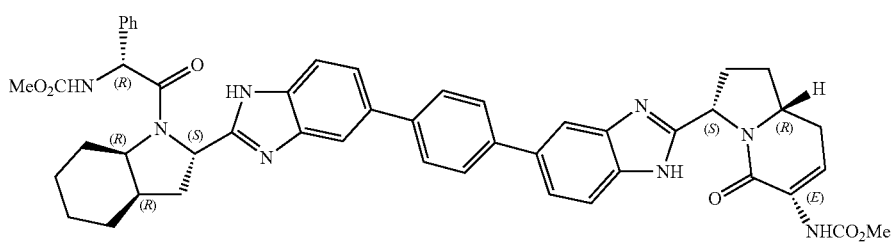
251 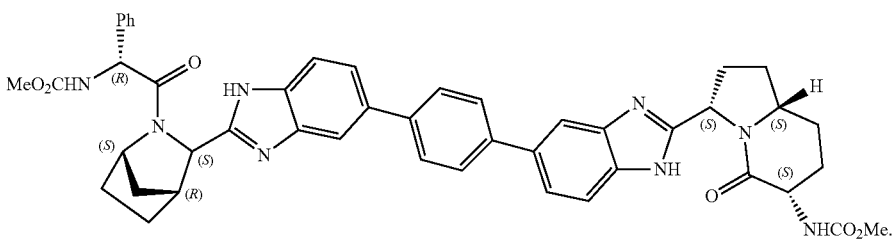
TABLE 5
Compounds 252-261.
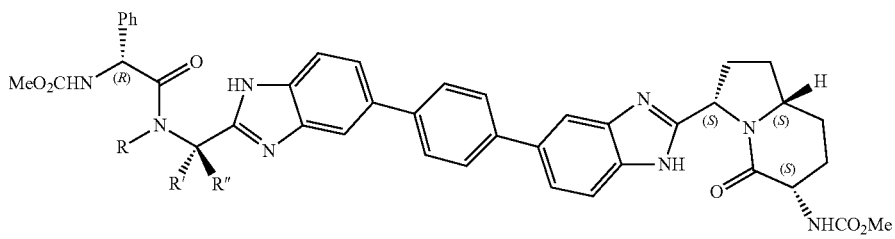
| Entry | R | R' | R" | Entry | R | R' | R" |
| --- | --- | --- | --- | --- | --- | --- | --- |
| 252 | Me | Me | H | 253 | H | Me | H |
| 254 | Me | H | Me | 255 | cyclopropyl | Me | H |

TABLE 5-continued
| 256 | Me | Me | Me | 257 | Me | cyclopropyl | H |
| 258 | Me | Allyl | H | 269 | Et | Me | H |
| 260 | Me | CHMe₂ | H | 261 | Me | Et | H. |
TABLE 6
Compounds 262-271.
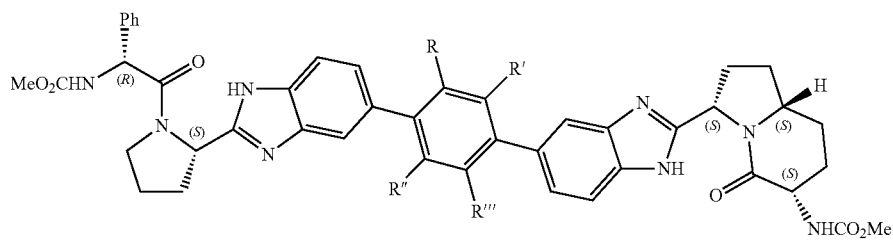
| Entry | R | R' | R'' | R''' | Entry | R | R' | R'' | R''' |
|---|---|---|---|---|---|---|---|---|---|
| 262 | F | H | H | H | 263 | F | F | H | H |
| 264 | Me | H | H | H | 265 | Me | Me | H | H |
| 266 | H | H | Me | Me | 267 | H | H | Et | Et |
| 278 | CF₃ | H | H | H | 269 | CF₃ | H | CF₃ | H |
| 270 | Cl | H | H | H | 271 | Cl | H | Cl | H. |
TABLE 7
Compounds 272-289.
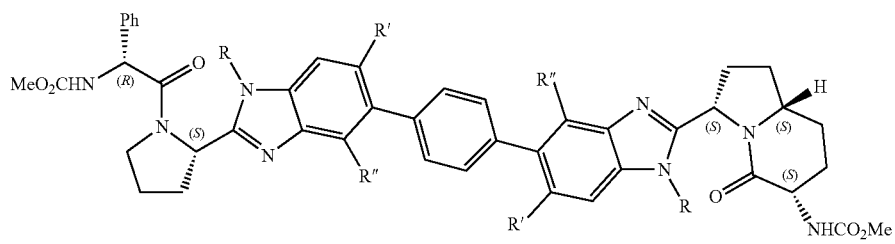
| Entry | R | R' | R'' | Entry | R | R' | R'' |
|---|---|---|---|---|---|---|---|
| 272 | Me | H | H | 273 | H | CO₂H | H |
| 274 | H | F | H | 275 | H | H | CO₂H |
| 276 | H | H | F | 277 | H | CO₂Me | H |
| 278 | H | Cl | H | 279 | H | H | CO₂Me |
| 280 | H | H | Cl | 281 | H | CONH₂ | H |
| 282 | H | Me | H | 283 | H | H | CONH₂ |
| 284 | H | H | Me | 285 | H | OMe | H |
| 286 | H | CF₃ | H | 287 | H | H | OMe |
| 288 | H | H | CF₃ | 289 | CO₂Me | H | H. |

TABLE 8
Compounds 290-319.
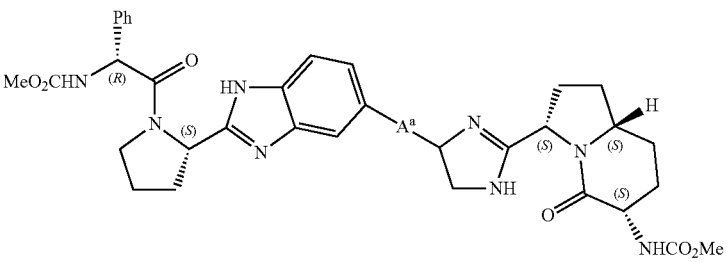
| Entry | $A^a$ | Entry | $A^a$ |
|---|---|---|---|
| 290 | 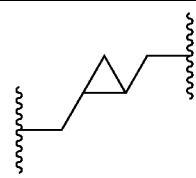 | 291 | 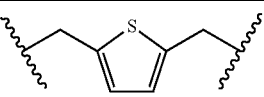 |
| 292 | 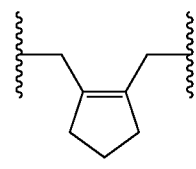 [SMILES: *CC1=C(C*)CCC1] | 293 | 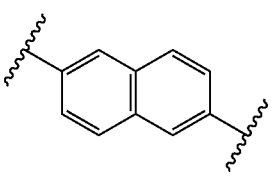 [SMILES: *c1ccc2cc(*)ccc2c1] |
| 294 | 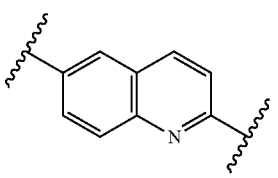 [SMILES: *c1ccc2nc(*)ccc2c1] | 295 | 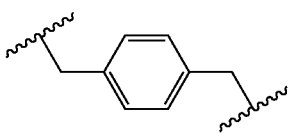 [SMILES: *Cc1ccc(C*)cc1] |
| 296 | 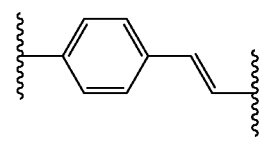 [SMILES: */C=C/c1ccc(*)cc1] | 297 | 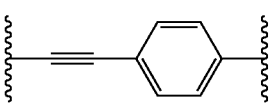 |
| 298 | 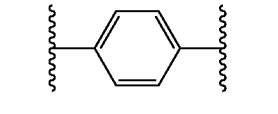 | 299 | 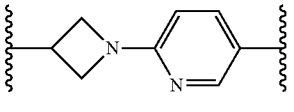 [SMILES: *c1ccc(N2CC(*)C2)nc1] |
| 300 | 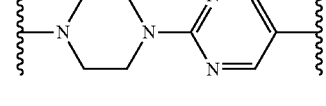 | 301 | 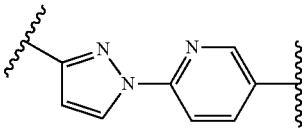 [SMILES: *c1ccc(-n2ccc(*)n2)nc1] |
| 302 | 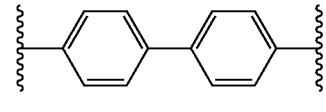 [SMILES: *c1ccc(-c2ccc(*)cc2)cc1] | 303 | 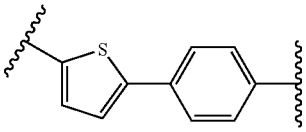 [SMILES: *c1ccc(-c2ccc(*)s2)cc1] |
| 304 | 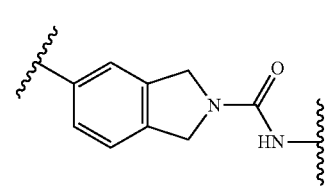 [SMILES: *NC(=O)N1Cc2ccc(*)cc2C1] | 305 | 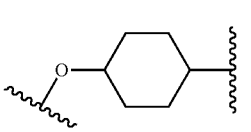 [SMILES: *OC1CCC(*)CC1] |

TABLE 8-continued
Compounds 290-319.
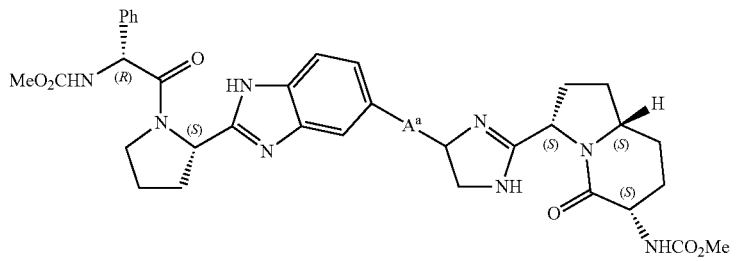
| Entry | $A^a$ | Entry | $A^a$ |
|---|---|---|---|
| 306 | piperidine-N,4-O linker | 307 | 1,4-phenylene-O linker |
| 308 | trans-cyclohexane-1,4-diyl | 309 | 4-methylene-phenylene |
| 310 | CH2-piperazine-N linker | 311 | 1,4-phenylene-di-O linker |
| 312 | trans-CH=CH-C6H4-O linker | 313 | 1,4-phenylene-di-O linker (stereo) |
| 314 | CH=CH-naphthalene-2,6-diyl | 315 | pyridine-2,5-diyl |
| 316 | indole-N,5-diyl | 317 | CH2-thiazole-2,5-diyl |
| 318 | naphthalene-2,6-diyl-C≡C | 319 | piperazine-N,N'-oxazole-2,5-diyl |

TABLE 9
Compounds 320-343.
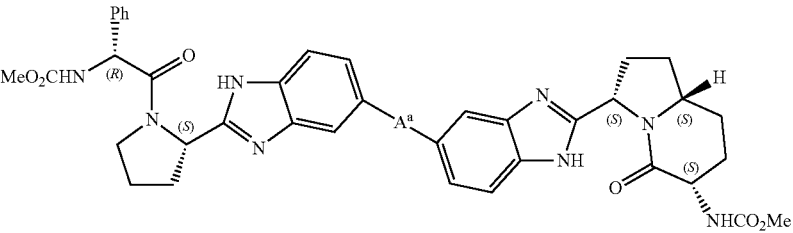
| Entry | A^a | Entry | A^a |
|---|---|---|---|
| 320 | 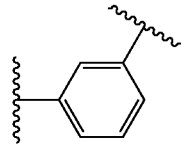 [SMILES: *c1cccc(*)c1] | 321 | 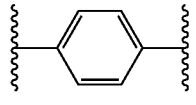 [SMILES: *c1ccc(*)cc1] |
| 322 | 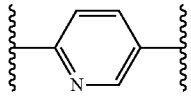 [SMILES: *c1ccc(*)nc1] | 323 | 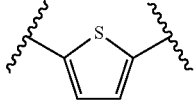 [SMILES: *c1ccc(*)s1] |
| 324 | 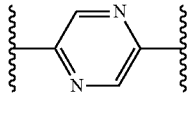 [SMILES: *c1cnc(*)cn1] | 325 | 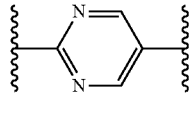 [SMILES: *c1cnc(*)nc1] |
| 326 | 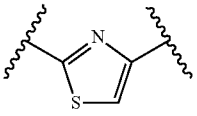 [SMILES: *c1csc(*)n1] | 327 | 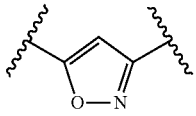 [SMILES: *c1cc(*)on1] |
| 328 | 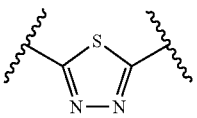 [SMILES: *c1nnc(*)s1] | 329 | 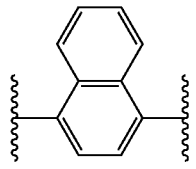 [SMILES: *c1ccc(*)c2ccccc12] |
| 330 | 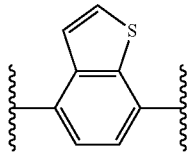 [SMILES: *c1ccc(*)c2sccc12] | 331 | 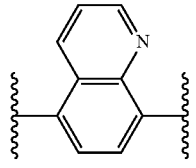 |
| 332 | 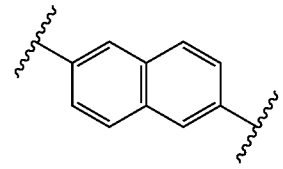 [SMILES: *c1ccc2cc(*)ccc2c1] | 333 | 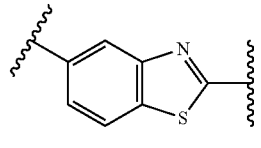 [SMILES: *c1ccc2sc(*)nc2c1] |
| 334 | 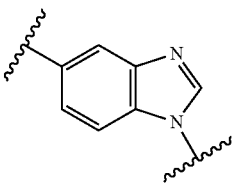 [SMILES: *c1ccc2c(c1)ncn2*] | 335 | 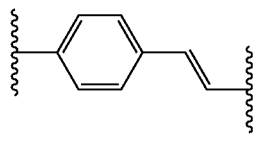 [SMILES: */C=C/c1ccc(*)cc1] |

TABLE 9-continued

Compounds 320-343.

| Entry | A^a | Entry | A^a |
|---|---|---|---|
| 336 | 2,7-naphthalene | 337 | quinoline (3,7) |
| 338 | 2-pyridinone (N,4) | 339 | 2-pyrimidinone (N,4) |
| 340 | coumarin (3,7) | 341 | 1,4-cyclohexylene |
| 342 | 1,4-phenylene-alkyne | 343 | piperazine (N,N) |

TABLE 10

Compounds 344-355.

| Entry | j^j | Entry | j^j |
|---|---|---|---|
| 344 | 1H-pyrazole-3,5-diyl | 345 | 1H-1,2,4-triazole-3,5-diyl |
| 346 | oxazole-2,5-diyl | 347 | 1H-benzimidazole-2,6-diyl |

TABLE 10-continued

Compounds 344-355.

| Entry | $y^j$ | Entry | $y^j$ |
|---|---|---|---|
| 348 | 6-indole-2-yl | 349 | imidazo[4,5-b]pyridine |
| 350 | pyrrolo[3,2-d]pyrimidine | 351 | pyrrolo[2,3-d]pyrimidine |
| 352 | pyrrolo[3,2-b]pyridine | 353 | pyrrolo[2,3-b]pyridine |
| 354 | imidazo[4,5-d]pyrimidine | 355 | indole linked at 6 and 3 |

TABLE 11

Compounds 356-367.

| Entry | $G^g$ | Entry | $G^g$ | Entry | $G^g$ |
|---|---|---|---|---|---|
| 356 | pyrazole | 357 | 1,2,4-triazole | 358 | oxazole |
| 359 | benzimidazole | 360 | indole | 361 | imidazo[4,5-b]pyridine |

TABLE 11-continued
Compounds 356-367.
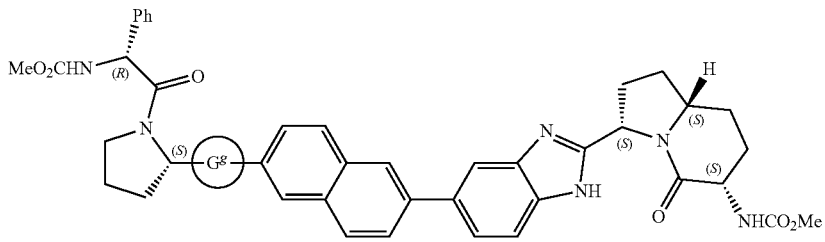
| Entry | G^g | Entry | G^g | Entry | G^g |
|---|---|---|---|---|---|
| 362 | pyrrolo-pyrimidine | 363 | pyrrolo-pyrimidine | 364 | pyrrolo-pyridine |
| 365 | pyrrolo-pyridine | 366 | imidazo-pyrimidine (purine) | 367 | indole |
TABLE 12
Compounds 368-376
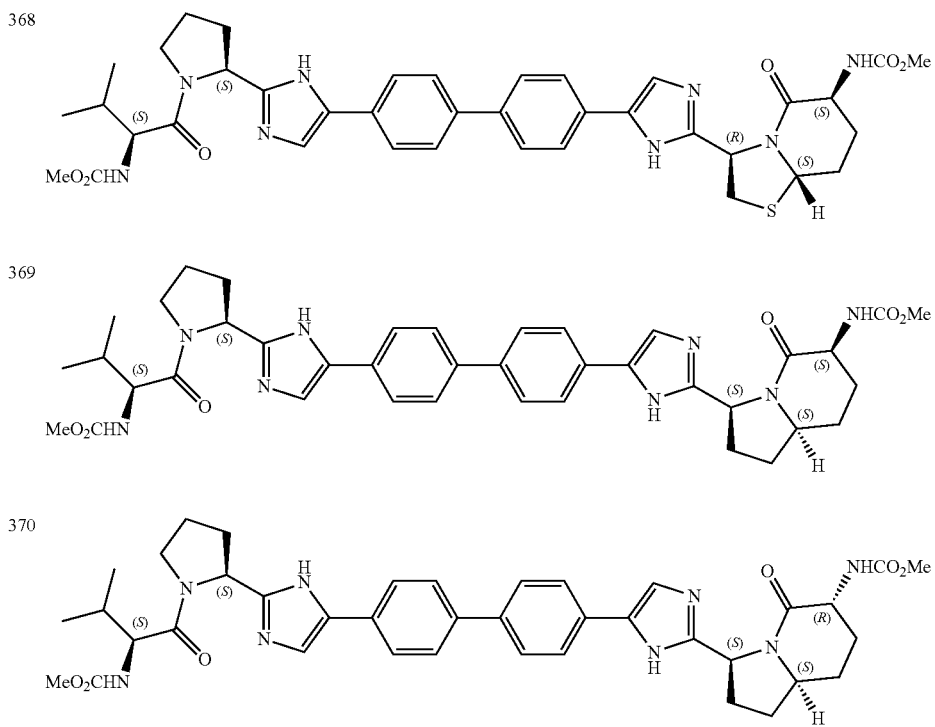

TABLE 12-continued
Compounds 368-376
371 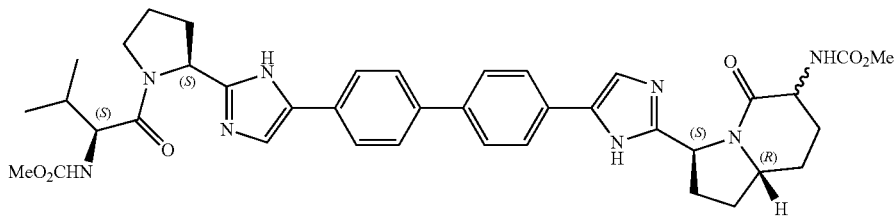
372 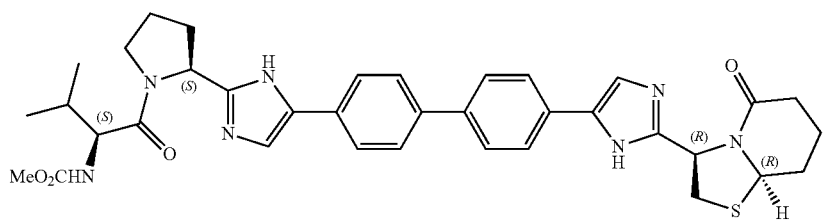
373 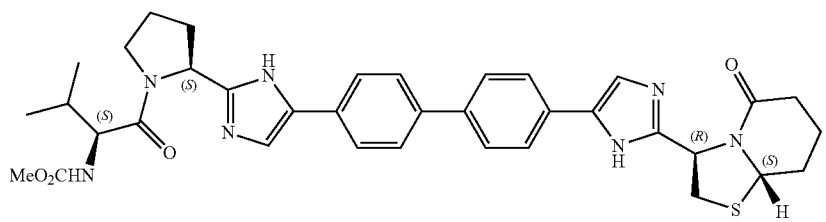
374 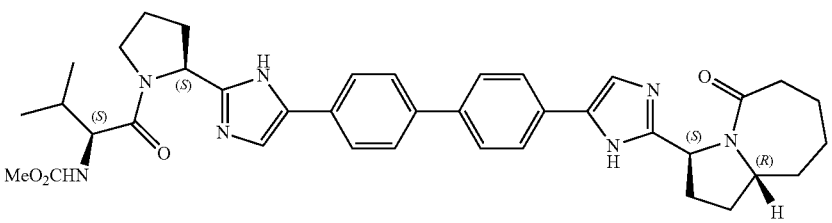
375 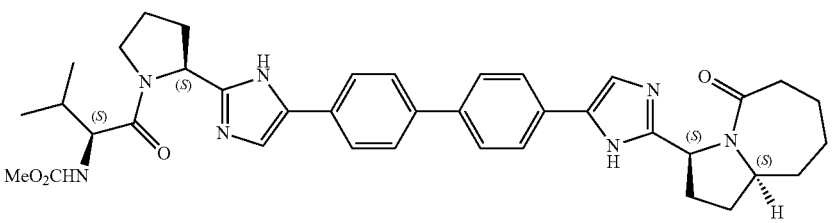
376 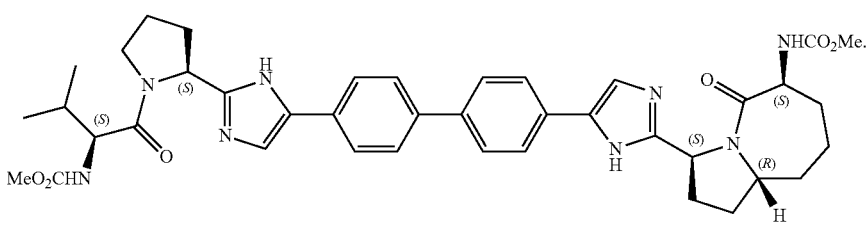

It will be appreciated that the description of the present invention herein should be construed in congruity with the laws and principals of chemical bonding. In some instances it may be necessary to remove a hydrogen atom in order to accommodate a substitutent at any given location.

It is intended that the definition of any substituent or variable (e.g., $R^3$, $R^7$, etc.) at a particular location in a molecule be independent of its definitions elsewhere in that molecule. For example, when U is $C(R^7)_2$, each of the two $R^7$ groups may be the same or different.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

It should be understood that the compounds encompassed by the present invention are those that are suitably stable for use as pharmaceutical agent.

It will be further appreciated that reference herein to therapy and/or treatment includes, but is not limited to prevention, retardation, prophylaxis, therapy and cure of the disease. It will further be appreciated that references herein to treatment or prophylaxis of HCV infection includes treatment or prophylaxis of HCV-associated disease such as liver fibrosis, cirrhosis and hepatocellular carcinoma.

A further embodiment of the present invention includes pharmaceutical compositions comprising any single compound a combination of two or more compounds delineated herein, or a pharmaceutically acceptable salt thereof, with a pharmaceutically acceptable carrier or excipient.

Yet a further embodiment of the present invention is a pharmaceutical composition comprising any single compound or a combination of two or more compounds delineated herein, or a pharmaceutically acceptable salt thereof, in combination with one or more agents known in the art, with a pharmaceutically acceptable carrier or excipient.

It will be further appreciated that compounds of the present invention can be administered as the sole active pharmaceutical agent, or used in combination with one or more agents to treat or prevent hepatitis C infections or the symptoms associated with HCV infection. Other agents to be administered in combination with a compound or combination of compounds of the present invention include therapies for disease caused by HCV infection that suppresses HCV viral replication by direct or indirect mechanisms. These agents include, but not limited to, host immune modulators (for example, interferon-alpha, pegylated interferon-alpha, consensus interferon, interferon-beta, interferon-gamma, CpG oligonucleotides and the like); antiviral compounds that inhibit host cellular functions such as inosine monophosphate dehydrogenase (for example, ribavirin and the like); cytokines that modulate immune function (for example, interleukin 2, interleukin 6, and interleukin 12); a compound that enhances the development of type 1 helper T cell response; interfering RNA; antisense RNA; vaccines comprising HCV antigens or antigen adjuvant combinations directed against HCV; agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7 and the like; and any agent or combination of agents that inhibit the replication of HCV by targeting other proteins of the viral genome involved in the viral replication and/or interfere with the function of other viral targets, such as inhibitors of NS3/NS4A protease, NS3 helicase, NS5B polymerase, NS4A protein and NS5A protein.

According to yet another embodiment, the pharmaceutical compositions of the present invention may further comprise other inhibitor(s) of targets in the HCV life cycle, including, but not limited to, helicase, polymerase, metalloprotease, NS4A protein, NS5A protein, and internal ribosome entry site (IRES).

Accordingly, one embodiment of the present invention is directed to a method for treating or preventing an infection caused by an RNA-containing virus comprising co-administering to a patient in need of such treatment one or more agents selected from the group consisting of a host immune modulator and a second or more antiviral agents, or a combination thereof, with a therapeutically effective amount of a compound or combination of compounds of the present invention, or a pharmaceutically acceptable salt thereof. Examples of the host immune modulator are, but not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome. Example of the RNA-containing virus includes, but not limited to, hepatitis C virus (HCV).

A further embodiment of the present invention is directed to a method of treating or preventing infection caused by an RNA-containing virus comprising co-administering to a patient in need of such treatment an agent or combination of agents that treat or alleviate symptoms of HCV infection including cirrhosis and inflammation of the liver, with a therapeutically effective amount of a compound or combination of compounds of the present invention, or a pharmaceutically acceptable salt thereof. An example of the RNA-containing virus includes, but not limited to, hepatitis C virus (HCV).

Yet another embodiment of the present invention provides a method of treating or preventing infection caused by an RNA-containing virus comprising co-administering to a patient in need of such treatment one or more agents that treat patients for disease caused by hepatitis B (HBV) infection, with a therapeutically effective amount of a compound or a combination of compounds of the present invention, or a pharmaceutically acceptable salt thereof. An agent that treats patients for disease caused by hepatitis B (HBV) infection may be for example, but not limited thereto, L-deoxythymidine, adefovir, lamivudine or tenofovir, or any combination thereof. Example of the RNA-containing virus includes, but not limited to, hepatitis C virus (HCV).

A further embodiment of the present invention provides a method of treating or preventing infection caused by an RNA-containing virus comprising co-administering to a patient in need of such treatment one or more agents that treat patients for disease caused by human immunodeficiency virus (HIV) infection, with a therapeutically effective amount of a compound or a combination of compounds of the present invention, or a pharmaceutically acceptable salt thereof. The agent that treats patients for disease caused by human immunodeficiency virus (HIV) infection may include, but is not limited to, ritonavir, lopinavir, indinavir, nelfinavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide (T-20) or T-1249, or any combination thereof. Example of the RNA-containing virus includes, but not limited to, hepatitis C virus (HCV).

It can occur that a patient may be co-infected with hepatitis C virus and one or more other viruses, including but not limited to human immunodeficiency virus (HIV), hepatitis A virus (HAV) and hepatitis B virus (HBV). Thus also contemplated is combination therapy to treat such co-infections by co-administering a compound according to the present invention with at least one of an HIV inhibitor, an HAV inhibitor and an HBV inhibitor.

In addition, the present invention provides the use of a compound or a combination of compounds of the invention, or a therapeutically acceptable salt thereof, and one or more agents selected from the group consisting of a host immune modulator and a second or more antiviral agents, or a combination thereof, to prepare a medicament for the treatment of an infection caused by an RNA-containing virus in a patient, particularly hepatitis C virus. Examples of the host immune modulator include, but are not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome.

When used in the above or other treatments, combination of compound or compounds of the present invention, together with one or more agents as defined herein above, can be employed in pure form or, where such forms exist, in pharmaceutically acceptable salt thereof. Alternatively, such combination of therapeutic agents can be administered as a pharmaceutical composition containing a therapeutically effective amount of the compound or combination of compounds of interest, or their pharmaceutically acceptable salt thereof, in combination with one or more agents as defined hereinabove, and a pharmaceutically acceptable carrier. Such pharmaceutical compositions can be used for inhibiting the replication of an RNA-containing virus, particularly Hepatitis C virus (HCV), by contacting said virus with said pharmaceutical composition. In addition, such compositions are useful for the treatment or prevention of an infection caused by an RNA-containing virus, particularly Hepatitis C virus (HCV).

Hence, a still further embodiment of the invention is directed to a method of treating or preventing infection caused by an RNA-containing virus, particularly a hepatitis C virus (HCV), comprising administering to a patient in need of such treatment a pharmaceutical composition comprising a compound or combination of compounds of the invention or a pharmaceutically acceptable salt thereof, and one or more agents as defined hereinabove, with a pharmaceutically acceptable carrier.

When administered as a combination, the therapeutic agents can be formulated as separate compositions which are given at the same time or within a predetermined period of time, or the therapeutic agents can be given as a single unit dosage form.

Antiviral agents contemplated for use in such combination therapy include agents (compounds or biologicals) that are effective to inhibit the formation and/or replication of a virus in a mammal, including but not limited to agents that interfere with either host or viral mechanisms necessary for the formation and/or replication of a virus in a mammal. Such agents can be selected from another anti-HCV agent; an HIV inhibitor; an HAV inhibitor; and an HBV inhibitor.

Other agents to be administered in combination with a compound of the present invention include a cytochrome P450 monooxygenase inhibitor, which is expected to inhibit metabolism of the compounds of the invention. Therefore, the cytochrome P450 monooxygenase inhibitor would be in an amount effective to inhibit metabolism of the compounds of this invention. Accordingly, the CYP inhibitor is administered in an amount such that the bioavailiablity of the protease inhibitor is increased in comparison to the bioavailability in the absence of the CYP inhibitor.

In one embodiment, the invention provides methods for improving the pharmaco-kinetics of compounds of the invention. The advantages of improving the pharmacokinetics of drugs are recognized in the art (see, for example, U.S. Publication App. No's. US 2004/0152625 and US 2004/0091527). Accordingly, one embodiment of this invention provides a method comprising administering an inhibitor of CYP3A4 and a compound of the invention. Another embodiment of this invention provides a method comprising administering a compound of the invention and an inhibitor of isozyme 3A4 ("CYP3A4"), isozyme 2C19 ("CYP2C19"), isozyme 2D6 ("CYP2D6"), isozyme 1A2 ("CYP1A2"), isozyme 2C9 ("CYP2C9"), or isozyme 2E1 ("CYP2E1"). In a preferred embodiment, the CYP inhibitor preferably inhibits CYP3A4. Any CYP inhibitor that improves the pharmacokinetics of the relevant compound of the invention may be used in a method of this invention. These CYP inhibitors include, but are not limited to, ritonavir (see, for example, WO 94/14436), ketoconazole, troleandomycin, 4-methyl pyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, ditiazem, erythromycin, VX-944, and VX-497. Preferred CYP inhibitors include ritonavir, ketoconazole, troleandomycin, 4-methylpyrazole, cyclosporin, and clomethiazole.

It will be understood that the administration of the combination of the invention by means of a single patient pack, or patient packs of each formulation, containing within a package insert instructing the patient to the correct use of the invention is a desirable additional feature of this invention.

According to a further aspect of the invention, is a pack comprising at least a compound of the invention and a CYP inhibitor of the invention and an information insert containing directions on the use of the combination of the invention. In an alternative embodiment of this invention, the pharmaceutical pack further comprises one or more of additional agent as described herein. The additional agent or agents may be provided in the same pack or in separate packs.

Another aspect of this involves a packaged kit for a patient to use in the treatment of HCV infection or in the prevention of HCV infection, comprising: a single or a plurality of pharmaceutical formulation of each pharmaceutical component; a container housing the pharmaceutical formulation (s) during storage and prior to administration; and instructions for carrying out drug administration in a manner effective to treat or prevent HCV infection.

Accordingly, this invention provides kits for the simultaneous or sequential administration of a compound of the invention and a CYP inhibitor (and optionally an additional agent) or derivatives thereof are prepared in a conventional manner. Typically, such a kit will comprise, e.g. a composition of each inhibitor and optionally the additional agent (s) in a pharmaceutically acceptable carrier (and in one or in a plurality of pharmaceutical formulations) and written instructions for the simultaneous or sequential administration.

In another embodiment, a packaged kit is provided that contains one or more dosage forms for self administration; a container means, preferably sealed, for housing the dosage forms during storage and prior to use; and instructions for a patient to carry out drug administration. The instructions will typically be written instructions on a package insert, a label, and/or on other components of the kit, and the dosage form or forms are as described herein. Each dosage form may be individually housed, as in a sheet of a metal foil-plastic laminate with each dosage form isolated from the others in individual cells or bubbles, or the dosage forms may be housed in a single container, as in a plastic bottle. The present kits will also typically include means for packaging the individual kit components, i.e., the dosage forms, the container means, and the written instructions for use. Such packaging means may take the form of a cardboard or paper box, a plastic or foil pouch, etc.

DEFINITIONS

Listed below are definitions of various terms used to describe this invention. These definitions apply to the terms as they are used throughout this specification and claims, unless otherwise limited in specific instances, either individually or as part of a larger group.

The term "viral infection" refers to the introduction of a virus into cells or tissues, e.g., hepatitis C virus (HCV). In general, the introduction of a virus is also associated with replication. Viral infection may be determined by measuring virus antibody titer in samples of a biological fluid, such as blood, using, e.g., enzyme immunoassay. Other suitable diagnostic methods include molecular based techniques, such as RT-PCR, direct hybrid capture assay, nucleic acid sequence based amplification, and the like. A virus may infect an organ, e.g., liver, and cause disease, e.g., hepatitis, cirrhosis, chronic liver disease and hepatocellular carcinoma.

The term "immune modulator" refers to any substance meant to alter the working of the humoral or cellular immune system of a subject. Such immune modulators include inhibitors of mast cell-mediated inflammation, interferons, interleukins, prostaglandins, steroids, cortico-steroids, colony-stimulating factors, chemotactic factors, etc.

The term "aryl," as used herein, refers to a mono- or polycyclic carbocyclic ring system including, but not limited to, phenyl, naphthyl, tetrahydronaphthyl, indanyl, idenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic ring system comprising at least one aromatic ring having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl. A polycyclic heteroaryl can comprise fused rings, covalently attached rings or a combination thereof.

In accordance with the invention, aromatic groups can be substituted or unsubstituted.

The term "bicyclic aryl" or "bicyclic heteroaryl" refers to a ring system consisting of two rings wherein at least one ring is aromatic; and they can be fused or covalently attached.

The term "tricyclic aryl" or "tricyclic heteroaryl" refers to a ring system consisting of three rings wherein at least one ring is aromatic.

The terms "$C_1$-$C_4$ alkyl," "$C_1$-$C_6$ alkyl," "$C_1$-$C_8$ alkyl," "$C_2$-$C_4$ alkyl," or "$C_3$-$C_6$ alkyl," as used herein, refer to saturated, straight- or branched-chain hydrocarbon radicals containing between one and four, one and six, one and eight carbon atoms, or the like, respectively. Examples of $C_1$-$C_8$ alkyl radicals include, but are not limited to, methyl, ethyl, propyl, isopropyl, n-butyl, tent-butyl, neopentyl, n-hexyl, heptyl and octyl radicals.

The terms "$C_2$-$C_8$ alkenyl," "$C_2$-$C_4$ alkenyl," "$C_3$-$C_4$ alkenyl," or "$C_3$-$C_6$ alkenyl," as used herein, refer to straight- or branched-chain hydrocarbon radicals containing from two to eight, or two to four carbon atoms, or the like, having at least one carbon-carbon double bond by the removal of a single hydrogen atom. Alkenyl groups include, but are not limited to, for example, ethenyl, propenyl, butenyl, 1-methyl-2-buten-1-yl, heptenyl, octenyl, and the like.

The terms "$C_2$-$C_8$ alkynyl," "$C_2$-$C_4$ alkynyl," "$C_3$-$C_4$ alkynyl," or "$C_3$-$C_6$ alkynyl," as used herein, refer to straight- or branched-chain hydrocarbon radicals containing from two to eight, or two to four carbon atoms, or the like, having at least one carbon-carbon triple bond by the removal of a single hydrogen atom. Representative alkynyl groups include, but are not limited to, for example, ethynyl, 1-propynyl, 1-butynyl, heptynyl, octynyl, and the like.

The term "$C_3$-$C_8$-cycloalkyl", or "$C_5$-$C_7$-cycloalkyl," as used herein, refers to a monocyclic or polycyclic saturated carbocyclic ring compound, and the carbon atoms may be optionally oxo-substituted. Examples of $C_3$-$C_8$-cycloalkyl include, but not limited to, cyclopropyl, cyclobutyl, cyclopentyl, cyclohexyl, cyclopentyl and cyclooctyl; and examples of $C_5$-$C_7$-cycloalkyl include, but not limited to, cyclopentyl, cyclohexyl, bicyclo[2.2.1]heptyl, and the like.

The term "$C_3$-$C_8$ cycloalkenyl", or "$C_5$-$C_7$ cycloalkenyl" as used herein, refers to monocyclic or polycyclic carbocyclic ring compound having at least one carbon-carbon double bond, and the carbon atoms may be optionally oxo-substituted. Examples of $C_3$-$C_8$ cycloalkenyl include, but not limited to, cyclopropenyl, cyclobutenyl, cyclopentenyl, cyclohexenyl, cycloheptenyl, cyclooctenyl, and the like; and examples of $C_5$-$C_7$ cycloalkenyl include, but not limited to, cyclopentenyl, cyclohexenyl, cycloheptenyl, and the like.

The term "arylalkyl", as used herein, refers to an aryl-substituted alkyl group. More preferred arylalkyl groups are aryl-$C_1$-$C_6$-alkyl groups.

The term "heteroarylalkyl", as used herein, refers to a heteroaryl-substituted alkyl group. More preferred heteroarylalkyl groups are heteroaryl-$C_1$-$C_6$-alkyl groups.

It is understood that any alkyl, alkenyl, alkynyl, cycloalkyl and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as, O, OH, NH, $NH_2$, C(O), $S(O)_2$, C(O)O, C(O)NH, OC(O)O, OC(O)NH, $OC(O)NH_2$, $S(O)_2NH$, $S(O)_2NH_2$, $NHC(O)NH_2$, NHC(O)C(O)NH, $NHS(O)_2NH$, $NHS(O)_2NH_2$, $C(O)NHS(O)_2$, $C(O)NHS(O)_2NH$ or $C(O)NHS(O)_2NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched or cyclic and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted. A linear aliphatic group is a non-cyclic aliphatic group. It is to be understood that when an aliphatic group or a linear aliphatic group is said to "contain" or "include" or "comprise" one or more specified functional groups, the linear aliphatic group can, for example, be selected from one or more of the specified functional groups or a combination thereof, or a group wherein one or more carbons of a non-aromatic hydrocarbon (optionally substituted) is replaced by a specified functional group. In some examples, the aliphatic group can be represented by the formula $M_x$-V-$M_x'$, where $M_x$ and $M_x'$ are each independently absent or an alkyl, alkenyl or alkynyl, each optionally substituted, and V is a functional group. In some examples, V is selected from the group consisting of C(O), S(O)$_2$, C(O)O, C(O)N($R^{11}$), OC(O)O, OC(O)N($R^{11}$), S(O)$_2$N($R^{11}$), N($R^{11}$)C(O)N($R^{11}$), N($R^{11}$)C(O)C(O)N($R^{11}$), N($R^{11}$)S(O)$_2$N($R^{11}$), C(O)N($R^{11}$)S(O)$_2$ or C(O)N($R^{11}$)S(O)$_2$N($R^{11}$); wherein $R^{11}$ is as previously defined. In another aspect of the invention, an exemplary linear aliphatic group is an alkyl, alkenyl or alkynyl, each optionally substituted, which is interrupted or terminated by a functional group such as described herein.

The term "alicyclic," as used herein, denotes a monovalent group derived from a monocyclic or bicyclic saturated carbocyclic ring compound by the removal of a single hydrogen atom, and the carbon atoms may be optionally oxo-substituted. Examples include, but not limited to, cyclopropyl, cyclobutyl, cyclopentyl, cyclohexyl, bicyclo[2.2.1]heptyl, and bicyclo[2.2.2]octyl. Such alicyclic groups may be further substituted.

The terms "heterocyclic" or "heterocycloalkyl" can be used interchangeably and referred to a non-aromatic ring or a bi- or tri-cyclic group fused system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent group when used as a linkage to connect two groups or substituents, which can be at the same or different atom(s).

The term "substituted" when used with alkyl, alkenyl, alkynyl, alicyclic, cycloalkyl, cycloalkenyl, aryl, heteroaryl, heterocyclic, or aliphatic as described herein refers to substitution by independent replacement of one, two, or three or more of the hydrogen atoms thereon with substituents including, but not limited to, —F, —Cl, —Br, —I, —OH, protected hydroxy, —NO$_2$, —N$_3$, —CN, —NH$_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, —CONH$_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —OCO$_2$—$C_1$-$C_{12}$-alkyl, —OCO$_2$—$C_2$-$C_8$-alkenyl, —OCO$_2$—$C_2$-$C_8$-alkynyl, —OCO$_2$—$C_3$-$C_{12}$-cycloalkyl, —OCO$_2$-aryl, —OCO$_2$-heteroaryl, —OCO$_2$-heterocycloalkyl, —CO$_2$—$C_1$-$C_{12}$ alkyl, —CO$_2$—$C_2$-$C_8$ alkenyl, —CO$_2$—$C_2$-$C_8$ alkynyl, CO$_2$—$C_3$-$C_{12}$-cycloalkyl, —CO$_2$-aryl, CO$_2$-heteroaryl, CO$_2$-heterocloalkyl, —OCONH$_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocycloalkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocycloalkyl, —NHCO$_2$—$C_1$-$C_{12}$-alkyl, —NHCO$_2$—$C_2$-$C_8$-alkenyl, —NHCO$_2$—$C_2$-$C_8$-alkynyl, —NHCO$_2$—$C_3$-$C_{12}$-cycloalkyl, —NHCO$_2$-aryl, —NHCO$_2$-heteroaryl, —NHCO$_2$-heterocycloalkyl, —NHC(O)NH$_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)NH$_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —SO$_2$NH$_2$, —SO$_2$NH—$C_1$-$C_{12}$-alkyl, —SO$_2$NH—$C_2$-$C_8$-alkenyl, —SO$_2$NH—$C_2$-$C_8$-alkynyl, —SO$_2$NH—$C_3$-$C_{12}$-cycloalkyl, —SO$_2$NH-aryl, —SO$_2$NH-heteroaryl, —SO$_2$NH-heterocycloalkyl, —NHSO$_2$—$C_1$-$C_{12}$-alkyl, —NHSO$_2$—$C_2$-$C_8$-alkenyl, —NHSO$_2$—$C_2$-$C_8$-alkynyl, —NHSO$_2$—$C_3$-$C_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthiomethyl. It is understood that the aryls, heteroaryls, alkyls, and the like can be further substituted.

The term "halogen," as used herein, refers to an atom selected from fluorine, chlorine, bromine and iodine.

The term "hydrogen" includes hydrogen and deuterium. In addition, the recitation of an atom includes other isotopes of that atom so long as the resulting compound is pharmaceutically acceptable.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis*, 3rd edition, John Wiley & Sons, New York (1999). Examples of hydroxyl protecting groups include benzyloxycarbonyl, 4-methoxybenzyloxycarbonyl, tert-butoxycarbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenylmethyl (trityl), methoxymethyl, methylthiomethyl, benzyloxymethyl, 2-(trimethylsilyl)ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "carbonyl protecting group," as used herein, refers to a labile chemical moiety which is known in the art to protect a carbonyl group against undesired reactions during synthetic procedures. After said synthetic procedure(s) the carbonyl protecting group as described herein may be selectively removed. Carbonyl protecting groups as known in the art are described generally in T. H. Greene and P. G. M. Wuts, *Protective Groups in Organic Synthesis*, 3rd edition, John Wiley & Sons, New York (1999). Examples of carbonyl protecting groups include acetals, ketals, cyclic acetals, cyclic ketals, mono- or dithioacetals, mono- or dithioketals, optionally substituted hydrazones or oximes.

The term "protected carbonyl," as used herein, refers to a carbonyl group protected with a carbonyl protecting group, as defined above, including dimethyl acetal, 1,3-dioxolane, 1,3-dioxane, S,S'-dimethylketal, 1,3-dithiane, 1,3-dithiolane, 1,3-oxathiolane, N,N-dimethylhydrazone, oxime, for example.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis*, 3rd edition, John Wiley & Sons, New York (1999). Examples of amino protecting groups include, but are not limited to, methoxycarbonyl, t-butoxycarbonyl, 9-fluorenylmethoxycarbonyl, benzyloxycarbonyl, and the like.

The term "protected amino," as used herein, refers to an amino group protected with an amino protecting group as defined above.

The term "substituted amino," as used herein, refers to substitution by replacement of one or two hydrogen atoms of —NH$_2$ with substituents independently selected from the group consisting of optionally substituted alkyl, optionally substituted alkenyl, optionally substituted alkynyl, optionally substituted aryl, optionally substituted cycloalkyl, optionally substituted heteroaryl, and optionally substituted heterocyclic; alternatively, when disubstituted, the two substitutents can be optionally taken together with the nitrogen atom to which they are attached to form an optionally substituted heterocyclic group.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; hydroxy; imidazolyl; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

The term "protic solvent' as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, 2$^{nd}$ Ed. Wiley-VCH (1999); T. W. Greene and P. G. M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994);

and L. Paquette, ed., *Encyclopedia of Reagents for Organic Synthesis*, John Wiley and Sons (1995), and subsequent editions thereof.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., *Journal of Drug Deliver Reviews*, 8:1-38 (1992); Bundgaard, *J. of Pharmaceutical Sciences*, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

The present invention also relates to solvates of the compounds of Formula (I), for example hydrates.

This invention also encompasses pharmaceutical compositions containing, and methods of treating viral infections through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

Antiviral Activity

An inhibitory amount or dose of the compounds of the present invention may range from about 0.01 mg/Kg to about 500 mg/Kg, alternatively from about 1 to about 50 mg/Kg Inhibitory amounts or doses will also vary depending on route of administration, as well as the possibility of co-usage with other agents.

According to the methods of treatment of the present invention, viral infections, conditions are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the present invention described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the invention and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The said "additional therapeutic or prophylactic agents" include, but are not limited to, immune therapies (eg. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (eg N-acetylcysteine), cytokine agonists, cytokine antagonists, lung surfactants and/or antimicrobial and anti-viral agents (eg ribavirin and amantidine). The compositions according to the invention may also be used in combination with gene replacement therapy.

Combination and Alternation Therapy for HCV

It has been recognized that drug-resistant variants of HCV can emerge after prolonged treatment with an antiviral agent. Drug resistance most typically occurs by mutation of a gene that encodes for a protein such as an enzyme used in viral replication, and most typically in the case of HCV, RNA polymerase, protease, or helicase.

Recently, it has been demonstrated that the efficacy of a drug against a viral infection, such as HIV, can be prolonged, augmented, or restored by administering the drug in combination or alternation with a second, and perhaps third, antiviral compound that induces a different mutation from that caused by the principal drug. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

A compound of the present invention can also be administered in combination or alternation with antiviral agent. Exemplary antiviral agents include ribavarin, interferon, interleukin or a stabilized prodrug of any of them. More broadly described, the compound can be administered in combination or alternation with any of the anti-HCV drugs listed in Table 13 below.

TABLE 13

Table of anti-Hepatitis C Compounds in Current Clinical Development

| Drug name | Drug category | Pharmaceutical Company |
| --- | --- | --- |
| PEGASYS pegylated interferon alfa-2a | Long acting interferon | Roche |
| INFERGEN interferon alfacon-1 | Long acting interferon | InterMune |
| OMNIFERON natural interferon | Long acting interferon | Viragen |
| ALBUFERON | Long acting interferon | Human Genome Sciences |
| REBIF interferon beta-1a | Interferon | Ares-Serono |
| Omega Interferon | Interferon | BioMedicine |
| Oral Interferon alpha | Oral Interferon | Amarillo Biosciences |
| Interferon gamma-1b | Anti-fibrotic | InterMune |
| IP-501 | Anti-fibrotic | InterMune |
| Merimebodib VX-497 | IMPDH inhibitor (inosine monophosphate dehydrogenase) | Vertex |
| AMANTADINE (Symmetrel) | Broad Antiviral Agent | Endo Labs Solvay |
| IDN-6556 | Apotosis regulation | Idun Pharma. |
| XTL-002 | Monclonal Antibody | XTL |
| HCV/MF59 | Vaccine | Chiron |
| CIVACIR | Polyclonal Antibody | NABI |
|  | Therapeutic vaccine | Innogenetics |
| VIRAMIDINE | Nucleoside Analogue | ICN |
| ZADAXIN (thymosin alfa-1) | Immunomodulator | Sci Clone |
| CEPLENE (histamine) | Immunomodulator | Maxim |
| VX 950/LY 570310 | Protease inhibitor | Vertex/Eli Lilly |
| ISIS 14803 | Antisense | Isis Pharmaceutical/Elan |
| IDN-6556 | Caspase inhibitor | Idun Pharmaceuticals |
| JTK 003 | Polymerase Inhibitor | AKROS Pharma |
| Tarvacin | Anti-Phospholipid Therapy | Peregrine |
| HCV-796 | Polymerase Inhibitor | ViroPharma/Wyeth |
| CH-6 | Protease inhibitor | Schering |
| ANA971 | Isatoribine | ANADYS |
| ANA245 | Isatoribine | ANADYS |
| CPG 10101 (Actilon) | Immunomodulator | Coley |
| Rituximab (Rituxam) | Anti-CD2O Monoclonal Antibody | Genetech/IDEC |
| NM283 (Valopicitabine) | Polymerase Inhibitor | Idenix Pharmaceuticals |
| HepX ™-C | Monoclonal Antibody | XTL |
| IC41 | Therapeutic Vaccine | Intercell |
| Medusa Interferon | Longer acting interferon | Flamel Technology |
| E-1 | Therapeutic Vaccine | Innogenetics |
| Multiferon | Long Acting Interferon | Viragen |
| BILN 2061 | Protease inhibitor | Boehringer-Ingelheim |
| TMC435350 | Protease inhibitor | Tibotec/Medivir |
| Telaprevir (VX-950) | Protease inhibitor | Vertex |
| Boceprevir (SCH 503034) | Protease inhibitor | Schering-Plough |
| ACH-1625 | Protease inhibitor | Achillion |
| ABT-450 | Protease inhibitor | Abbott/Enanta |
| BI-201335 | Protease inhibitor | Boehringer-Ingelheim |
| PHX-1766 | Protease inhibitor | Phenomix |
| VX-500 | Protease inhibitor | Vertex |
| MK-7009 | protease inhibitor | Merck |
| R7227 (ITMN-191) | protease inhibitor | InterMune |

TABLE 13-continued

Table of anti-Hepatitis C Compounds
in Current Clinical Development

| Drug name | Drug category | Pharmaceutical Company |
|---|---|---|
| Narlaprevir (SCH 900518) | Protease inhibitor | Schering/Merck |
| Alinia (nitazoxanide) | To be determined | Romark |
| ABT-072 | Polymerase Inhibitor | Abbott |
| ABT-333 | Polymerase Inhibitor | Abbott |
| Filibuvir (PF-00868554) | Polymerase Inhibitor | Pfizer |
| VCH-916 | Polymerase Inhibitor | Vertex |
| R7128 (PSI6130) | Polymerase Inhibitor | Roche/Pharmasset |
| IDX184 | Polymerase Inhibitor | Idenix |
| R1626 | Polymerase Inhibitor | Roche |
| MK-3281 | Polymerase Inhibitor | Merck |
| PSI-7851 | Polymerase Inhibitor | Pharmasset |
| ANA598 | Polymerase inhibitor | Anadys Pharmaceuticals |
| BI-207127 | Polymerase inhibitor | Boehringer-Ingelheim |
| GS-9190 | Polymerase inhibitor | Gilead |
| VCH-759 | Polymerase Inhibitor | Vertex |
| Clemizole | NS4B inhibitor | Eiger Biopharmaceuticals |
| A-832 | NS5A inhibitor | ArrowTherapeutics |
| BMS-790052 | NS5A inhibitor | Bristol-Myers-Squibb |
| ITX5061 | Entry inhibitor | iTherx |
| GS-9450 | Caspase inhibitor | Gilead |
| ANA773 | TLR agonist | Anadys |
| CYT107 | immunomodulator | Cytheris |
| SPC3649 (LNA-antimiR ™-122) | microRNA | Santaris Pharma |
| Debio 025 | Cyclophilin inhibitor | Debiopharm |
| SCY-635 | Cyclophilin inhibitor | Scynexis |

Unless otherwise defined, all technical and scientific terms used herein are accorded the meaning commonly known to one of ordinary skill in the art. All publications, patents, published patent applications, and other references mentioned herein are hereby incorporated by reference in their entirety.

Abbreviations

Abbreviations which may be used in the descriptions of the scheme and the examples that follow are: Ac for acetyl; AcOH for acetic acid; AIBN for azobisisobutyronitrile; BINAP for 2,2'-bis(diphenylphosphino)-1,1'-binaphthyl; $Boc_2O$ for di-tert-butyl-dicarbonate; Boc for t-butoxycarbonyl; Bpoc for 1-methyl-1-(4-biphenylyl)ethyl carbonyl; BtOH for 1-hydroxy-benzotriazole; Bz for benzoyl; Bn for benzyl; BocNHOH for tent-butyl N-hydroxycarbamate; t-BuOK for potassium tert-butoxide; $Bu_3SnH$ for tributyltin hydride; BOP for (benzotriazol-1-yloxy)tris(dimethylamino) phosphonium Hexafluorophosphate; Brine for sodium chloride solution in water; Cbz for carbobenzyloxy; CDI for carbonyldiimidazole; $CH_2Cl_2$ for dichloromethane; $CH_3$ for methyl; $CH_3CN$ for acetonitrile; $Cs_2CO_3$ for cesium carbonate; CuCl for copper (I) chloride; CuI for copper (I) iodide; dba for dibenzylidene acetone; dppb for diphenylphosphino butane; DBU for 1,8-diazabicyclo[5.4.0]undec-7-ene; DCC for N,N'-dicyclohexylcarbodiimide; DEAD for diethylazodicarboxylate; DIAD for diisopropyl azodicarboxylate; DIBAL-H for diisobutylaluminium hydride; DIPEA or (i-Pr)$_2$EtN for N,N-diisopropylethyl amine; Dess-Martin periodinane for 1,1,1-tris(acetyloxy)-1,1-dihydro-1,2-benziodoxol-3-(1H)-one; DMAP for 4-dimethylaminopyridine; DME for 1,2-dimethoxy-ethane; DMF for N,N-dimethylformamide; DMSO for dimethyl sulfoxide; DMT for di(p-methoxyphenyl)phenylmethyl or dimethoxytrityl; DPPA for diphenylphosphoryl azide; EDC for N-(3-dimethylaminopropyl)-N'-ethylcarbodiimide; EDC HCl for N-(3-dimethylamino-propyl)-N'-ethylcarbodiimide hydrochloride; EtOAc for ethyl acetate; EtOH for ethanol; $Et_2O$ for diethyl ether; Fmoc for 9-fluorenylmethoxycarbonyl; Grubbs-1 catalyst for benzylidene-bis(tricyclohexylphosphine)dichlororuthenium; HATU for O-(7-azabenzotriazol-1-yl)-N,N,N',N'-tetramethyluronium hexafluorophosphate; HCl for hydrogen chloride; HOBT for 1-hydroxybenzotriazole; $K_2CO_3$ for potassium carbonate; n-BuLi for n-butyl lithium; i-BuLi for i-butyl lithium; t-BuLi for t-butyl lithium; PhLi for phenyl lithium; LDA for lithium diisopropylamide; LiTMP for lithium 2,2,6,6-tetramethylpiperidinate; MeOH for methanol; Mg for magnesium; MOM for methoxymethyl; Ms for mesyl or —$SO_2$—$CH_3$; $Ms_2O$ for methanesulfonic anhydride or mesyl-anhydride; $NaBH_4$ for sodium borohydride; $NaBH_3CN$ for sodium cyanoborohydride; $NaN(TMS)_2$ for sodium bis(trimethylsilyl)amide; NaCl for sodium chloride; NaH for sodium hydride; $NaHCO_3$ for sodium bicarbonate or sodium hydrogen carbonate; $Na_2CO_3$ sodium carbonate; NaOH for sodium hydroxide; $Na_2SO_4$ for sodium sulfate; $NaHSO_3$ for sodium bisulfite or sodium hydrogen sulfite; $Na_2S_2O_3$ for sodium thiosulfate; $NH_2NH_2$ for hydrazine; $NH_4HCO_3$ for ammonium bicarbonate; $NH_4Cl$ for ammonium chloride; NMMO for N-methylmorpholine N-oxide; $NaIO_4$ for sodium periodate; Ni for nickel; OH for hydroxyl; $OsO_4$ for osmium tetroxide; Pd for palladium; Ph for phenyl; PMB for p-methoxybenzyl; POPd for dihydrogen dichlorobis (di-tert-butylphosphinito-κP)palladate(II); $Pd_2(dba)_3$ for tris (dibenzylidene-acetone) dipalladium (0); $Pd(PPh_3)_4$ for tetrakis(triphenylphosphine)palladium (0); $PdCl_2(PPh_3)_2$ for trans-dichlorobis(triphenyl-phosphine)palladium (II); Pt for platinum; Rh for rhodium; rt for room temperature; Ru for ruthenium; SEM for (trimethylsilyl)ethoxymethyl; TBAF for tetrabutylammonium fluoride; TBS for tent-butyl dimethylsilyl; TEA or $Et_3N$ for triethylamine; Teoc for 2-trimethylsilyl-ethoxy-carbonyl; TFA for trifluoroacetic acid; THF for tetrahydrofuran; TMEDA for N,N,N',N'-tetramethylethylenediamine; TPP or $PPh_3$ for triphenyl-phosphine; Troc for 2,2,2-trichloroethyl carbonyl; Ts for tosyl or —$SO_2$—$C_6H_4CH_3$; $Ts_2O$ for tolylsulfonic anhydride or tosyl-anhydride; TsOH for p-tolylsulfonic acid; TMS for trimethylsilyl; or TMSCl for trimethylsilyl chloride.

Synthetic Methods

The compounds and processes of the present invention will be better understood in connection with the following synthetic schemes that illustrate the methods by which the compounds of the invention may be prepared. Starting materials can be obtained from commercial sources or prepared by well-established literature methods known to those of ordinary skill in the art. It will be readily apparent to one of ordinary skill in the art that the compounds defined above can be synthesized by substitution of the appropriate reactants and agents in the syntheses shown below. It will also be readily apparent to one skilled in the art that the selective protection and deprotection steps, as well as the order of the steps themselves, can be carried out in varying order, depending on the nature of the variables to successfully complete the syntheses below. The variables are as defined above unless otherwise noted below.

The compounds of the present invention may be prepared via several different synthetic routes from a variety of 5/6-membered fused heteroaryl, 5-membered heteroaryl, and related intermediates. A retro-synthesis of those title compounds include direct formation of a suitably linked core structure (5/6-membered fused heteroaryl, 5-membered heteroaryl or a combination thereof) followed by attachment of a suitable capping group (such as —C(O)R$^6$ or —C(O)OR$^{13}$), plus some functional group manipulations in between and/or after. Various 5/6-membered fused heteroaryl or 5-membered heteroaryl intermediates are known to those skilled in the art, for example see the encyclopedic volumes edited by A. R. Katrizky, et al, "Comprehensive Heterocyclic Chemistry" 1984; "Comprehensive Heterocyclic Chemistry II" 1996; "Comprehensive Heterocyclic Chemistry III" 2008.

A general synthesis and further elaboration of some 6-membered ring fused imidazole related intermediates are summarized in Scheme 1, in which Z is N or CH.

The synthesis starts from the construction of an optionally substituted imidazopyridine or benzimidazole 1-2, which may be obtained by condensation of an amino acid or its derivative 1-1.1 or 1-1.2 and a 2,3-diaminopyridine or 1,2-diaminobenzene 1-1 under the conditions to those skilled in the art. The imidazole ring closure may be realized either in one pot by heat, optionally in the presence of an acid and/or with a dehydration reagent such as polyphosphoric acid; or in two steps: 1) amide formation between diamine 1-1 and amino acid 1-1.1 or 1-1.2 in the presence of a condensation reagent such as EDC HCl, DCC or the like; or through mixed anhydride approach by reacting acid 1-1.1 or 1-1.2 with a chloroformate such as methyl chloroformate, isobutyl chloroformate, or the like, in the presence of a base such as TEA, DIPEA, DMAP, N-methylmorpholine, or the like, followed by treating the mixed anhydride with diamine 1-1; and 2) the heterocyclic ring closure in the presence of an acid such as acetic acid, sulfuric acid or the like or a dehydration reagent such as HATU or the like, optionally with heat.

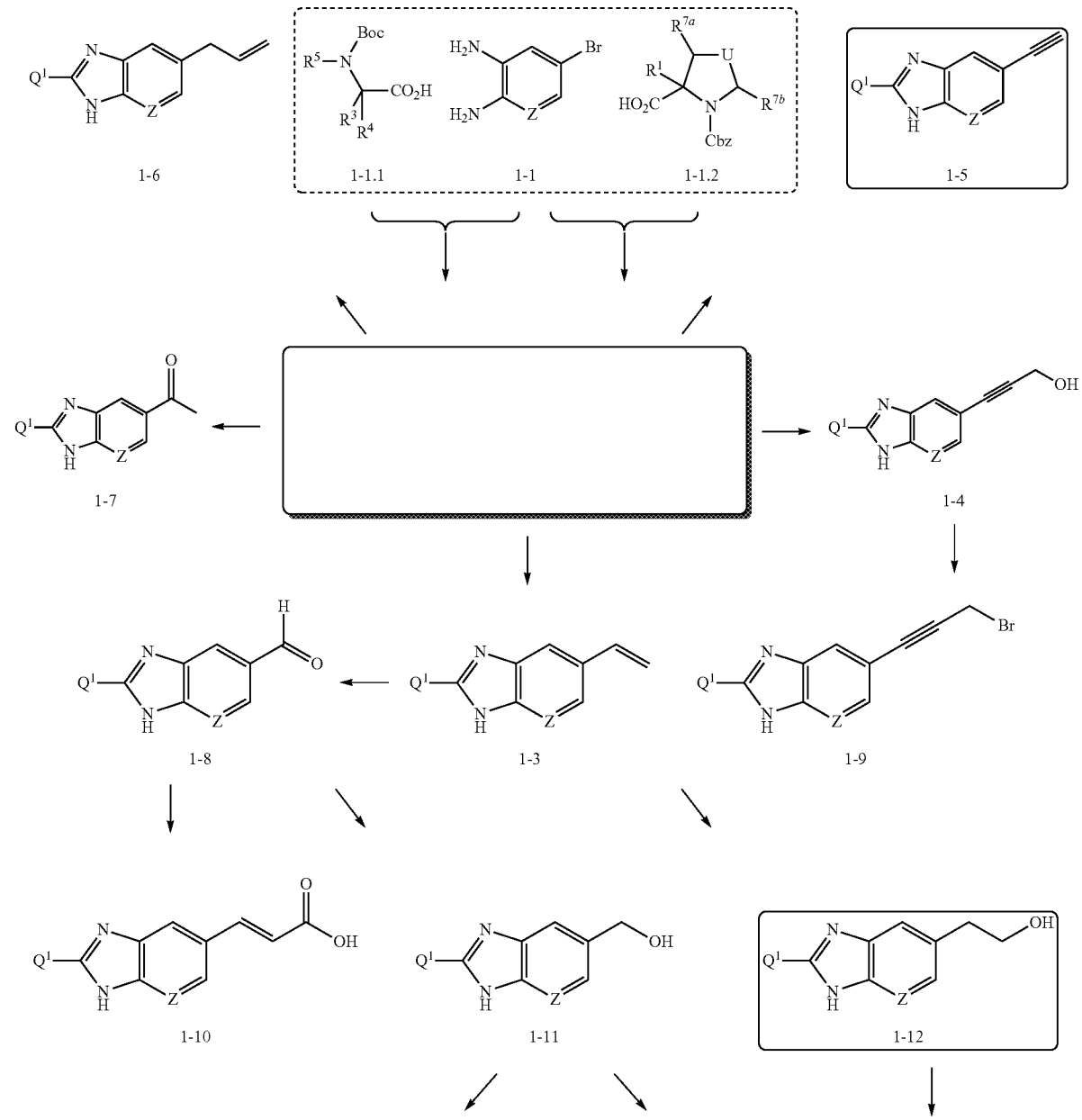

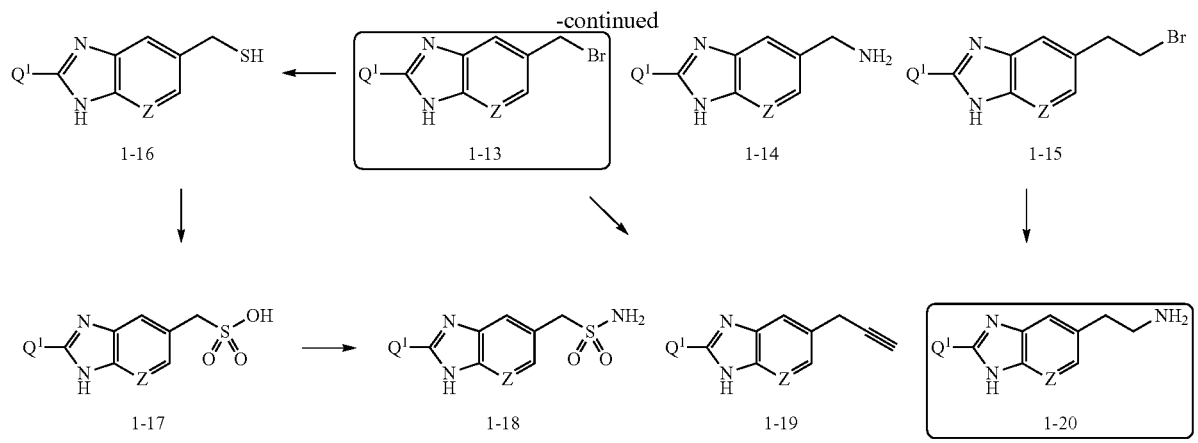

Optionally, the NH group in the newly formed imidazopyridine or benzimidazole ring of 1-2 may be protected with an amino protecting group, such as SEM (i.e. SEM-Cl, NaH), Boc, Cbz, Teoc, Troc, or the like. The protected imidazopyridine or benzimidazole 1-2 may be subjected to lithium-halogen exchange with various (n-, s-, or t-) butyl lithium and the resulting lithiate can be trapped with a nucleophile, i.e. a halide such as various allyl halide to give the allylated 1-6 as a key intermediate. Alternatively, 1-6 may be obtained from the Stille reaction conditions to those skilled in the art (see reviews: A. Anastasia, et al, *Handbook of Organopalladium Chemistry for Organic Synthesis* 2002, 1, 311; F. Bellina, et al, *Synthesis* 2004, 2419; M. G. Organ, et al, *Synthesis* 2008, 2776; A. T. Lindhardt, et al, *Chem.—A European J.* 2008, 14, 8756; E. A. B. Kantchev, et al, *Angew. Chem. Int. Ed.* 2007, 46, 2768; V. Farina, et al, *Advances in Metal-Organic Chem.* 1996, 5, 1), using an allylstanne such as allyltributylstanne as the allyl donor. Analogously a key vinyl intermediates 1-3 may be prepared by Stille reaction from bromide 1-2 with tributylvinylstanne. Also, Sonogashira coupling between bromide 1-2 and propargyl alcohol or trimethylsilyl-acetylene can generate propargyl alcohol 1-4 or alkyne 1-5 after removal of TMS. Further bromination of intermediate 1-4 may form the propargyl bromide 1-9. In addition, the bromide 1-2 may be converted to methyl ketone 1-7 by coupling with tributyl(1-ethoxyvinyl)tin under Stille coupling conditions followed by acidic hydrolysis.

Further elaboration of the imidazopyridine or benzimidazole intermediates starts from the vinyl intermediate 1-3, which may be transformed to aldehyde 1-8 through ozonolysis or periodate/$OsO_4$ cleavage or to alcohol 1-12 by hydroboration-oxidation sequence. Alcohol 1-12 may be converted to bromide 1-15 by the well-known bromination procedure, which can be further functionalized to amine 1-20 through azide substitution followed by reduction. Aldehyde 1-8 can then either be reduced to alcohol 1-11, or be converted to α,β-unsaturated acid 1-10 through Horner-Wadsworth-Emmons aldehyde homologation reaction followed by saponification. Alcohol 1-11 may be similarly converted to the corresponding amine intermediate 1-14 and bromide intermediate 1-13 as described previously. Bromide 1-13 can be homologated to alkyne intermediate 1-19 with a metal acetylide. In addition, bromide 1-13 may be also transformed to thiol 1-16 through nucleophilic substitution, which can be further oxidized to sulfonic acid 1-17. Sulfonamide 1-18 may then be derived from 1-17 through the sulfonyl chloride activation process.

It should be noted that optionally the NH group of all the imidazopyridine or benzimidazole related intermediates listed above may be protected with an amino protecting group, such as SEM (i.e. SEM-Cl, NaH), Boc, Cbz, Teoc, Troc, or the like.

Scheme 2

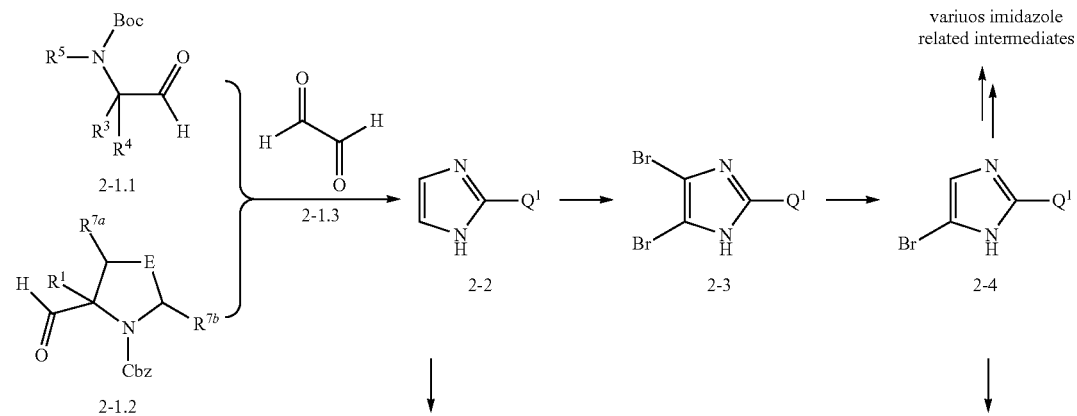

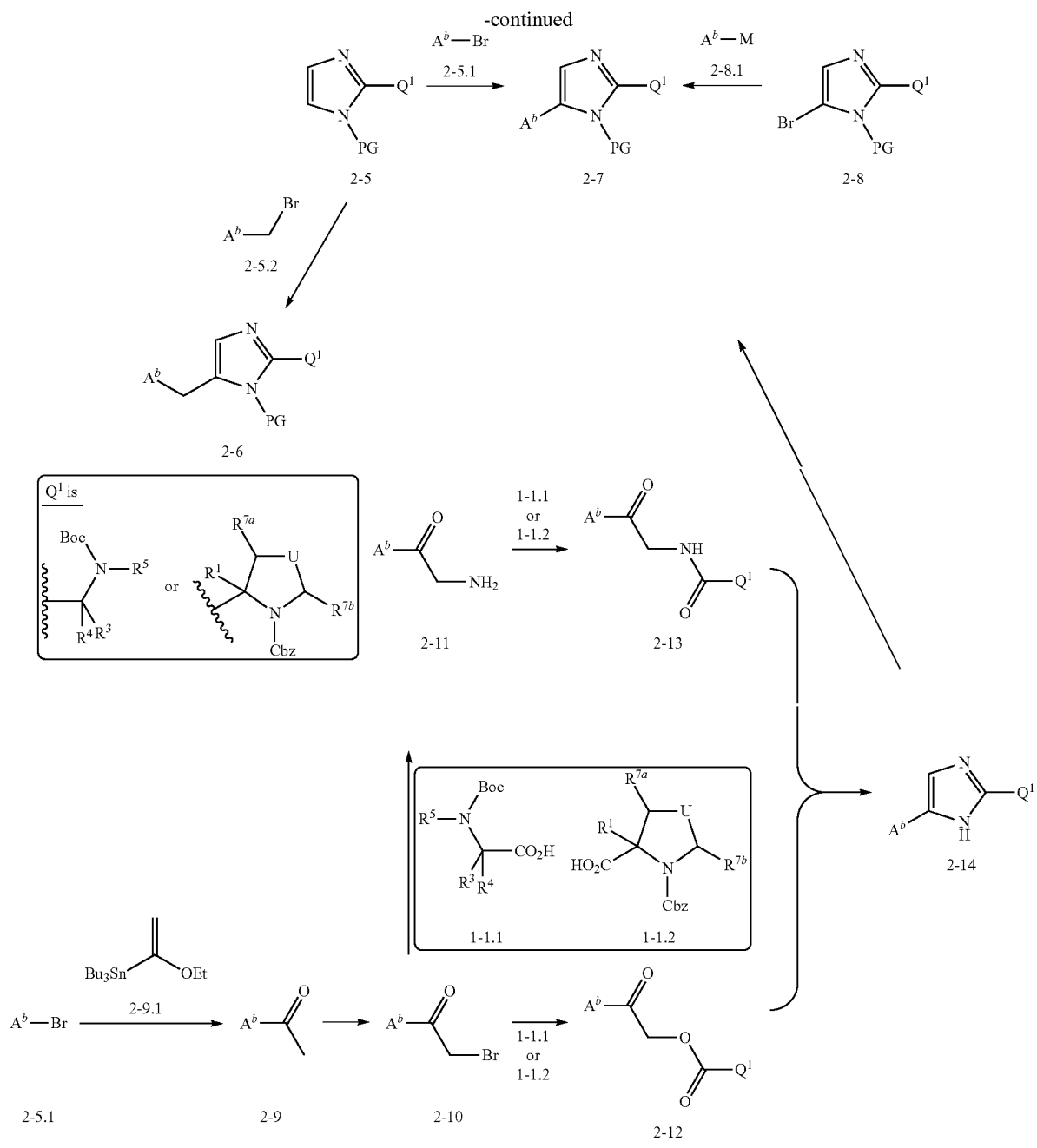

A typical syntheses of imidazole related intermediates are analogous to that of the imidazopyridine or benzimidazole intermediates. As shown in Scheme 2, bromo-imidazole 2-4 can be synthesized in a three-step sequence: 1) condensation between amino acid derived aldehyde 2-1.1 or 2-1.2 and glyoxal 2-1.3 in the presence of methanolic ammonia to generate imidazole 2-2; 2) bromination of 2-2 with excess amount of bromination reagent such as 2,4,4,6-tetrabromo-2,5-cyclohexadienone, NBS, etc. to afford dibromide 2-3; and 3) selective reduction of the dibromide 2-3 by heating in aq. $Na_2SO_3$ or aq. $NaHSO_3$. 2-4 then may be served as a universal intermediate further elaborable to many other imidazole derivatives using the chemistry discussed in Scheme 1, some of which are listed in the table below.

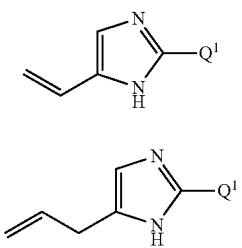

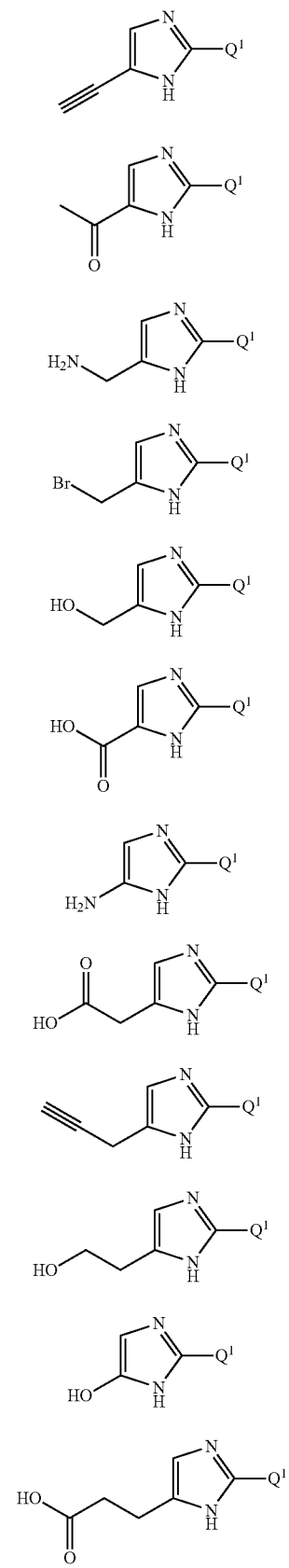
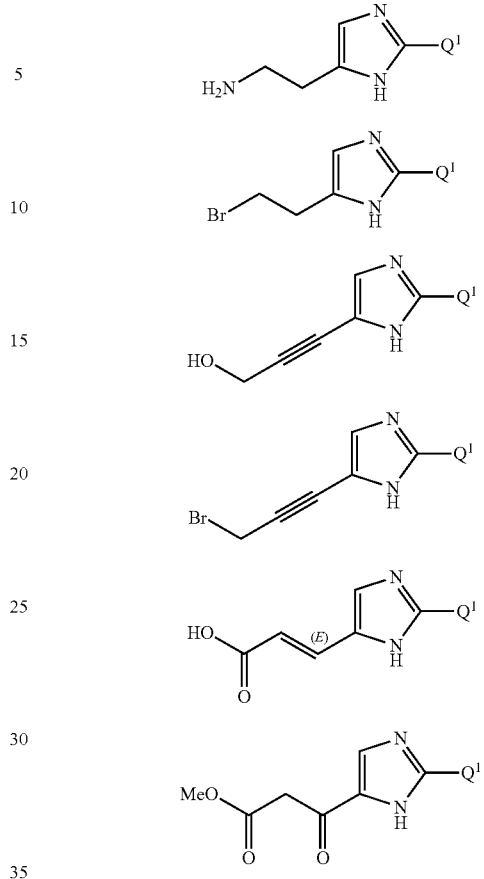

Optionally, the NH group of imidazole related intermediates listed above may be protected with an amino protecting group (shown in Scheme 2 as PG, theoretically the reaction will generate two regio-isomers, but only one is drawn for clarity), such as SEM (i.e. SEM-Cl, NaH), Boc, Cbz, Teoc, Troc, or the like. The protected imidazole 2-5 may be deprotonated with a strong base such as LDA, BuLi, etc to generate a carbon anion, which may either undergo a nucleophilic substitution with an activated halide such as 2-5.2 to afford aryl or heteroaryl substituted imidazole 2-6 or couple with an aryl or heteroaryl halide 2-5.1 in the presence appropriate transition metal salt to generate bicyclic heteroaryl 2-7. Similarly, the protected bromo imidazole 2-8 may be subjected to lithium-halogen exchange with various (n-, s-, or t-) butyl lithium, the resulting lithiate may undergo similar reactions to afford 2-6 and 2-7. Also, when 2-8 is treated with metallated aryl or heteroaryl 2-8.1, in which M at each occurrence is independently a boron, tin, silicon, zinc, zirconium, or copper species, under Suzuki, Stille or related coupling conditions known to those skilled in the art (see reviews: A. Suzuki, *Pure Applied Chem.* 1991, 63, 419; A. Suzuki, *Handbook of Organopalladium Chemistry for Organic Synthesis* 2002, 1, 249; A. Anastasia, et al, *Handbook of Organopalladium Chemistry for Organic Synthesis* 2002, 1, 311; F. Bellina, et al, *Synthesis* 2004, 2419; M. G. Organ, et al, *Synthesis* 2008, 2776; A. T. Lindhardt, et al, *Chem.—A European J.* 2008, 14, 8756; E. A. B. Kantchev, et al, *Angew. Chem. Int. Ed.* 2007, 46, 2768; V. Farina, et al, *Advances in Metal-Organic Chem.* 1996, 5, 1), to provide coupling product 2-7. In addition to these direct coupling strategy, aryl or heteroaryl bromide 2-5.1 may be converted to methyl ketone 2-9 under Stille coupling conditions with tributyl(1-ethoxyvinyl)tin 2-9.1. 2-9 may be brominated under conditions to those skilled in the art to afford bromide 2-10, which may be either converted to the corresponding amine 2-11, or coupled with protected amino acid 1-1.1 or 1-1.2 in the presence of a base such as Et$_3$N and DIPEA to afford keto-ester 2-12. Similarly, amine 2-11 may be converted to the corresponding keto-amide 2-13 via condensation with appropriate amino acid under standard amide formation conditions. 2-12 and 2-13 may be transformed to key intermediate 2-14 via heating with (NH$_4$)OAc under thermal or microwave conditions.

Similarly when W and/or Q are fused bicyclic groups as previously defined, compounds of the present invention may be synthesized from intermediates 3-2 and 3-3 (as shown in Scheme 3), which may be synthesized using similar chemistry described in Schemes 1 and 2 from the bicyclic carboxylic acid 3-1. Bicyclic carboxylic acids or derivatives with various structural features are either commercially available or known in the literature, and have been extensively reviewed by S. Hanessian, et al (*Tetrahedron* 1997, 53, 12789) and A. Trabocchi, et al (*Amino Acids* 2008, 34, 1) which are incorporated herein by reference.

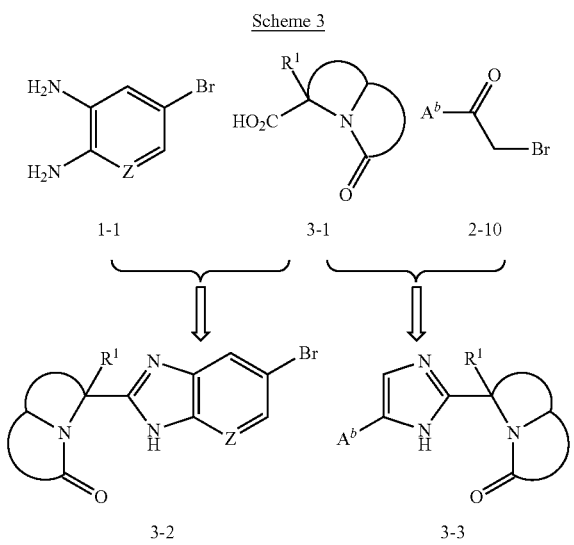

Scheme 3

With a variety of suitably substituted imidazopyridines, benzimidazoles and imidazoles in hand, such as those listed in Schemes 1-3 and the table above, the compounds of the present invention may be prepared through various coupling strategy or a combination of strategies to connect two fragments, optionally with a suitable cyclic or acyclic linker or formation of a cyclic or acyclic linker. The said strategy includes, but not limited to, Stille coupling, Suzuki coupling, Sonogashira coupling, Heck coupling, Buchwald amidation, Buchwald amination, amide coupling, ester bond formation, William etherification, Buchwald etherification, alkylation, pericyclic reaction with different variations, or the like.

An example of the strategies that may be used to prepare the compounds of the present invention is shown in Scheme 4, wherein $R^{1a}$ and $R^{2a}$ at each occurrence are each independently selected from the group consisting of halogen, cyano, optionally substituted $C_1$-$C_4$ alkyl, —O—($C_1$-$C_4$ alkyl), —N($C_1$-$C_4$ alkyl)$_2$, —CO$_2$($C_1$-$C_4$ alkyl), and —C(O)N($C_1$-$C_4$ alkyl)$_2$; preferably hydrogen, halogen and optionally substituted $C_1$-$C_4$ alkyl. Both bromides 4-1 and 4-2 can be prepared using the procedures described in Schemes 1-3. Bromide 4-2 can be converted to the corresponding metalated aryl 4-3 under Suzuki or Stille conditions, which may be further coupled with imidazopyridine bromide 4-1 under similar conditions to generate a structural core 4-4.

Compound 4-4 then may be served as a common intermediate for further derivatizations to 4-5 in two steps: 1) monodeprotection of the linear or cyclic amine moiety may be accomplished, for example, treatment to hydrogenolytic conditions under Pd catalyst to remove the Cbz protection group; and 2) the released amine functionality may be acylated with an carboxylic acid under standard acylation conditions, for example a coupling reagent such as HATU in combination with an organic base such as DIPEA can be used in this regard; alternatively, the released amine may be reacted with an isocyanate, carbamoyl chloride or chloroformate to provide an urea or carbamate. Various carboxylic acids including amino acids in racemic or optical form are commercially available, and/or can be synthesized in racemic or optical form, see references cited in reviews by D. Seebach, et al, *Synthesis* 2009, 1; C. Cativiela and M. D. Diaz-de-Villegas, *Tetrahedron: Asymmetry* 2007, 18, 569; 2000, 11, 645; and 1998, 9, 3517; and experimental examples compiled in patent application WO 08/021,927 A2 by C. Bachand, et al, from BMS, which is incorporated herein by reference. 4-5 may be further deprotected under hydrolytic conditions in the presence of an acid such as TFA or hydrogen chloride to remove the Boc protection group and the released amine functionality can be further derivatized to the title compounds I-1, with a carboxylic acid using the conditions described above.

Scheme 4

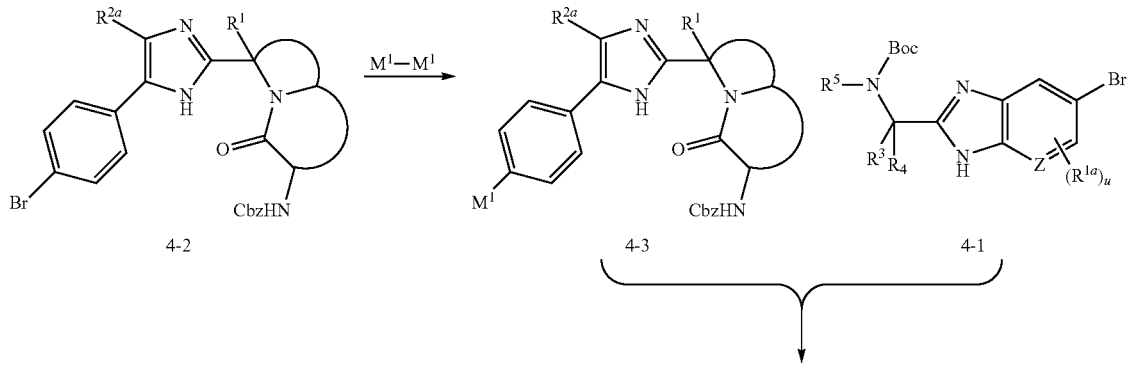

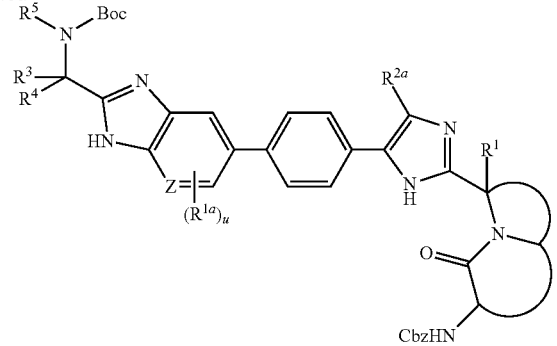

4-4

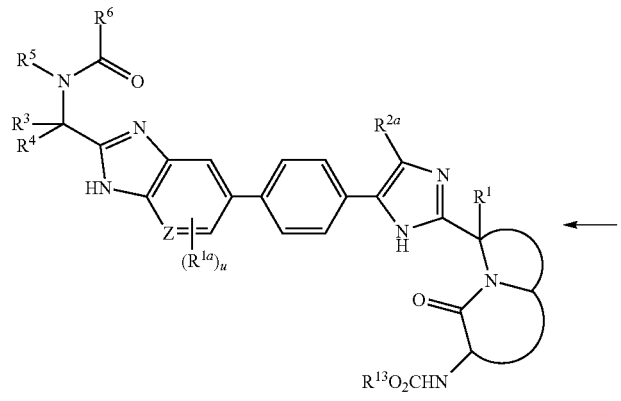

I-1

M¹ = boron or tin species
Z = N or CH
u = 0, 1, 2

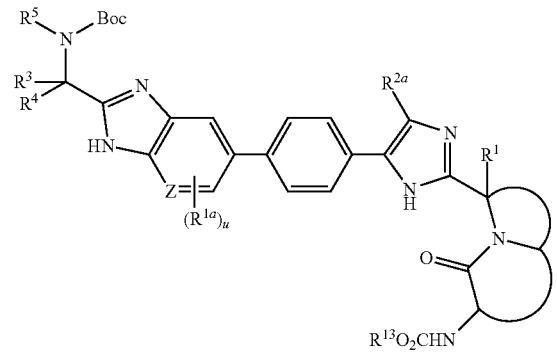

4-5

Other examples of some of the linkers that may be used to construct the title compounds of the present invention are compiled in the table below, in which PG and PG' at each occurrence are each independently amino or alcohol protecting group, such as Boc, Cbz, Troc, Teoc, PMB, TMS etc. These linkers are either commercially available or may be synthesized in several steps through strategies which are known to those skilled in the art.

-continued

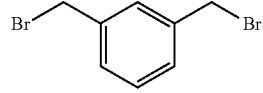

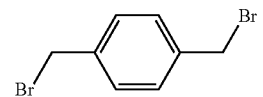

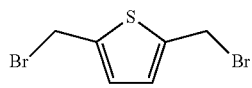

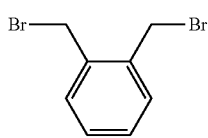

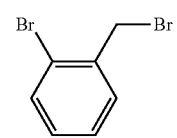

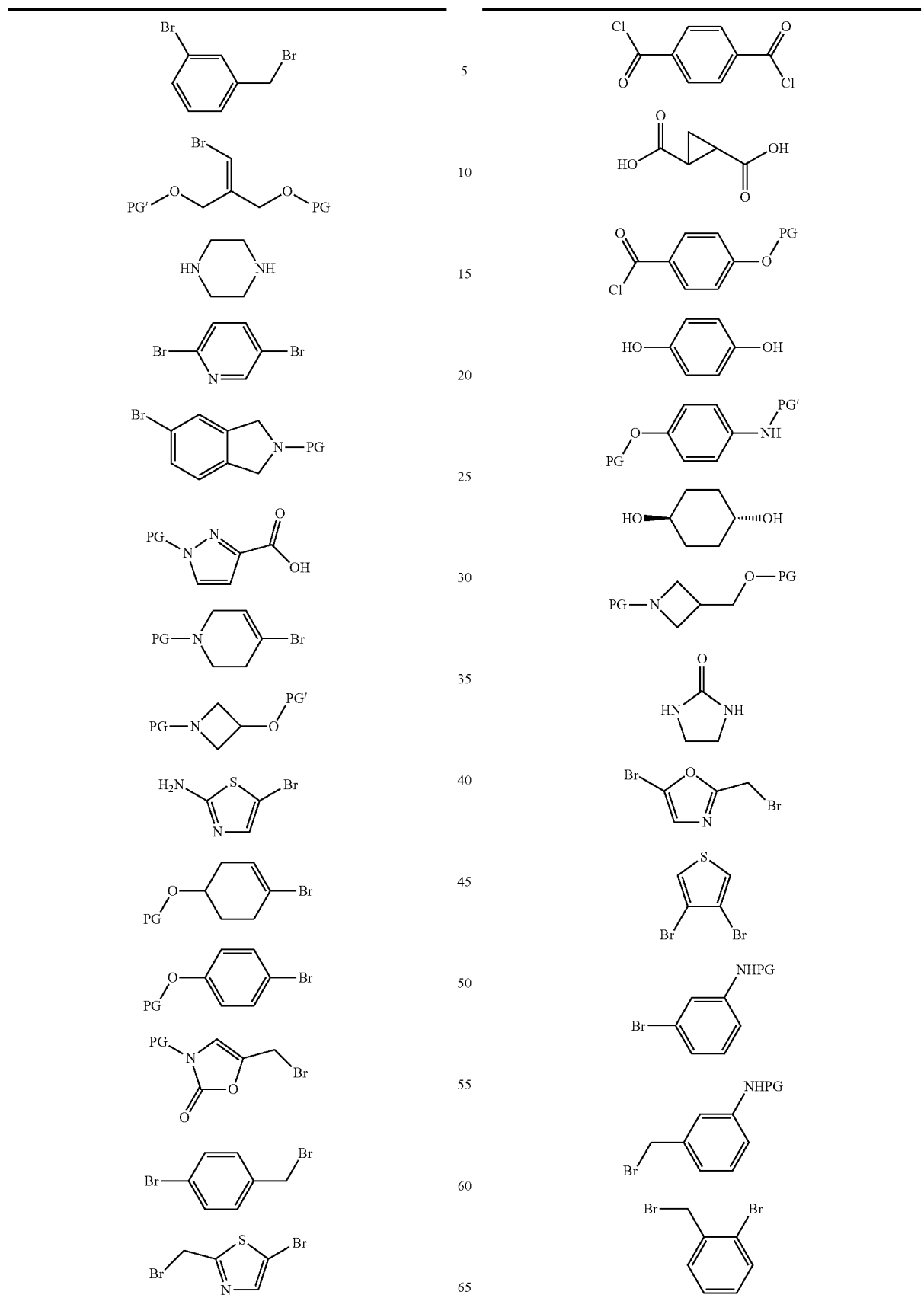

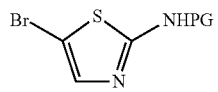

Alternatively, as shown in Scheme 4a, the compounds of the present invention (for example I-1) may also be derived from bromoimidazopyridine or bromobenzimidazole 4-1a and imidazole 4-3a using the procedures described previously. The intermediates 4-1a and 4-3a have the desired acyl groups already installed as seen in amino acid derivatives 1-1.1b and 1-1.2b, which can be prepared from protected amino acids 1-1.1a and 4-2a through the sequences shown in Schemes 1-3.

Scheme 4a

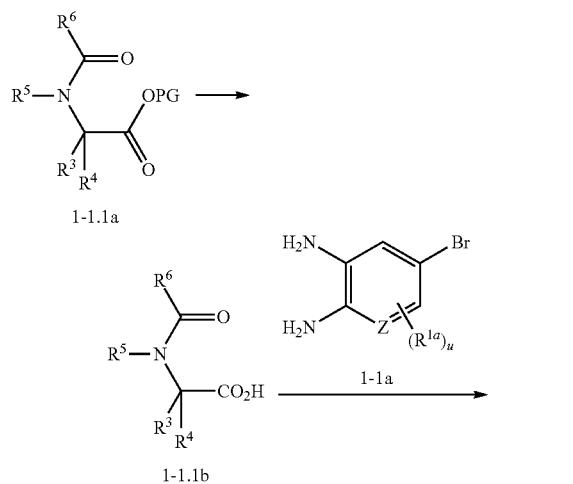

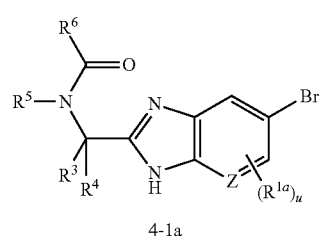

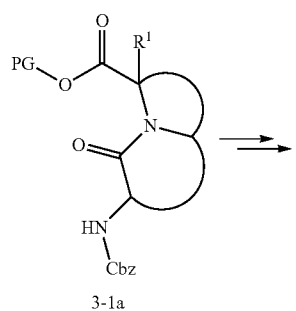

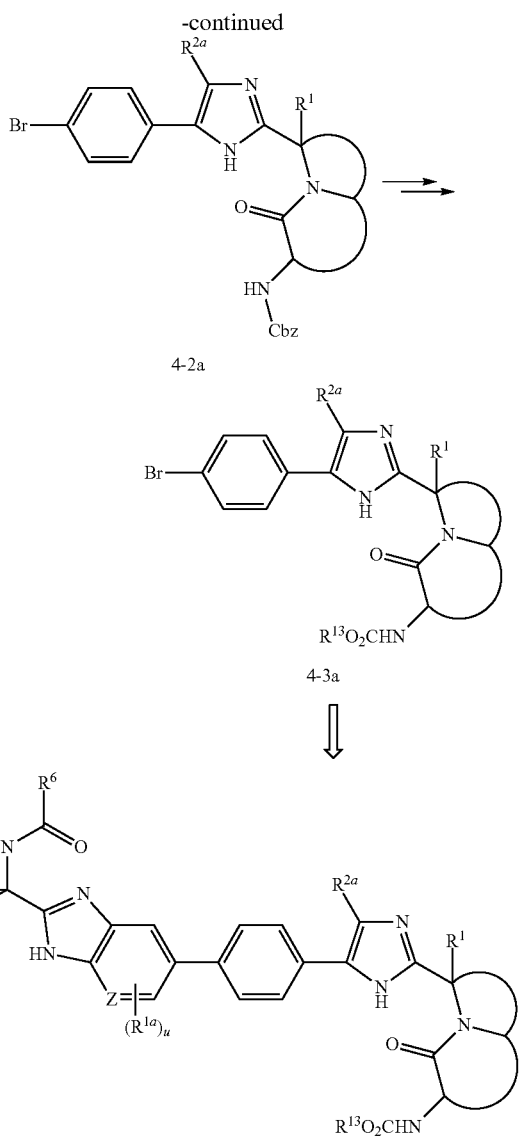

PG is carboxylic acid protecting group
Z, $R^1$ and $R^2$ are as defined previously The compounds of the present invention containing five-membered heteroaryl other than imidazole may be prepared using similar procedures described above in Schemes 1-4 and 4a. For example, some intermediates containing a desired, suitably substituted five-membered heteroaryl have been published in US 2008/0311075A1 by C. Bachand, et al from BMS, which is incorporated by reference. Theses intermediates are compiled in the following table.

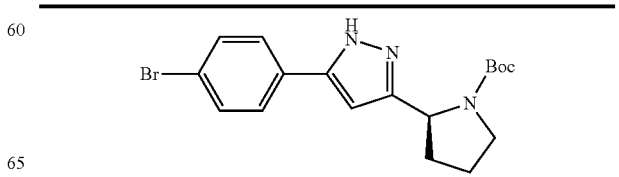

-continued

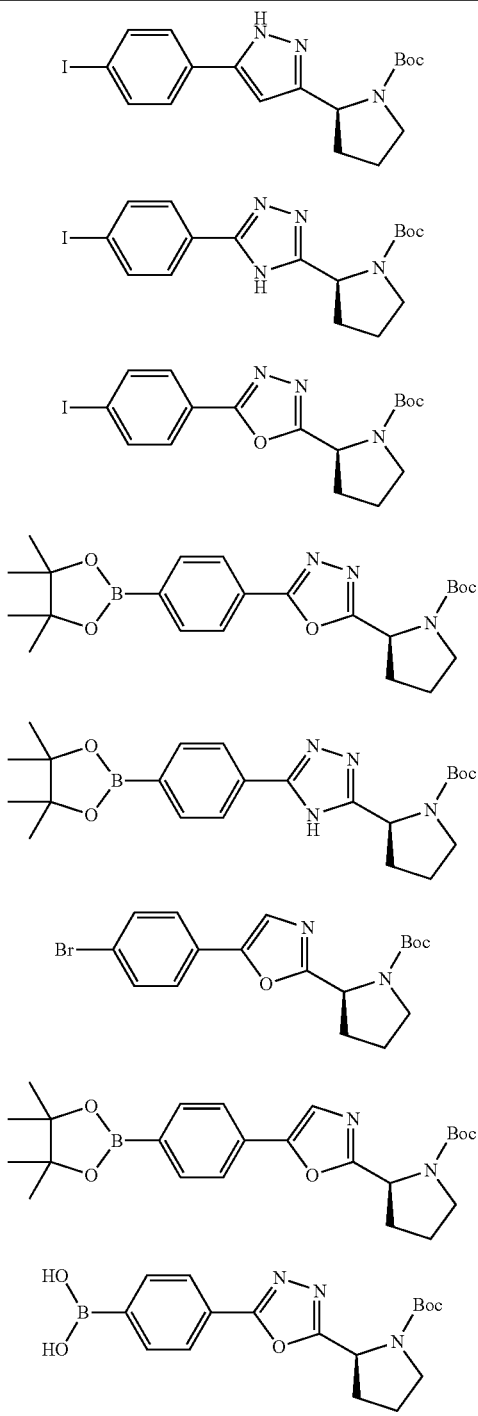

phenylacetylene 5-2. The latter may be cyclized to indole 5-3 under heat or microwave condition in the presence of a copper catalyst.

Scheme 5

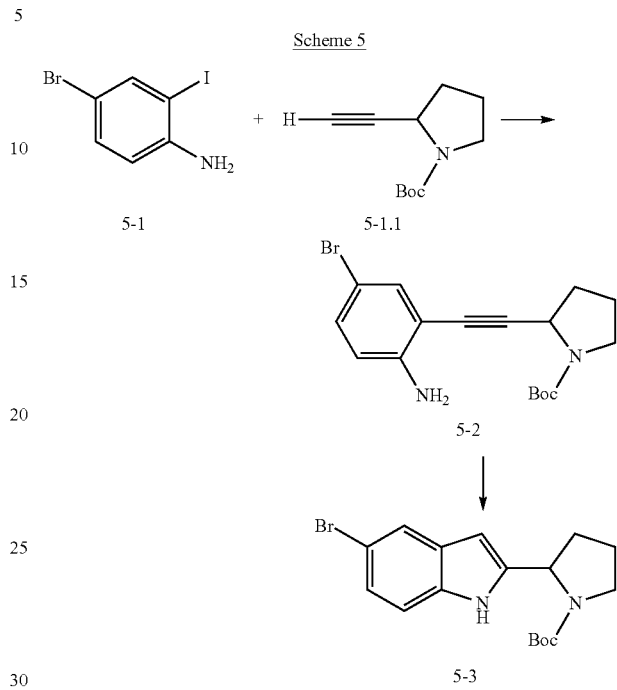

It will be appreciated that, with appropriate manipulation and protection of any chemical functionality, synthesis of compounds of Formula (I) is accomplished by methods analogous to those above and to those described in the Experimental section. Suitable protecting groups can be found, but are not restricted to, those found in T W Greene and P G M Wuts "Protective Groups in Organic Synthesis", 3rd Ed (1999), J Wiley and Sons.

In certain aspects, the invention encompasses a process of making a compound of the invention:

i) Preparing a compound of Formula (III):

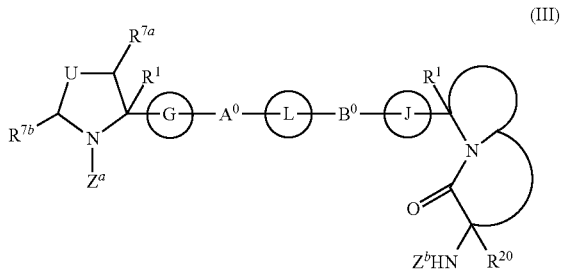

(III)

via a transition-metal catalyzed cross-coupling reaction; wherein:
ring G, ring J, ring L, U, $R^1$, $R^{7a}$, and $R^{7b}$ are as defined in Formula (I);
$A^0$ and $B^0$ are each independently absent, optionally substituted $C_2$-$C_4$ alkenyl or $C_2$-$C_4$ alkynyl;
$R^{20}$ is hydrogen or $C_1$-$C_4$ alkyl;
$Z^a$ is an amino protecting group or —C(O)—$R^6$; and
$Z^b$ is an amino protecting group or —C(O)—$OR^{13}$;

The synthesis of the compounds of the present invention involves 5/6-membered fused heteroaryl intermediates other than imidazopyridines or benzimidazoles, various 5/6-membered fused heteroaryl are known in the literature. The synthesis of other 5/6-membered fused heteroaryl intermediates depends on the chemical features of each structure. For example, a typical synthesis of indole intermediate is illustrated in Scheme 5. The commercially available bromoiodoaniline 5-1 may be coupled to the commercially available acetylene 5-1.1 under the Sonogashira conditions to give ii) When Z or $Z^a$ is an amino protecting group, fully or selectively deprotecting a compound of Formula (III) to give the corresponding amine of Formula (IV):

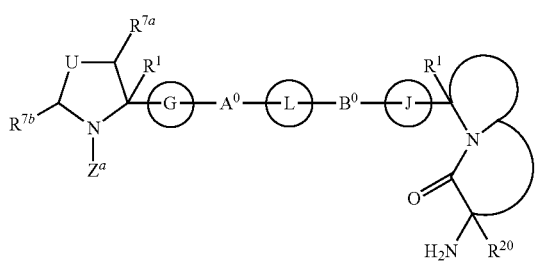

(IV)

wherein $Z^c$ is hydrogen, an amino protecting group or —C(O)—$R^6$;

iii) Capping the released amino group of a compound of Formula (IV) with LG-C(O)—$OR^{13}$, wherein $R^{13}$ is as defined in Formula (I); LG is a leaving group; to give the compound of Formula (V):

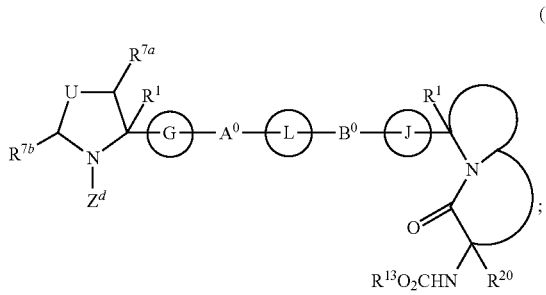

(V)

wherein $Z^d$ is an amino protecting group —C(O)—$R^6$; and iv) Repeated reaction sequence of deprotecting and capping (step ii-iii) to give the compound of Formula (VI),

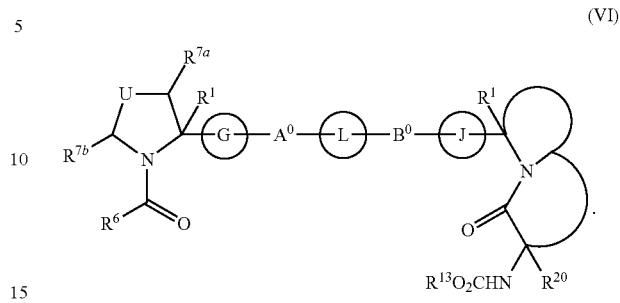

(VI)

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Although the invention has been described with respect to various preferred embodiments, it is not intended to be limited thereto, but rather those skilled in the art will recognize that variations and modifications may be made therein which are within the spirit of the invention and the scope of the appended claims.

The compounds of examples 1-367 may be prepared using procedures similar to those described in examples 368-376 (described below), and/or as described in the Synthetic Methods.

TABLE 1

Examples 1-219.

TABLE 1-continued

Examples 1-219.

| Entry | R group |
|---|---|
| 2 | methyl carbamate-NH-CH(Ph)-C(O)- (S) |
| 3 | Me₂N-CH(Ph)-C(O)- (S) |
| 4 | CH₃-CH(OH)-C(O)- (S) |
| 5 | CH₃CH₂-CH(OH)-C(O)- (S) |
| 6 | CH₃CH₂-C(O)- |
| 7 | MeO-CH₂-C(O)- |
| 8 | Me₂N-C(O)- |
| 9 | MeO-C(O)- |
| 10 | CH₃-C(O)-CH₂CH₂-C(O)- |

TABLE 1-continued
Examples 1-219.
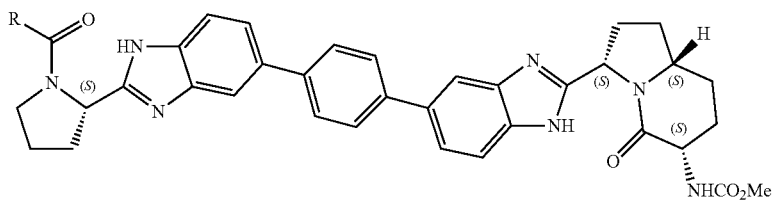
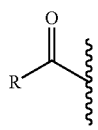
| Entry | |
|---|---|
| 11 | (isopropyl-CH(OH)-C(O)-) |
| 12 | (Me2N-C(O)-C(O)-) |
| 13 | (cyclopropyl-C(O)-) |
| 14 | (1-CF3-cyclopropyl-C(O)-) |
| 15 | (1-OH-cyclopropyl-C(O)-) |
| 16 | (Ph-C(O)-) |
| 17 | (PhCH2-C(O)-) |
| 18 | (cyclopropyl-CH2-C(O)-) |
| 19 | (Ph-C(Me)(OH)-C(O)-) |

TABLE 1-continued
Examples 1-219.
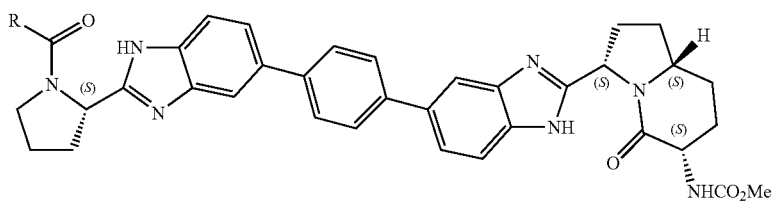
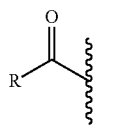
Entry
20 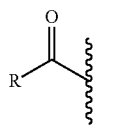
21 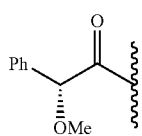
22 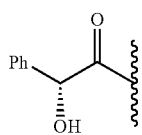
23 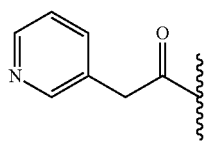 [SMILES: *C(=O)Cc1cccnc1]
24 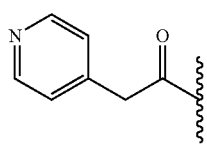 [SMILES: *C(=O)Cc1ccncc1]
25 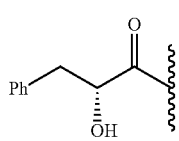 [SMILES: *C(=O)[C@H](O)Cc1ccccc1]
26 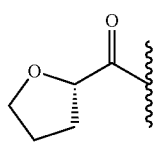 [SMILES: *C(=O)[C@@H]1CCCO1]
27 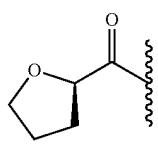 [SMILES: *C(=O)[C@H]1CCCO1]

TABLE 1-continued
Examples 1-219.
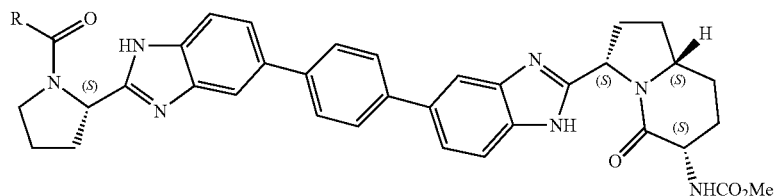
| Entry | 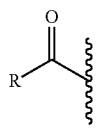 |
|---|---|
| 28 | 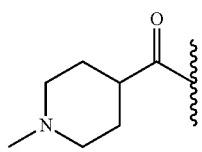 [SMILES: *C(=O)C1CCN(C)CC1] |
| 29 | 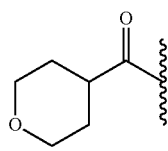 [SMILES: *C(=O)C1CCOCC1] |
| 30 | 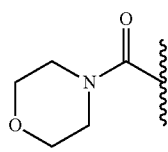 [SMILES: *C(=O)N1CCOCC1] |
| 31 | 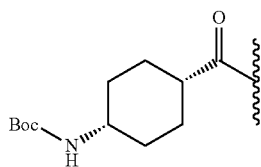 [SMILES: *C(=O)[C@H]1CC[C@@H](NC(=O)OC(C)(C)C)CC1] |
| 32 | 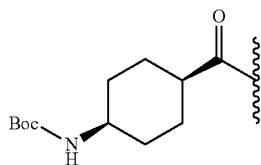 [SMILES: *C(=O)[C@H]1CC[C@@H](NC(=O)OC(C)(C)C)CC1] |
| 33 | 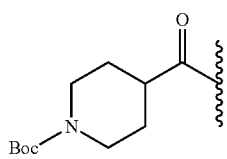 [SMILES: *C(=O)C1CCN(C(=O)OC(C)(C)C)CC1] |
| 34 | 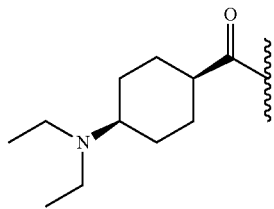 [SMILES: *C(=O)[C@H]1CC[C@@H](N(CC)CC)CC1] |

TABLE 1-continued
Examples 1-219.
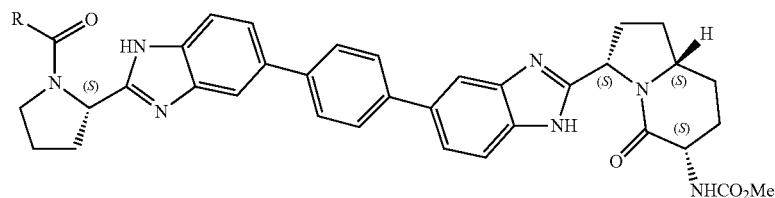
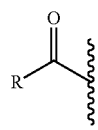
| Entry | |
|---|---|
| 35 | 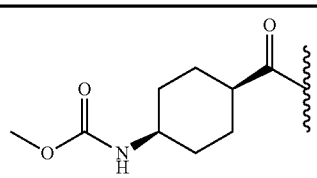 |
| 36 | 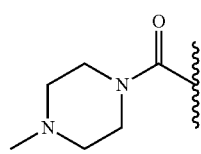 [SMILES: *C(=O)N1CCN(C)CC1] |
| 37 | 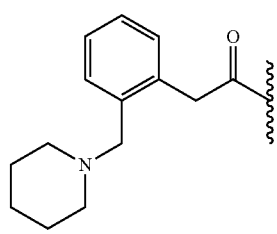 [SMILES: *C(=O)Cc1ccccc1CN1CCCCC1] |
| 38 | 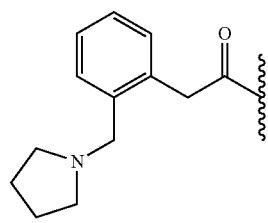 [SMILES: *C(=O)Cc1ccccc1CN1CCCC1] |
| 39 | 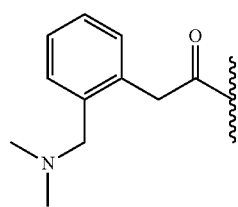 [SMILES: *C(=O)Cc1ccccc1CN(C)C] |
| 40 | 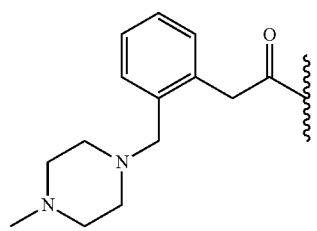 [SMILES: *C(=O)Cc1ccccc1CN1CCN(C)CC1] |

TABLE 1-continued
Examples 1-219.
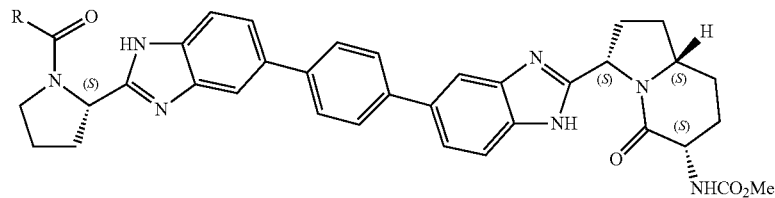
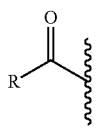
| Entry | |
|---|---|
| 41 | 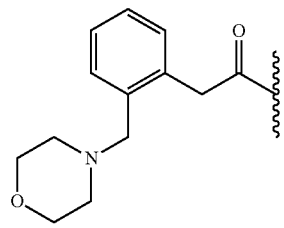 [SMILES: *C(=O)Cc1ccccc1CN1CCOCC1] |
| 42 | 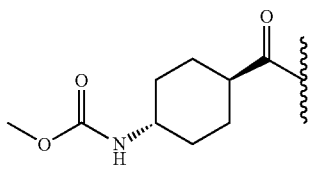 [SMILES: *C(=O)[C@H]1CC[C@H](NC(=O)OC)CC1] |
| 43 | 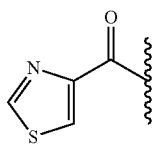 [SMILES: *C(=O)c1cscn1] |
| 44 | 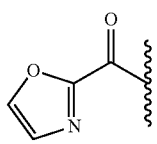 [SMILES: *C(=O)c1ncco1] |
| 45 | 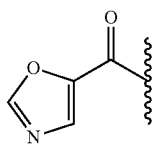 [SMILES: *C(=O)c1cnco1] |
| 46 | 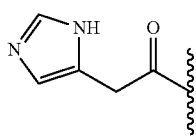 |
| 47 | 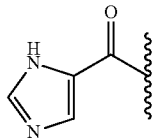 [SMILES: *C(=O)c1cnc[nH]1] |

TABLE 1-continued
Examples 1-219.
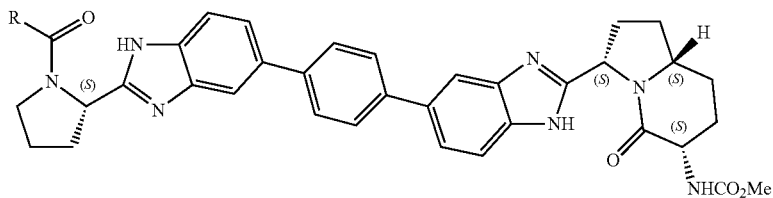
| Entry | |
|---|---|
| 48 | 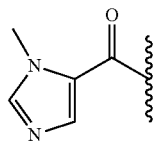 [SMILES: *C(=O)c1cncn1C] |
| 49 | 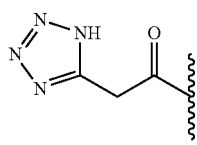 [SMILES: *C(=O)Cc1nnn[nH]1] |
| 50 | 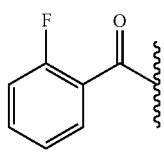 [SMILES: *C(=O)c1ccccc1F] |
| 51 | 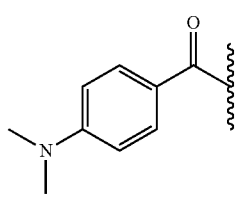 [SMILES: *C(=O)c1ccc(N(C)C)cc1] |
| 52 | 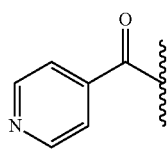 [SMILES: *C(=O)c1ccncc1] |
| 53 | 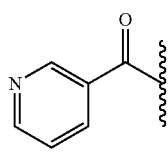 [SMILES: *C(=O)c1cccnc1] |
| 54 | 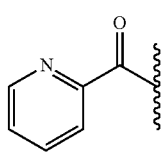 [SMILES: *C(=O)c1ccccn1] |

TABLE 1-continued
Examples 1-219.
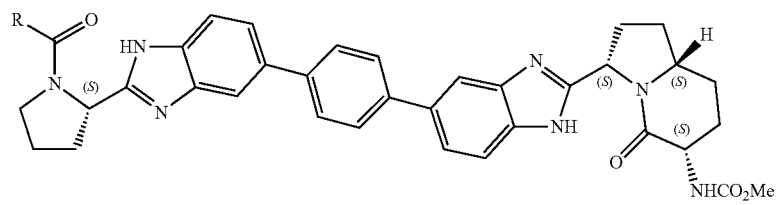
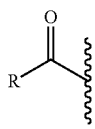
| Entry | |
|---|---|
| 55 | 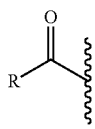 |
| 56 | 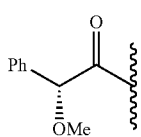 |
| 57 |  |
| 58 | 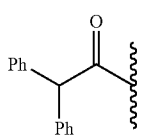 |
| 59 | 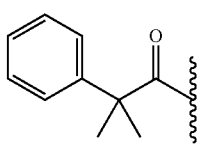 |
| 60 | 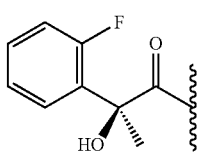 [SMILES: *C(=O)[C@@](C)(O)c1ccccc1F] |
| 61 | 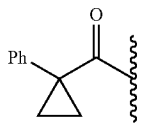 [SMILES: *C(=O)C1(c2ccccc2)CC1] |
| 62 | 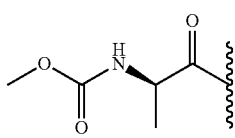 [SMILES: *C(=O)[C@@H](C)NC(=O)OC] |

TABLE 1-continued
Examples 1-219.
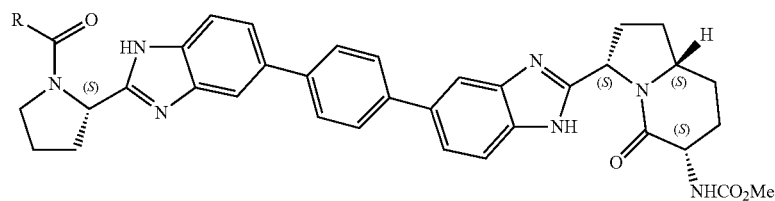
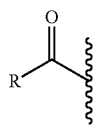
| Entry | |
|---|---|
| 63 | 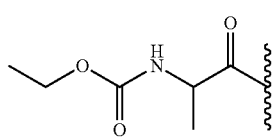 [SMILES: *C(=O)C(C)NC(=O)OCC] |
| 64 | 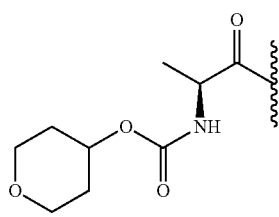 [SMILES: *C(=O)[C@H](C)NC(=O)OC1CCOCC1] |
| 65 | 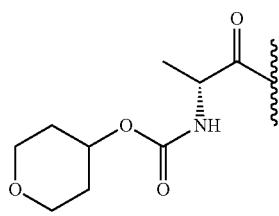 [SMILES: *C(=O)[C@@H](C)NC(=O)OC1CCOCC1] |
| 66 | 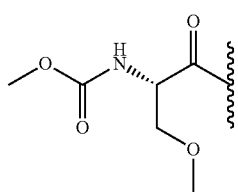 [SMILES: *C(=O)[C@H](COC)NC(=O)OC] |
| 67 | 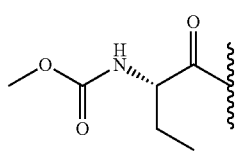 [SMILES: *C(=O)[C@H](CC)NC(=O)OC] |
| 68 | 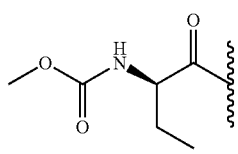 [SMILES: *C(=O)[C@@H](CC)NC(=O)OC] |

TABLE 1-continued
Examples 1-219.
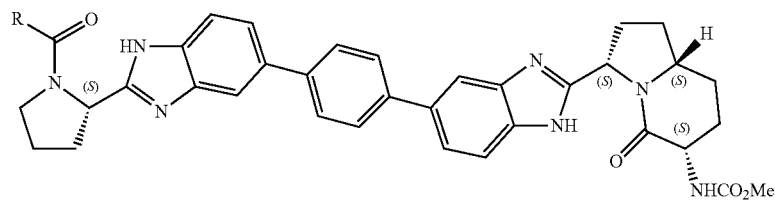
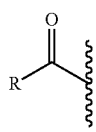
| Entry | |
|---|---|
| 69 | 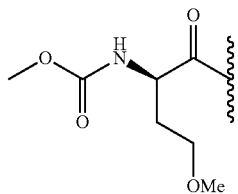 [SMILES: *C(=O)[C@@H](CCOC)NC(=O)OC] |
| 70 | 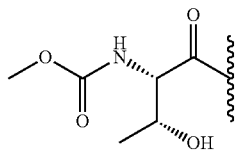 [SMILES: *C(=O)[C@@H](NC(=O)OC)[C@@H](C)O] |
| 71 | 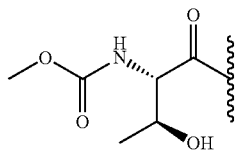 [SMILES: *C(=O)[C@@H](NC(=O)OC)[C@H](C)O] |
| 72 | 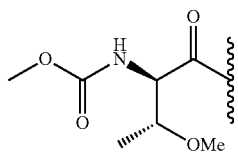 [SMILES: *C(=O)[C@H](NC(=O)OC)[C@@H](C)OC] |
| 73 | 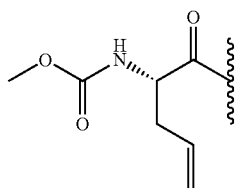 [SMILES: *C(=O)[C@H](CC=C)NC(=O)OC] |
| 74 | 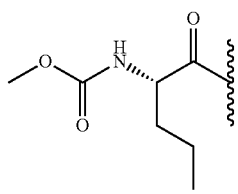 [SMILES: *C(=O)[C@H](CCC)NC(=O)OC] |

TABLE 1-continued
Examples 1-219.
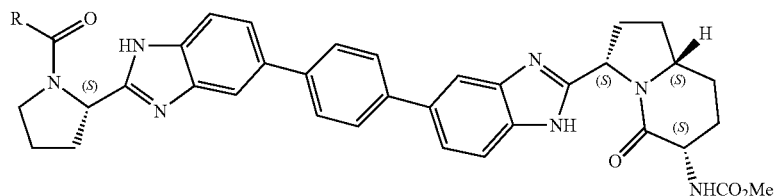
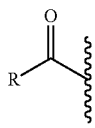
| Entry | |
|---|---|
| 75 | 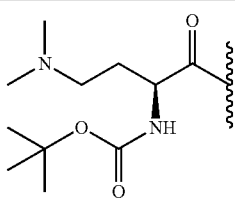 [SMILES: *C(=O)[C@H](CCN(C)C)NC(=O)OC(C)(C)C] |
| 76 | 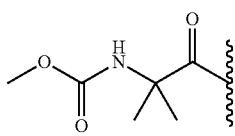 [SMILES: *C(=O)C(C)(C)NC(=O)OC] |
| 77 | 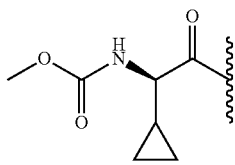 [SMILES: *C(=O)[C@H](NC(=O)OC)C1CC1] |
| 78 | 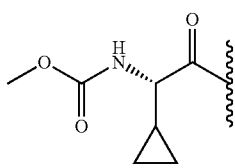 [SMILES: *C(=O)[C@@H](NC(=O)OC)C1CC1] |
| 79 | 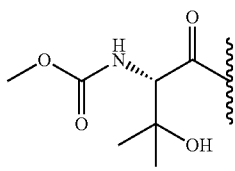 [SMILES: *C(=O)[C@@H](NC(=O)OC)C(C)(C)O] |
| 80 | 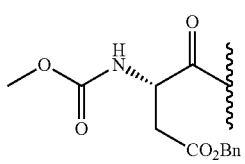 |
| 81 | 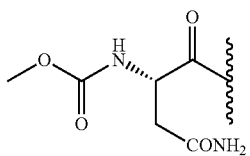 |

TABLE 1-continued
Examples 1-219.
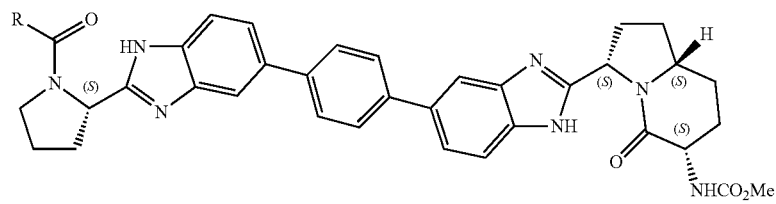
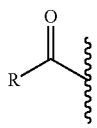
| Entry | |
|---|---|
| 82 | 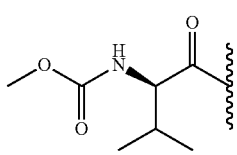 [SMILES: *C(=O)[C@H](NC(=O)OC)C(C)C] |
| 83 | 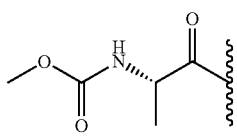 [SMILES: *C(=O)[C@H](C)NC(=O)OC] |
| 84 | 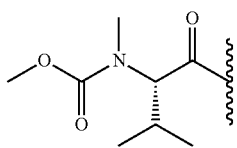 [SMILES: *C(=O)[C@H](C(C)C)N(C)C(=O)OC] |
| 85 | 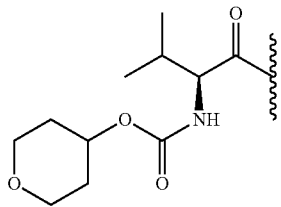 [SMILES: *C(=O)[C@@H](NC(=O)OC1CCOCC1)C(C)C] |
| 86 | 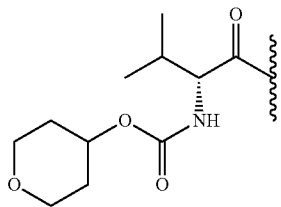 [SMILES: *C(=O)[C@H](NC(=O)OC1CCOCC1)C(C)C] |
| 87 | 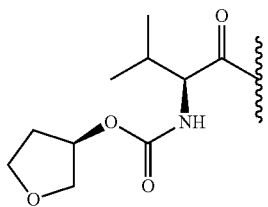 [SMILES: *C(=O)[C@@H](NC(=O)O[C@@H]1CCOC1)C(C)C] |

TABLE 1-continued
Examples 1-219.
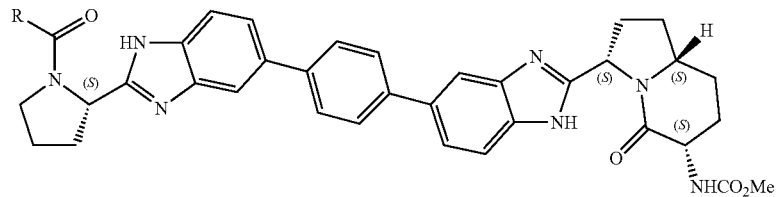
| Entry | 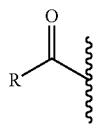 |
|---|---|
| 88 | 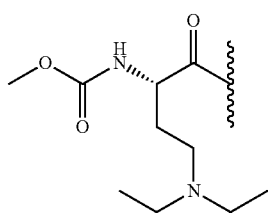 [SMILES: *C(=O)[C@H](CCN(CC)CC)NC(=O)OC] |
| 89 | 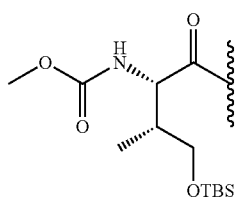 [SMILES: *C(=O)[C@@H](NC(=O)OC)[C@@H](C)CO[Si](C)(C)C(C)(C)C] |
| 90 | 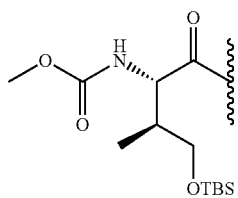 [SMILES: *C(=O)[C@@H](NC(=O)OC)[C@H](C)CO[Si](C)(C)C(C)(C)C] |
| 91 | 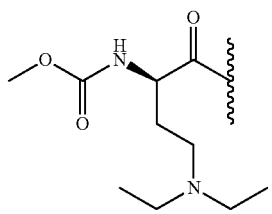 [SMILES: *C(=O)[C@@H](CCN(CC)CC)NC(=O)OC] |
| 92 | 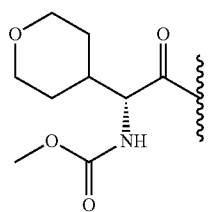 [SMILES: *C(=O)[C@H](NC(=O)OC)C1CCOCC1] |

TABLE 1-continued
Examples 1-219.
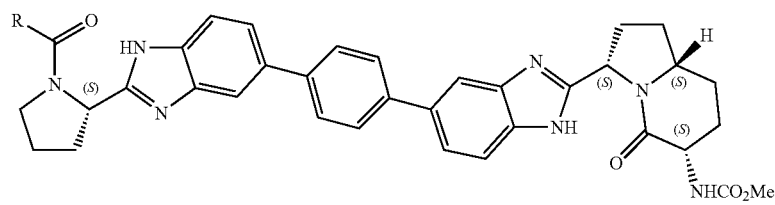
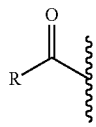
| Entry | |
|---|---|
| 93 | 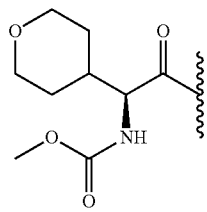 [SMILES: *C(=O)[C@@H](NC(=O)OC)C1CCOCC1] |
| 94 | 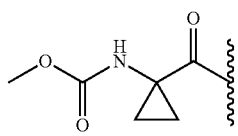 [SMILES: *C(=O)C1(NC(=O)OC)CC1] |
| 95 | 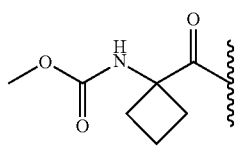 [SMILES: *C(=O)C1(NC(=O)OC)CCC1] |
| 96 | 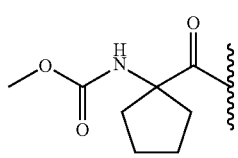 [SMILES: *C(=O)C1(NC(=O)OC)CCCC1] |
| 97 | 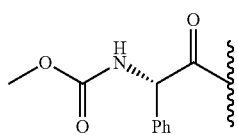 [SMILES: *C(=O)[C@@H](NC(=O)OC)c1ccccc1] |
| 98 | 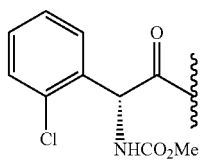 |
| 99 | 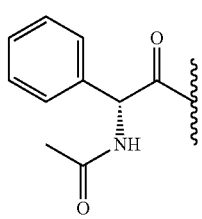 [SMILES: *C(=O)[C@H](NC(C)=O)c1ccccc1] |

TABLE 1-continued
Examples 1-219.
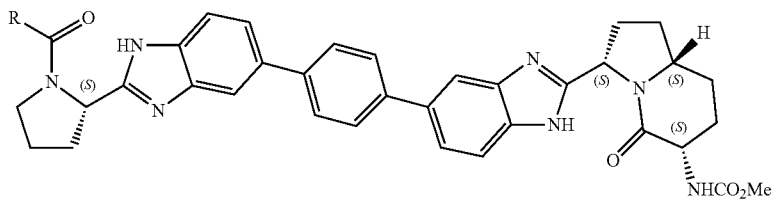
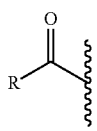
| Entry | |
|---|---|
| 100 | ![structure] phenyl-CH(NHC(O)NHMe)-C(O)- |
| 101 | phenyl-CH(NHC(O)NMe$_2$)-C(O)- |
| 102 | phenyl-CH(NHC(O)NHEt)-C(O)- |
| 103 | phenyl-CH(NHC(O)NH-cyclopentyl)-C(O)- |
| 104 | N-(MeO$_2$C)-azetidine-2-carbonyl- |
| 105 | N-Boc-azetidine-3-carbonyl- |

TABLE 1-continued
Examples 1-219.
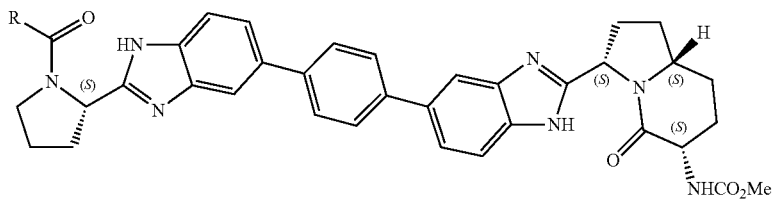
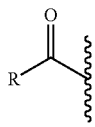
| Entry | |
|---|---|
| 106 | 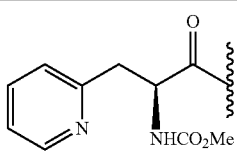 |
| 107 | 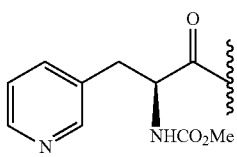 |
| 108 | 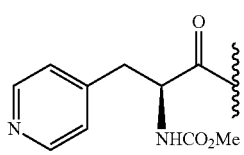 |
| 109 | 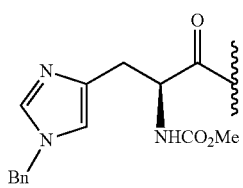 |
| 110 | 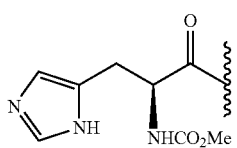 |
| 111 | 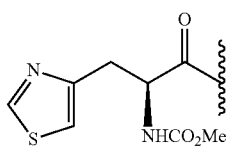 |
| 112 | 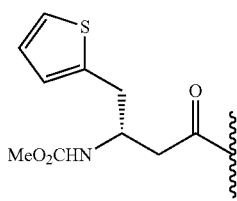 |

TABLE 1-continued
Examples 1-219.
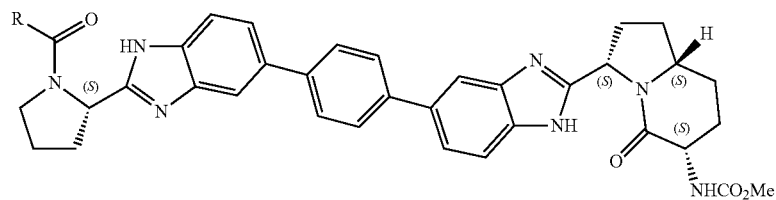
| Entry | 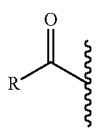 |
|---|---|
| 113 | 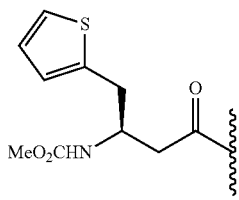 |
| 114 | 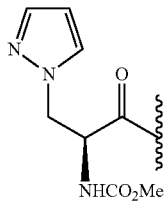 |
| 115 | 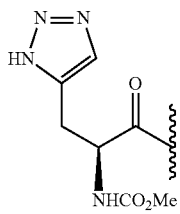 |
| 116 | 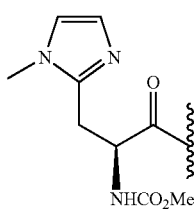 |
| 117 | 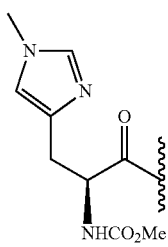 |

TABLE 1-continued
Examples 1-219.
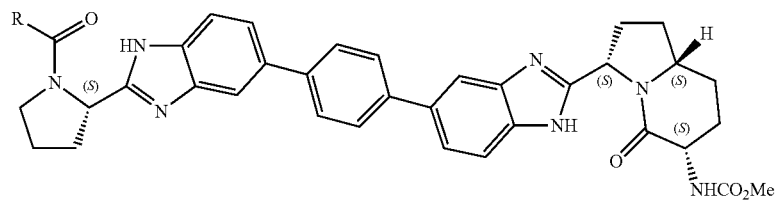
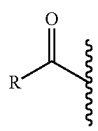
| Entry | |
|---|---|
| 118 | 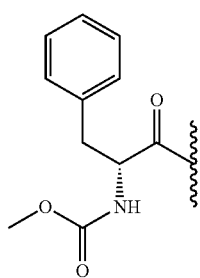 [SMILES: *C(=O)[C@@H](Cc1ccccc1)NC(=O)OC] |
| 119 | 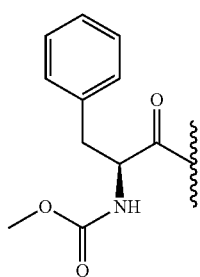 [SMILES: *C(=O)[C@H](Cc1ccccc1)NC(=O)OC] |
| 120 | 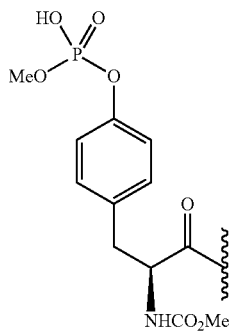 |
| 121 | 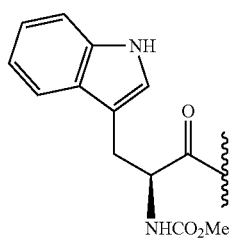 |

TABLE 1-continued
Examples 1-219.
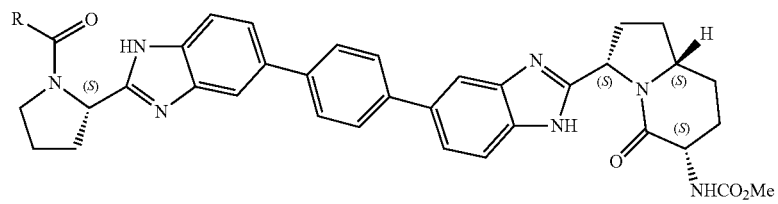
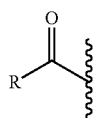
| Entry | |
|---|---|
| 122 | 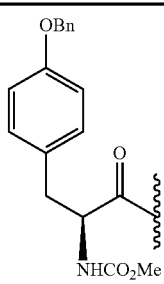 |
| 123 | 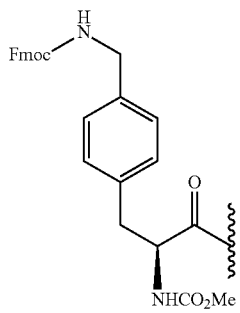 |
| 124 | 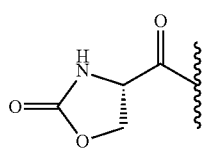 [SMILES: *C(=O)[C@@H]1COC(=O)N1] |
| 125 | 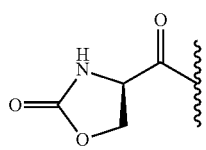 [SMILES: *C(=O)[C@H]1COC(=O)N1] |
| 126 | 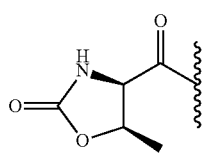 [SMILES: *C(=O)[C@@H]1NC(=O)O[C@@H]1C] |
| 127 | 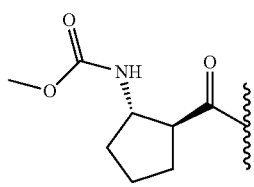 [SMILES: *C(=O)[C@H]1CCC[C@@H]1NC(=O)OC] |

TABLE 1-continued

Examples 1-219.

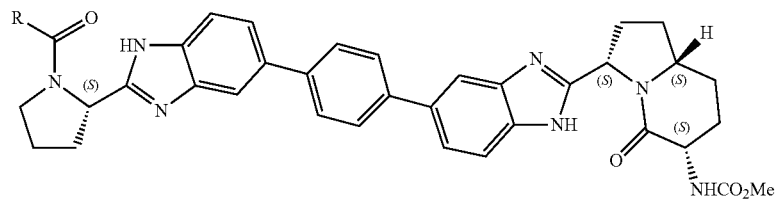

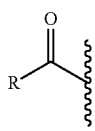

| Entry | |
|---|---|
| 128 | ![structure] methyl carbamate-NH on cyclopentane with ketone |
| 129 | ![structure] methyl carbamate-NH on cyclohexane with ketone |
| 130 | ![structure] methyl carbamate-HN on cyclopentane (1,3) with ketone |
| 131 | ![structure] methyl carbamate-HN (wedge) on cyclopentane (1,3) with ketone |
| 132 | ![structure] methyl carbamate-NH on cyclohexane (trans) with ketone |
| 133 | ![structure] benzyl, NH-CO-OMe, ketone |

TABLE 1-continued
Examples 1-219.
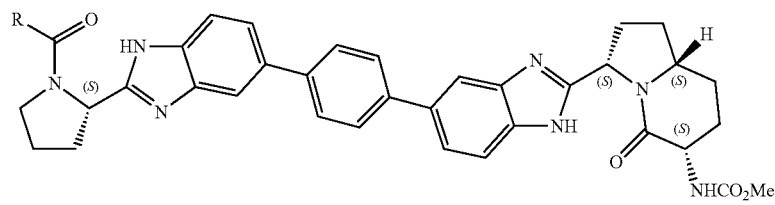
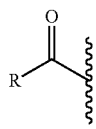
| Entry | |
|---|---|
| 134 | 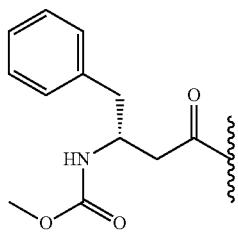 [SMILES: *C(=O)C[C@@H](Cc1ccccc1)NC(=O)OC] |
| 135 | 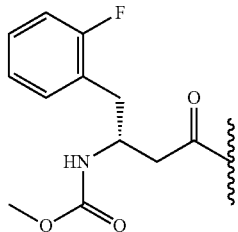 [SMILES: *C(=O)C[C@@H](Cc1ccccc1F)NC(=O)OC] |
| 136 | 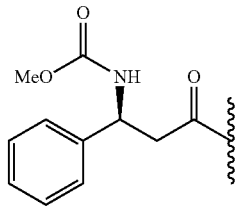 [SMILES: *C(=O)C[C@H](NC(=O)OC)c1ccccc1] |
| 137 | 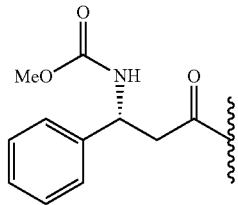 [SMILES: *C(=O)C[C@@H](NC(=O)OC)c1ccccc1] |
| 138 | 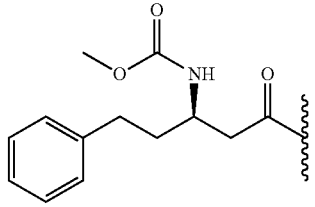 [SMILES: *C(=O)C[C@@H](CCc1ccccc1)NC(=O)OC] |

US 8,609,648 B2
TABLE 1-continued
Examples 1-219.
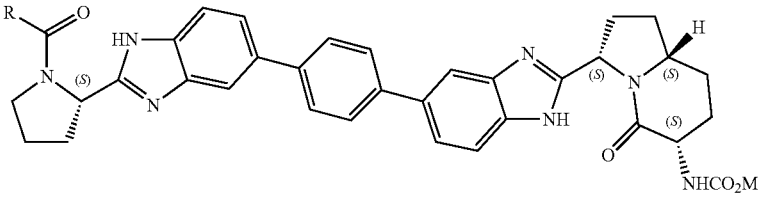
| Entry | |
|---|---|
| 139 | 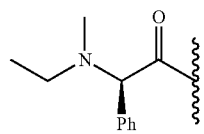 [SMILES: *C(=O)[C@@H](c1ccccc1)N(C)CC] |
| 140 | 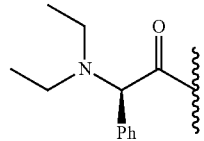 [SMILES: *C(=O)[C@@H](c1ccccc1)N(CC)CC] |
| 141 | 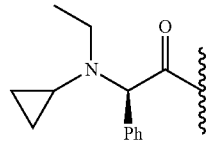 [SMILES: *C(=O)[C@@H](c1ccccc1)N(CC)C1CC1] |
| 142 | 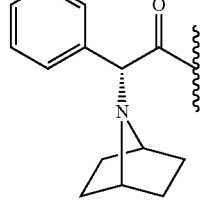 |
| 143 | 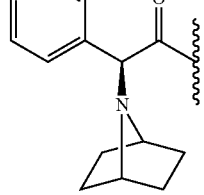 |
| 144 | 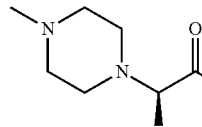 |
| 145 | 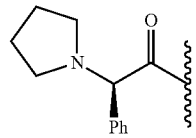 [SMILES: *C(=O)[C@@H](c1ccccc1)N1CCCC1] |

TABLE 1-continued
Examples 1-219.
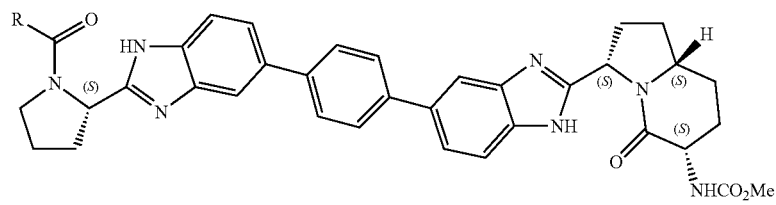
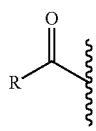
| Entry | |
|---|---|
| 146 | 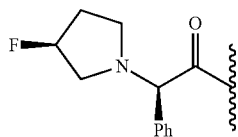 [SMILES: *C(=O)[C@@H](c1ccccc1)N1CC[C@H](F)C1] |
| 147 | 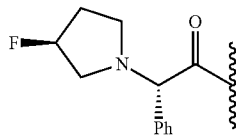 [SMILES: *C(=O)[C@H](c1ccccc1)N1CC[C@H](F)C1] |
| 148 | 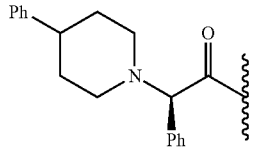 [SMILES: *C(=O)[C@@H](c1ccccc1)N1CCC(c2ccccc2)CC1] |
| 149 | 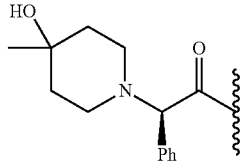 [SMILES: *C(=O)[C@@H](c1ccccc1)N1CCC(C)(O)CC1] |
| 150 | 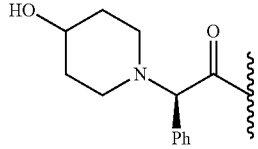 [SMILES: *C(=O)[C@@H](c1ccccc1)N1CCC(O)CC1] |
| 151 | 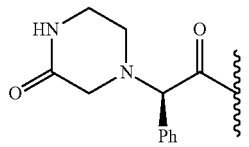 [SMILES: *C(=O)[C@@H](c1ccccc1)N1CCNC(=O)C1] |
| 152 | 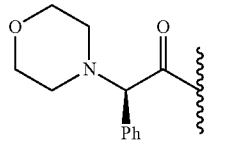 [SMILES: *C(=O)[C@@H](c1ccccc1)N1CCOCC1] |

TABLE 1-continued
Examples 1-219.
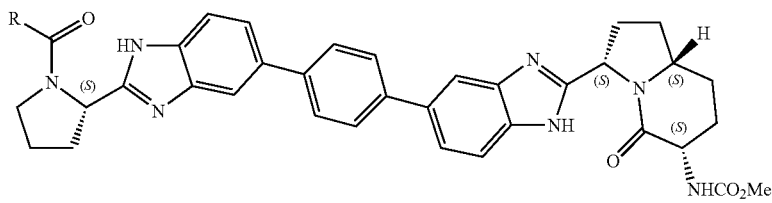
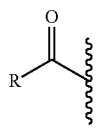
| Entry | |
|---|---|
| 153 | 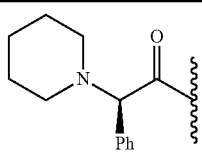 |
| 154 | 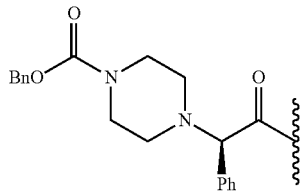 |
| 155 | 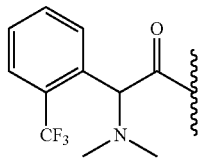 |
| 156 | 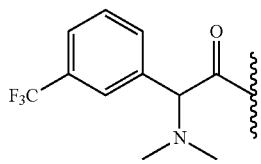 [SMILES: *C(=O)C(c1cccc(C(F)(F)F)c1)N(C)C] |
| 157 | 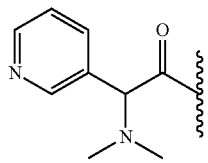 [SMILES: *C(=O)C(c1cccnc1)N(C)C] |
| 158 | 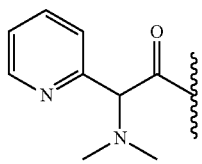 [SMILES: *C(=O)C(c1ccccn1)N(C)C] |
| 159 | 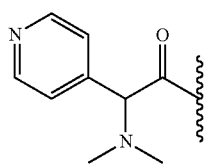 |

TABLE 1-continued
Examples 1-219.
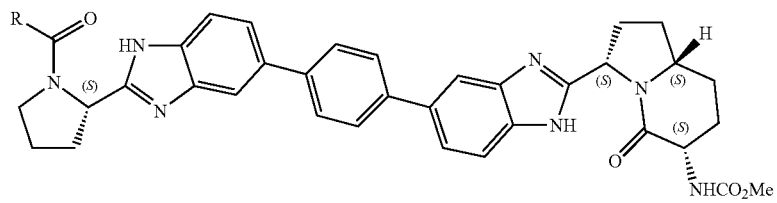
| Entry | |
|---|---|
| | 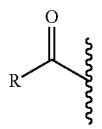 |
| 160 | 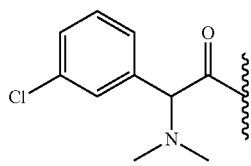 [SMILES: *C(=O)C(c1cccc(Cl)c1)N(C)C] |
| 161 | 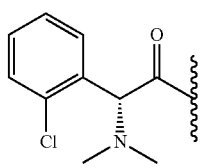 |
| 162 | 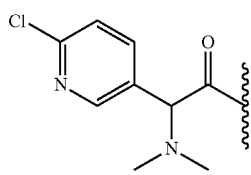 [SMILES: *C(=O)C(c1ccc(Cl)nc1)N(C)C] |
| 163 | 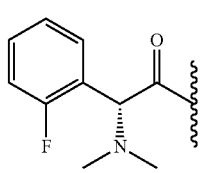 [SMILES: *C(=O)[C@@H](c1ccccc1F)N(C)C] |
| 164 | 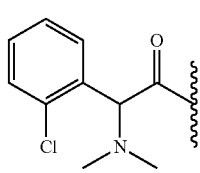 |
| 165 | 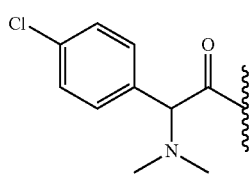 [SMILES: *C(=O)C(c1ccc(Cl)cc1)N(C)C] |
| 166 | 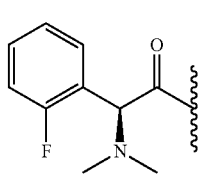 [SMILES: *C(=O)[C@H](c1ccccc1F)N(C)C] |

TABLE 1-continued

Examples 1-219.

| Entry | R group |
|---|---|
| 167 | 2-fluorophenyl-C(NMe₂)H-C(O)- |
| 168 | 3-fluorophenyl-C(NMe₂)H-C(O)- |
| 169 | (S)-2-fluorophenyl-C(piperidin-1-yl)H-C(O)- |
| 170 | 4-nitrophenyl-C(NMe₂)H-C(O)- |
| 171 | 2-methylthiazol-4-yl-C(NMe₂)H-C(O)- |
| 172 | benzo[d]isoxazol-3-yl-C(NMe₂)H-C(O)- |
| 173 | thiophen-2-yl-C(NMe₂)H-C(O)- |

TABLE 1-continued
Examples 1-219.
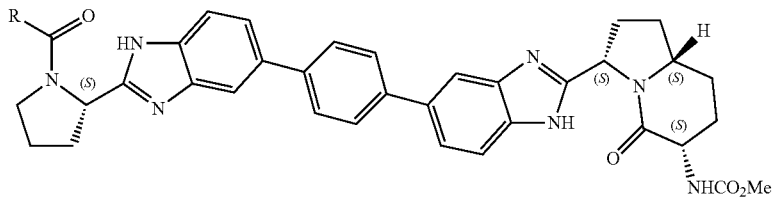
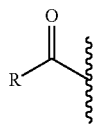
| Entry | |
|---|---|
| 174 | 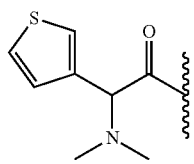 [SMILES: *C(=O)C(c1ccsc1)N(C)C] |
| 175 | 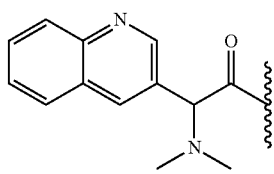 [SMILES: *C(=O)C(c1cnc2ccccc2c1)N(C)C] |
| 176 | 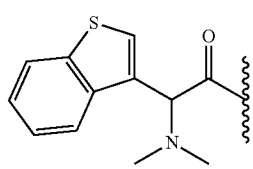 [SMILES: *C(=O)C(c1csc2ccccc12)N(C)C] |
| 177 | 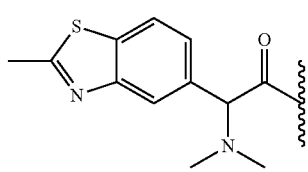 [SMILES: *C(=O)C(c1ccc2sc(C)nc2c1)N(C)C] |
| 178 | 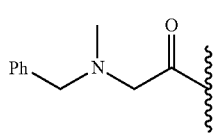 [SMILES: *C(=O)CN(C)Cc1ccccc1] |
| 179 | 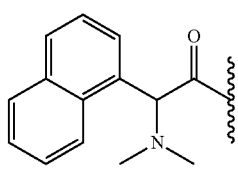 [SMILES: *C(=O)C(c1cccc2ccccc12)N(C)C] |
| 180 | 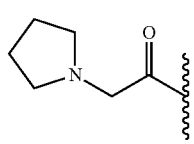 [SMILES: *C(=O)CN1CCCC1] |

TABLE 1-continued
Examples 1-219.
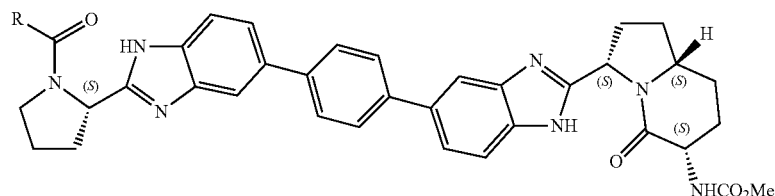
| Entry | R⟵O⟵ structure |
|---|---|
| 181 | 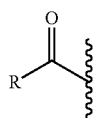 |
| 182 | 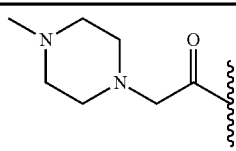 |
| 183 | 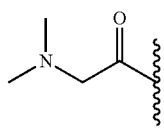 [SMILES: *C(=O)CN(C)C] |
| 184 | 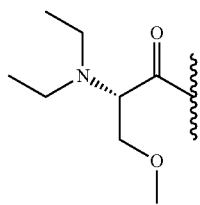 [SMILES: *C(=O)[C@H](COC)N(CC)CC] |
| 185 | 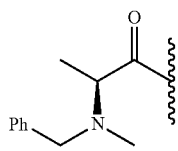 |
| 186 | 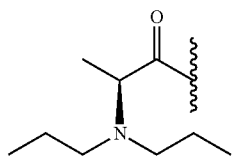 [SMILES: *C(=O)[C@H](C)N(CCC)CCC] |
| 187 | 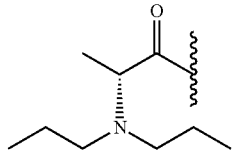 [SMILES: *C(=O)[C@@H](C)N(CCC)CCC] |
| 188 | 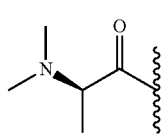 [SMILES: *C(=O)[C@@H](C)N(C)C] |

TABLE 1-continued
Examples 1-219.
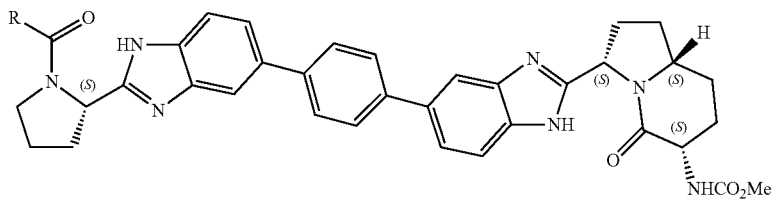
| Entry | |
|---|---|
| 189 | 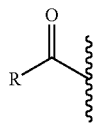 |
| 190 | 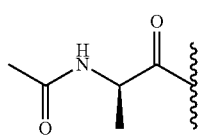 [SMILES: *C(=O)[C@@H](C)NC(C)=O] |
| 191 | 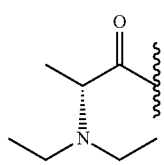 [SMILES: *C(=O)[C@@H](C)N(CC)CC] |
| 192 | 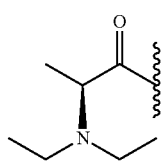 [SMILES: *C(=O)[C@H](C)N(CC)CC] |
| 193 | 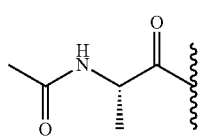 |
| 194 | 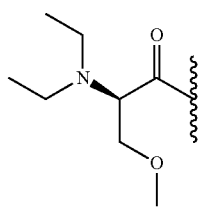 [SMILES: *C(=O)[C@@H](COC)N(CC)CC] |
| 195 | 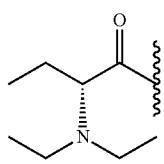 [SMILES: *C(=O)[C@@H](CC)N(CC)CC] |

TABLE 1-continued
Examples 1-219.
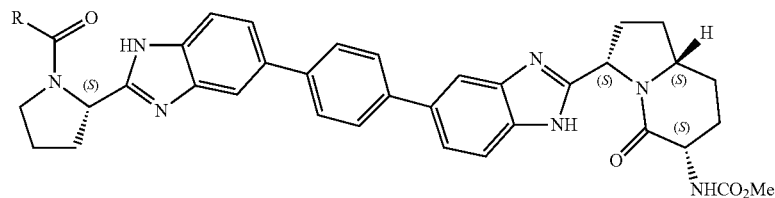
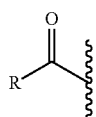
| Entry | |
|---|---|
| 196 | 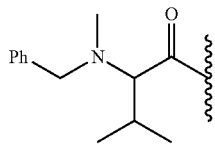 [SMILES: *C(=O)C(C(C)C)N(C)Cc1ccccc1] |
| 197 | 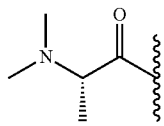 [SMILES: *C(=O)[C@H](C)N(C)C] |
| 198 | 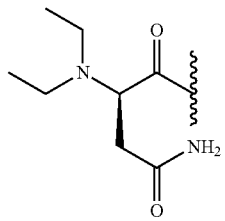 [SMILES: *C(=O)[C@@H](CC(N)=O)N(CC)CC] |
| 199 | 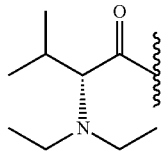 [SMILES: *C(=O)[C@@H](C(C)C)N(CC)CC] |
| 200 | 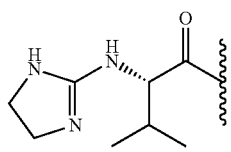 [SMILES: *C(=O)[C@@H](NC1=NCCN1)C(C)C] |
| 201 | 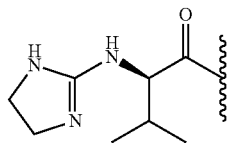 [SMILES: *C(=O)[C@H](NC1=NCCN1)C(C)C] |
| 202 | 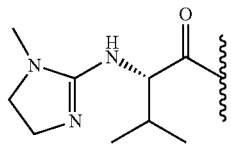 [SMILES: *C(=O)[C@@H](NC1=NCCN1C)C(C)C] |

TABLE 1-continued

Examples 1-219.

| Entry | R group |
|---|---|
| 203 | 3-amino-1-methyl-1,2,4-triazol-5-yl-NH-CH(iPr)-C(O)- |
| 204 | 4,5-dihydrothiazol-2-yl-NH-CH(iPr)-C(O)- |
| 205 | 5-amino-1H-1,2,4-triazol-3-yl-NH-CH(iPr)-C(O)- |
| 206 | pyridin-3-yl-NH-CH(iPr)-C(O)- |
| 207 | pyrimidin-4-yl-NH-CH(iPr)-C(O)- |
| 208 | 5-amino-1,2,4-oxadiazol-3-yl-NH-CH(iPr)-C(O)- |
| 209 | (Et)$_2$N-CH(tBu)-C(O)- |

TABLE 1-continued
Examples 1-219.
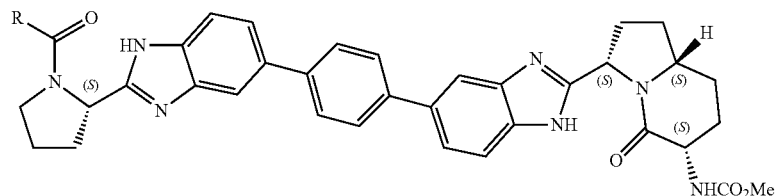
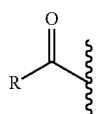
| Entry | |
|---|---|
| 210 | 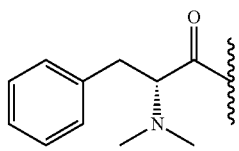 [SMILES: *C(=O)[C@@H](Cc1ccccc1)N(C)C] |
| 211 | 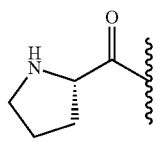 [SMILES: *C(=O)[C@@H]1CCCN1] |
| 212 | 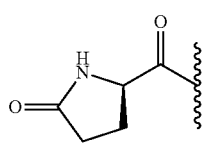 [SMILES: *C(=O)[C@H]1CCC(=O)N1] |
| 213 | 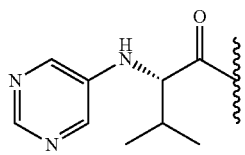 |
| 214 | 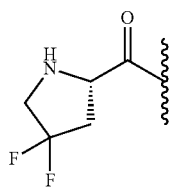 |
| 215 | 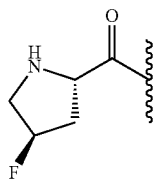 [SMILES: *C(=O)[C@@H]1C[C@@H](F)CN1] |
| 216 | 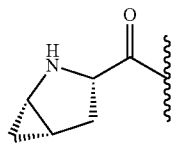 |

TABLE 1-continued
Examples 1-219.
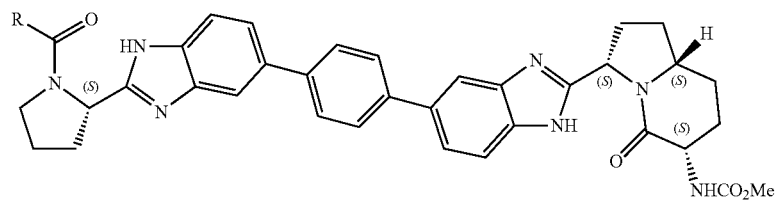
| Entry | 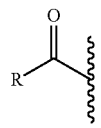 |
|---|---|
| 217 | 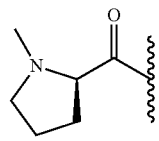 [SMILES: *C(=O)[C@H]1CCCN1C] |
| 218 | 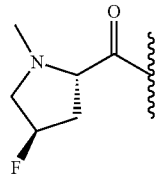 [SMILES: *C(=O)[C@@H]1C[C@@H](F)CN1C] |
| 219 | 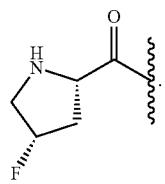 [SMILES: *C(=O)[C@@H]1C[C@H](F)CN1] |
TABLE 2
Examples 220-237
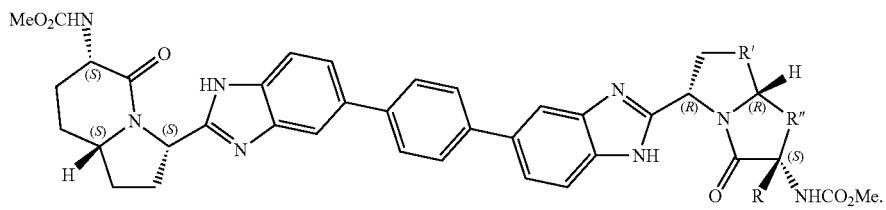
| Entry | R | R' | R" |
|---|---|---|---|
| 220 | H | $CH_2$ | $CH_2CH_2$ |
| 221 | H | $CH_2$ | $CH_2$ |
| 222 | Me | $CH_2$ | $CH_2CH_2$ |
| 223 | H | absent | $CH_2$ |
| 224 | H | O | $CH_2CH_2$ |
| 225 | H | $CH_2$ | absent |
| 226 | H | S | $CH_2CH_2$ |
| 227 | H | $CH_2$ | $OCH_2$ |
| 228 | H | O | $CH_2OCH_2$ |
| 229 | H | $CH_2$ | $SCH_2$ |
| 230 | H | S | $CH_2CMe_2$ |
| 231 | H | S | $CH_2SCH_2$ |
| 232 | H | $CH_2$ | $CH_2CH_2CH_2$ |
| 233 | H | $CH_2$ | $OCH_2CH_2$ |
| 234 | H | O | $CH_2CH_2CH_2$ |
| 235 | H | S | $CH_2CH_2CH_2$ |

TABLE 2-continued
Examples 220-237
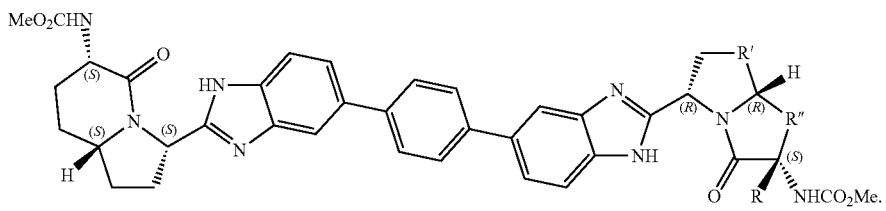
| Entry | R | R' | R'' |
|---|---|---|---|
| 236 | H | $CH_2$ | $CH_2CMe_2$ |
| 237 | $CHMe_2$ | O | $CH_2CH_2$. |
TABLE 3
Examples 238-247
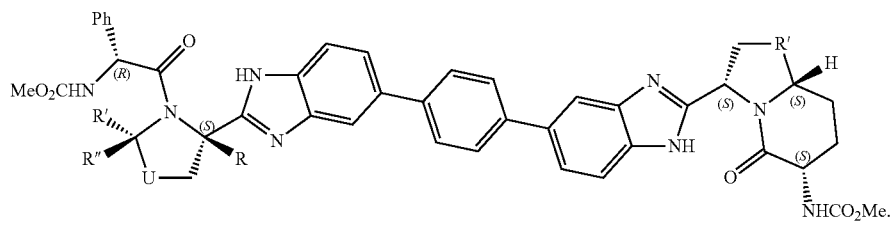
| Entry | R | R' | R'' | U |
|---|---|---|---|---|
| 238 | Me | H | H | $CH_2$ |
| 239 | H | H | H | $CF_2$ |
| 240 | Me | H | H | O |
| 241 | H | H | H | 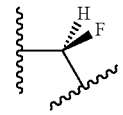 |
| 242 | Me | H | H | O |
| 243 | H | H | H | 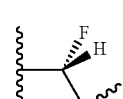 |
| 244 | H | Ph | H | $CH_2$ |
| 245 | H | H | H | 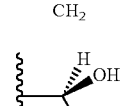 |
| 246 | H | H | Ph | $CH_2$ |
| 247 | H | H | H | 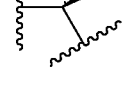 |

TABLE 4
Examples 248-251
248 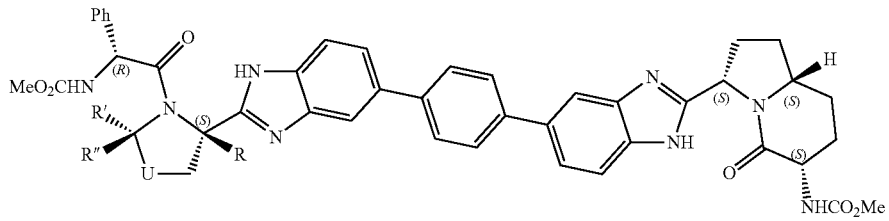
249 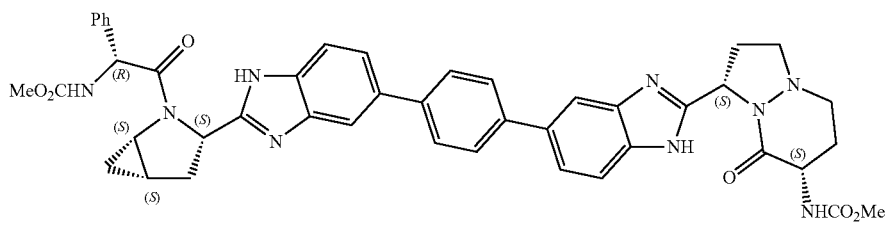
250 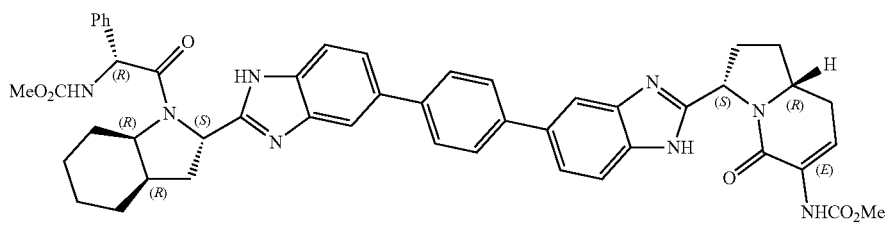
251 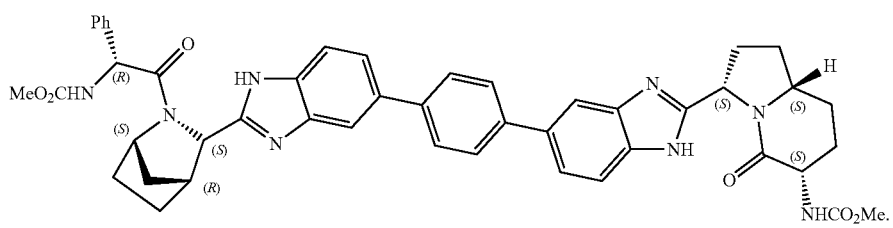
TABLE 5
Examples 252-261
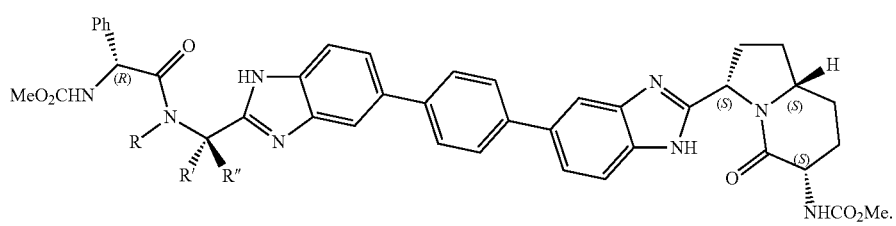
| Entry | R | R' | R" |
|---|---|---|---|
| 252 | Me | Me | H |
| 253 | H | Me | H |
| 254 | Me | H | Me |
| 255 | cyclopropyl | Me | H |
| 256 | Me | Allyl | H |
| 257 | Me | cyclopropyl | H |
| 258 | Me | Allyl | H |
| 269 | Et | Me | H |
| 260 | Me | CHMe$_2$ | H |
| 261 | Me | Et | H. |

TABLE 6
Examples 262-271
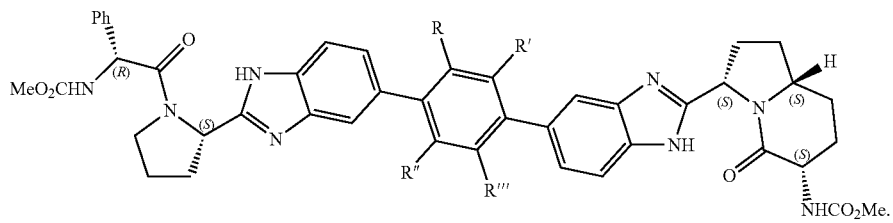
| Entry | R | R' | R" | R''' |
|---|---|---|---|---|
| 262 | F | H | H | H |
| 263 | F | F | H | H |
| 264 | Me | H | H | H |
| 265 | Me | Me | H | H |
| 266 | H | H | Me | Me |
| 267 | H | H | Et | Et |
| 278 | $CF_3$ | H | H | H |
| 269 | $CF_3$ | H | $CF_3$ | H |
| 270 | Cl | H | H | H |
| 271 | Cl | H | Cl | H. |
TABLE 7
Examples 272-289
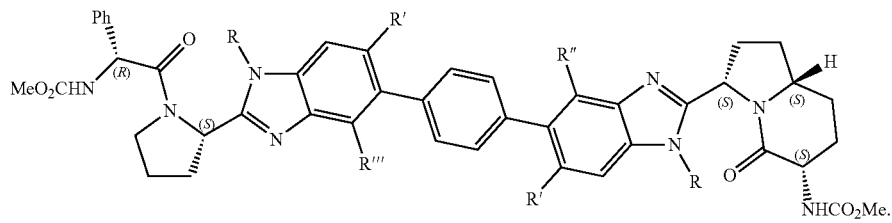
| Entry | R | R' | R" |
|---|---|---|---|
| 272 | Me | H | H |
| 273 | H | $CO_2H$ | H |
| 274 | H | F | H |
| 275 | H | H | $CO_2H$ |
| 276 | H | H | F |
| 277 | H | $CO_2Me$ | H |
| 278 | H | Cl | H |
| 279 | H | H | $CO_2Me$ |
| 280 | H | H | Cl |
| 281 | H | $CONH_2$ | H |
| 282 | H | Me | H |
| 283 | H | H | $CONH_2$ |
| 284 | H | H | Me |
| 285 | H | OMe | H |
| 286 | H | $CF_3$ | H |
| 287 | H | H | OMe |
| 288 | H | H | $CF_3$ |
| 289 | $CO_2Me$ | H | H. |

TABLE 8
Examples 290-319
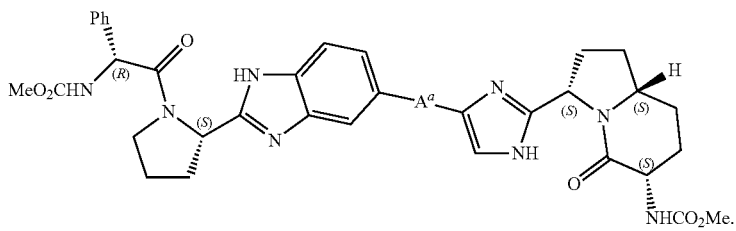
| Entry | Aa |
|---|---|
| 290 | (spiropentane-like bis-methylene) |
| 291 | 2,5-thiophenediyl-bis(methylene) |
| 292 | cyclopentene-1,2-diyl-bis(methylene) |
| 293 | 2,6-naphthalenediyl |
| 294 | quinoline-2,6-diyl |
| 295 | 1,4-phenylene-bis(methylene) |
| 296 | 4-(E-ethenyl)phenyl |
| 297 | 4-(ethynyl)phenyl |
| 298 | 1,4-phenylene |

TABLE 8-continued
Examples 290-319
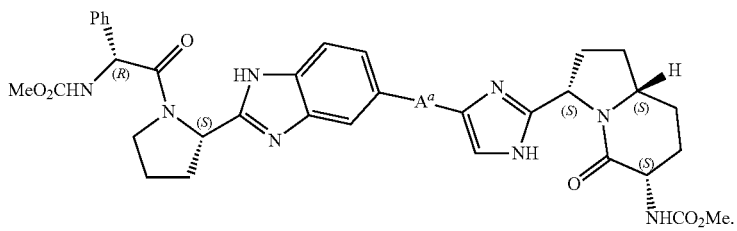
| Entry | Aa |
|---|---|
| 299 | (azetidine-pyridine linker) |
| 300 | (piperazine-pyrimidine linker) |
| 301 | (pyrazole-pyridine linker) |
| 302 | (biphenyl linker) |
| 303 | (thiophene-phenyl linker) |
| 304 | (isoindoline urea linker) |
| 305 | (O-cyclohexyl linker) |
| 306 | (piperidine-O linker) |
| 307 | (O-phenyl linker) |
| 308 | (trans-cyclohexyl linker) |

TABLE 8-continued
Examples 290-319
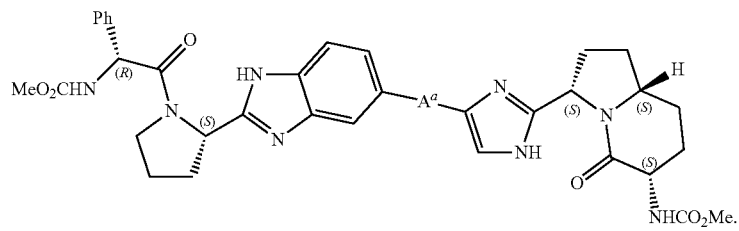
| Entry | Aa |
|---|---|
| 309 | ![4-xylylene] |
| 310 | ![piperazine-ethyl] |
| 311 | ![1,4-phenylene dioxy] |
| 312 | ![styryl-phenoxy] |
| 313 | ![1,4-phenylene dioxy stereo] |
| 314 | ![naphthalene-vinyl] |
| 315 | ![pyridine-2,5-diyl] |
| 316 | ![isoindole] |
| 317 | ![thiazole-ethyl] |

TABLE 8-continued
Examples 290-319
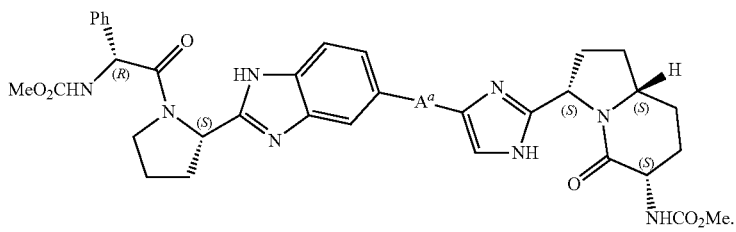
| Entry | Aa |
|---|---|
| 318 | 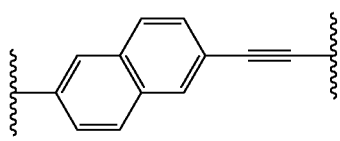 [SMILES: *C#Cc1ccc2cc(*)ccc2c1] |
| 319 | 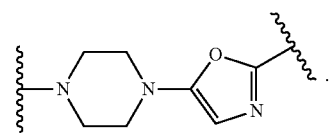 |
TABLE 9
Examples 320-343.
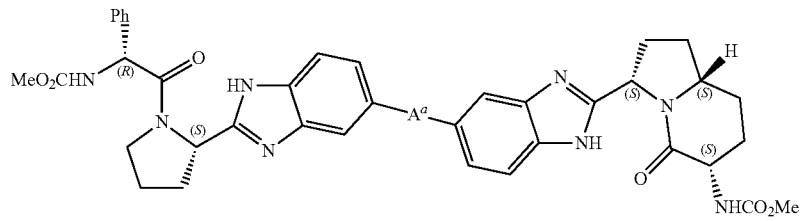
| Entry | Aᵃ | Entry | Aᵃ | Entry | Aᵃ |
|---|---|---|---|---|---|
| 320 | 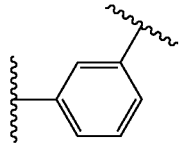 [SMILES: *c1cccc(*)c1] | 321 | 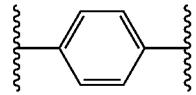 | 322 | 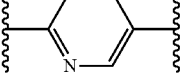 |
| 323 | 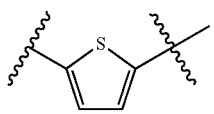 [SMILES: *c1ccc(*)s1] | 324 | 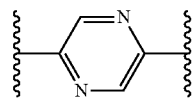 [SMILES: *c1cnc(*)cn1] | 325 | 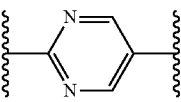 [SMILES: *c1cnc(*)nc1] |
| 326 | 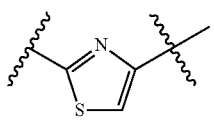 | 327 | 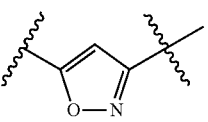 | 328 | 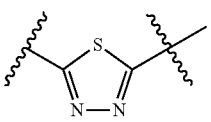 |
| 329 | 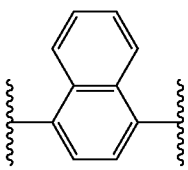 [SMILES: *c1ccc(*)c2ccccc12] | 330 | 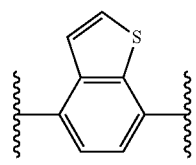 [SMILES: *c1ccc(*)c2sccc12] | 331 | 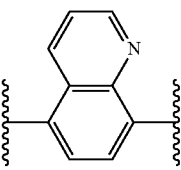 [SMILES: *c1ccc(*)c2ncccc12] |

TABLE 9-continued

Examples 320-343.

| Entry | A$^a$ | Entry | A$^a$ | Entry | A$^a$ |
|---|---|---|---|---|---|
| 332 | 2,6-naphthalene | 333 | benzothiazol-2,5-diyl | 334 | benzimidazol-1,5-diyl |
| 335 | 1,4-phenyl-vinylene | 336 | 2,7-naphthalene | 337 | quinoline-3,7-diyl |
| 338 | 2-oxo-1,4-pyridinediyl | 339 | 2-oxo-1,4-pyrimidinediyl | 340 | coumarin-3,7-diyl |
| 341 | 1,4-cyclohexyl | 342 | 1,4-phenyl-ethynylene | 343 | piperazine-1,4-diyl |

TABLE 10

Examples 344-355.

| Entry | y$^j$ | Entry | y$^j$ | Entry | y$^j$ |
|---|---|---|---|---|---|
| 344 | 1H-pyrazole-3,5-diyl | 345 | 1H-1,2,4-triazole-3,5-diyl | 346 | oxazole-2,5-diyl |

TABLE 10-continued
Examples 344-355.
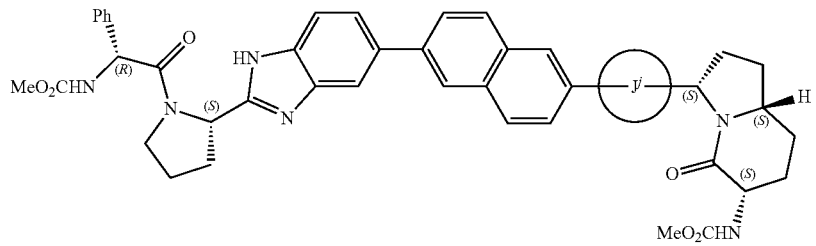
| Entry | y<sup>j</sup> | Entry | y<sup>j</sup> | Entry | y<sup>j</sup> |
|---|---|---|---|---|---|
| 347 | 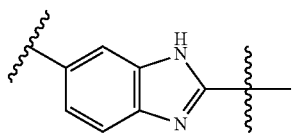 [SMILES: *c1ccc2nc(*)[nH]c2c1] | 348 | 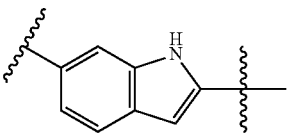 [SMILES: *c1ccc2cc(*)[nH]c2c1] | 349 | 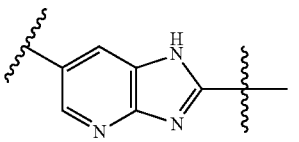 [SMILES: *c1cnc2nc(*)[nH]c2c1] |
| 350 | 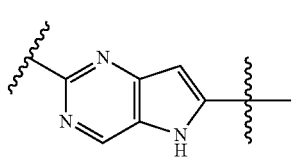 [SMILES: *c1ncc2[nH]c(*)cc2n1] | 351 | 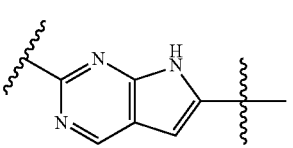 [SMILES: *c1ncc2cc(*)[nH]c2n1] | 352 | 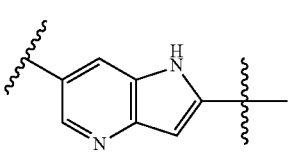 [SMILES: *c1cnc2cc(*)[nH]c2c1] |
| 353 | 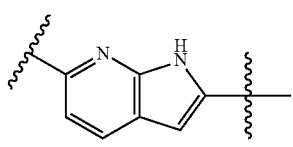 [SMILES: *c1ccc2cc(*)[nH]c2n1] | 354 | 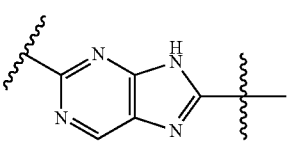 [SMILES: *c1ncc2nc(*)[nH]c2n1] | 355 | 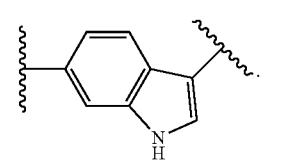 [SMILES: *c1ccc2c(*)c[nH]c2c1] |
TABLE 11
Examples 356-367.
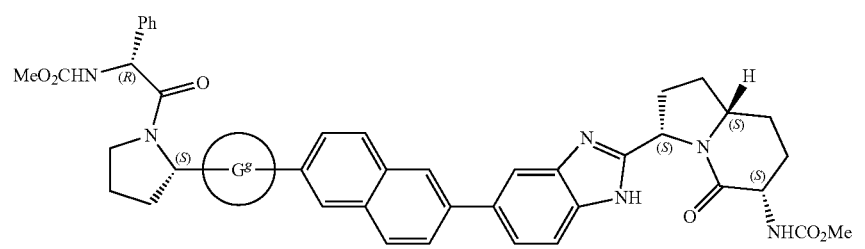
| Entry | G$^g$ | Entry | G$^g$ | Entry | G$^g$ |
|---|---|---|---|---|---|
| 356 | 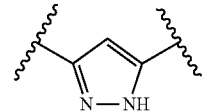 [SMILES: *c1cc(*)[nH]n1] | 357 | 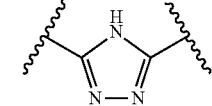 [SMILES: *c1nnc(*)[nH]1] | 358 | 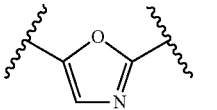 [SMILES: *c1cnc(*)o1] |
| 359 | 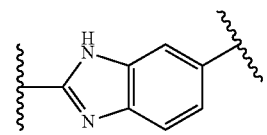 [SMILES: *c1ccc2nc(*)[nH]c2c1] | 360 | 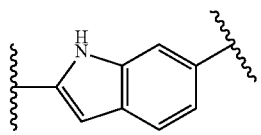 [SMILES: *c1ccc2cc(*)[nH]c2c1] | 361 | 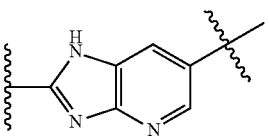 [SMILES: *c1cnc2nc(*)[nH]c2c1] |

TABLE 11-continued

Examples 356-367.

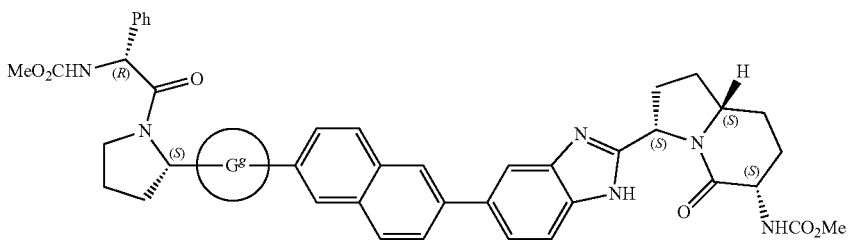

| Entry | G$^g$ | Entry | G$^g$ | Entry | G$^g$ |
|---|---|---|---|---|---|
| 362 | (pyrrolo[3,2-d]pyrimidine) | 363 | (pyrrolo[2,3-d]pyrimidine) | 364 | (pyrrolo[3,2-b]pyridine) |
| 365 | (pyrrolo[2,3-b]pyridine) | 366 | (imidazo[4,5-d]pyrimidine) | 367 | (indole) |

Example 368

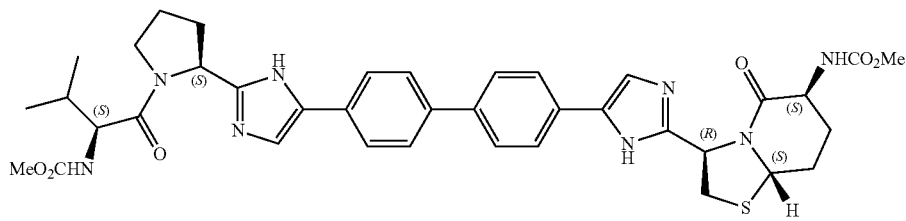

Step 368a. A suspension of (3R,6S,8aS)-6-{[(9H-fluoren-9-ylmethoxy)carbonyl]amino}-5-oxohexahydro-5H-[1,3]thiazolo[3,2-a]pyridine-3-carboxylic acid (0.300 g, 0.684 mmol) and 2,4'-dibromoacetophenone (0.200 g, 0.718 mmol) in CH$_3$CN (7 ml) was treated with DIPEA (0.24 mL, 1.368 mmol) at rt. The reaction mixture was stirred at rt for 2 hours. The volatiles were evaporated off and the residue was partitioned (EtOAc/CH$_2$Cl$_2$—H$_2$O). The aqueous layer was extracted with CH$_2$Cl$_2$. The combined organics were washed with brine, dried (Na$_2$SO$_4$), filtered and evaporated. The residue was purified by flash column chromatography (silica, CH$_2$Cl$_2$-ethyl acetate) to give the desired compound as a yellow solid (0.417 g, 96%). ESIMS m/z=634.71, 636.71 [M+H]$^+$.

Step 368b. A mixture of the compound from step 368a (0.380 g, 0.598 mmol) and ammonium acetate (0.507 g, 6.577 mmol) in xylenes (10 mL) was heated at 140° C. with a microwave for 80 minutes. The mixture was cooled down and combined with another batch started from 37.0 mg of the compound from step 1a. The combined mixture was evaporated. The residue was partitioned between CH$_2$Cl$_2$ and saturated aqueous NaHCO$_3$. The aqueous layer was extracted with CH$_2$Cl$_2$. The combined organics were dried (Na$_2$SO$_4$), filtered and evaporated. The residue was purified by flash column chromatography (silica, CH$_2$Cl$_2$-ethyl acetate with 1% Et$_3$N in ethyl acetate) to give the desired compound as a yellow foam (0.181 g, 45%). ESIMS m/z=614.90, 616.90 [M+H]$^+$.

Step 368c. A solution of the compound from step 368b (0.138 g, 0.224 mmol) in CH$_3$CN (3 ml) was treated with piperidine (0.066 mL, 0.672 mmol) at rt. The resulting suspension was stirred at rt for 40 minutes. The volatiles were evaporated off. The residue was purified by flash column chromatography (silica, CH$_2$Cl$_2$-MeOH with 1% Et$_3$N in CH$_2$Cl$_2$) to give the desired compound as a yellow solid (84.0 mg, 95%). ESIMS m/z=392.87, 394.87 [M+H]$^+$.

Step 368d. A suspension of the compound from step 368c (84.0 mg, 0.214 mmol) in THF (7 ml) and DIPEA (0.11 mL, 0.641 mmol) was treated with methyl chloroformate (0.017 mL, 0.224 mmol) at rt. The reaction mixture was stirred at rt for 20 minutes. The volatiles were evaporated off. The residue was taken up in MeOH (4 mL) and treated with K$_2$CO$_3$ (88.6 mg, 0.641 mmol) at rt. The suspension was stirred at rt for 5 minutes before being concentrated. The residue was taken up in CH$_2$Cl$_2$ and filtered through a short pad of Celite. The filtrate was directly purified by flash column chromatography (silica, hexanes-ethyl acetate with 15% MeOH and 1% Et$_3$N in ethyl acetate) to give the desired compound as a white foam (96.0 mg, 99%). ESIMS m/z=450.86, 452.86 [M+H]+.

Step 368e. A mixture of 2,4'-dibromoacetophenone (5.00 g, 18.0 mmol), N-Boc-L-proline (3.87 g, 18.0 mmol) and in CH₃CN (60 mL) was treated with TEA (5.40 mL, 37.8 mmol) at rt until the disappearance of the starting material. The volatiles were evaporated off and the residue was partitioned (EtOAc-water). The organics were washed with brine, dried (Na₂SO₄), filtered and evaporated. The residue was purified by chromatography (silica, hexanes-ethyl acetate) to give the desired compound as a light yellow foam (6.73 g, 91%). ¹H NMR (CDCl₃) 7.76 (t, J=8.0 Hz, 2H), 7.63 (dd, J=5.0, 8.5 Hz, 2H), 5.51, 5.16 (2 d, J=16.0 Hz, 1H), 5.32, 5.28 (2 d, J=16.5 Hz, 1H), 4.48, 4.40 (dd, J=5.0, 8.5 Hz, 1H), 3.56 (m, 1H), 3.43 (m, 1H), 2.30 (m, 2H), 2.06 (m, 1H), 1.92 (m, 1H), 1.46, 1.43 (2 s, 9H).

Step 368f. A solution of the compound from step 368e (6.73 g, 16.3 mmol) in toluene (100 mL) was treated with ammonium acetate (25.1 g, 0.327 mol) at 100° C. for 14 hours. The volatiles were evaporated off and the residue was partitioned (EtOAc-aqueous NaHCO₃). The organics were washed with brine, dried (Na₂SO₄), filtered and evaporated. The residue was purified by chromatography (silica, hexanes-ethyl acetate) to give the desired compound as a yellow foam (6.10 g, 95%). ESIMS m/z=392.24, 394.24 [M+H]+. ¹H NMR (CDCl₃) 7.57 (bs, 1H), 7.48 (m, 3H), 7.23 (s, 1H), 4.97 (m, 1H), 3.42 (m, 2H), 2.99 (m, 1H), 2.16 (m, 2H), 1.97 (m, 1H), 1.46 (s, 9H).

Step 368g. A mixture of the compound from step 368f (1.00 g, 2.55 mmol), bis(pinacolato)diboron (1.35 g, 5.33 mmol), Pd(PPh₃)₄ (0.147 g, 0.128 mmol) and potassium acetate (0.640 g, 6.53 mmol) in 1,4-dioxane (20 mL) was degassed and heated at 80° C. under N₂ for 14 hours. The volatiles were evaporated and the residue was partitioned (EtOAc-water). The organics were washed with brine, dried (Na₂SO₄), filtered and evaporated. The residue was purified by chromatography (silica, hexanes-ethyl acetate) to give the desired compound as a light yellow solid (0.978 g, 87%). ESIMS m/z=440.39 [M+H]+. ¹H NMR (CDCl₃) 11.03, 10.55 (2 s, 1H), 7.79 (m, 3H), 7.45 (m, 1H), 7.26 (m, 1H), 4.97 (m, 1H), 3.41 (m, 2H), 3.06, 2.91 (2 m, 1H), 2.17 (m, 2H), 1.97 (m, 1H), 1.49 (s, 9H), 1.35 (s, 12H).

Step 368h. A mixture of the compound from step 368d (96.0 mg, 0.213 mmol), the compound from step 368g (93.5 mg, 0.213 mmol), Pd(PPh₃)₄ (24.6 mg, 21.3 µmol) and NaHCO₃ (62.5 mg, 0.744 mmol) in DME (3 mL) and H₂O (1 mL) was degassed and heated at 98° C. under N₂ overnight. The mixture was cooled down and partitioned (EtOAc/CH₂Cl₂—H₂O). The aqueous layer was extracted with CH₂Cl₂. The combined organics were dried (Na₂SO₄), filtered and evaporated. The residue was purified by flash column chromatography (silica, hexanes-ethyl acetate with 20% MeOH and 1% Et₃N in ethyl acetate) to give the desired compound as a yellow solid (60.0 mg, 41%). ESIMS m/z=684.02 [M+H]+.

Step 368i. A solution of the compound from step 368h (60.0 mg, 0.0877 mmol) in 1,4-dioxane (1 mL) was treated with HCl in 1,4-dioxane (4 M, 4 mL) at rt for 1.5 hours. The volatiles were evaporated off to give the crude desired compound as a yellow solid, which was used directly in the next step.

Step 368j. A mixture of the crude compound from step 368i (0.0877 mmol at most) and (S)-2-(methoxycarbonylamino)-3-methylbutanoic acid (prepared according to WO 2008/021927, 15.4 mg, 0.0877 mmol) in DMF (2 mL) was treated with HATU (31.7 mg, 0.0834 mmol) in the presence of DIPEA (0.15 mL, 0.877 mmol) for 1.5 hours at rt. The volatiles were evaporated off. The residue was partitioned (EtOAc/CH₂Cl₂—H₂O). The organic layer was washed with saturated NaHCO₃ solution, brine, dried (Na₂SO₄), filtered and concentrated. The residue was purified by flash column chromatography (silica, hexanes-ethyl acetate with 20% MeOH and 1% Et₃N in ethyl acetate) to give the title compound as a yellow solid (43.7 mg, 67% over 2 steps). ESIMS m/z=741.51 [M+H]+.

Example 369

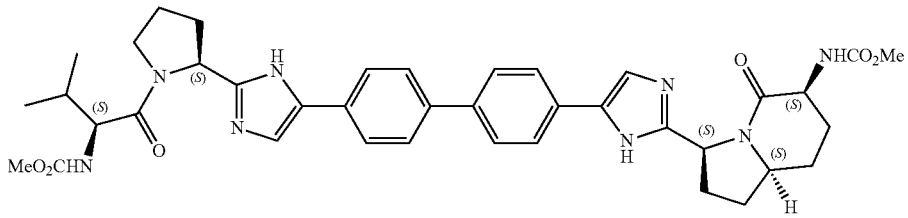

Step 369a. The desired compound benzyl (3S,6S,8aS)-3-(5-(4-bromophenyl)-1H-imidazol-2-yl)-5-oxooctahydroindolizin-6-ylcarbamate was prepared from (3S,6S,8aS)-6-(benzyloxycarbonyl-amino)-5-oxooctahydroindolizine-3-carboxylic acid (prepared according to Tetrahedron. 2000, 56, 4289) and 2,4'-dibromoacetophenone using procedures similar to that described in steps 368a-368f and WO 2008/021927. ESIMS m/z=509.92 [M+H]+.

Step 369b. The desired compound methyl (S)-1-((S)-2-(5-(4-bromophenyl)-1H-imidazol-2-yl)pyrrolidin-1-yl)-3-methyl-1-oxobutan-2-ylcarbamate was prepared from the compound of step 368f using procedures similar to that described in steps 368i and 368j. ESIMS m/z=449.12 [M+H]+.

Step 369c. The desired compound methyl (S)-3-methyl-1-oxo-1-((S)-2-(5-(4-(4,4,5,5-tetramethyl-1,3,2-dioxaborolan-2-yl)phenyl)-1H-imidazol-2-yl)pyrrolidin-1-yl)butan-2-ylcarbamate was prepared from compound of step 369b using procedure similar to that described in step 368g. ESIMS m/z=497.19 [M+H]+.

Step 369d. Into a mixture of compound from step 369a (33 mg, 0.0765 mmol) and the compound from step 369c (39 mg, 0.078 mmol) in 1,2-dimethoxyethane (2 mL) and water (1 mL) was added Pd(PPh₃)₄ (7.5 mg, 0.007 mmol) and NaHCO₃ (33 mg, 0.49 mmol). The resulting mixture was stirred at 85° C. under nitrogen atmosphere for 3 hours before being partitioned (water-EtOAc). The organics was dried (Na₂SO₄) and concentrated to afford a brown slurry, which was chromatographed (silica, dichloromethane-methanol) to give the desired product as a light yellow solid (28 mg, 51%). ESIMS m/z=799.43 [M+H]+.

Step 369e. Into a mixture of compound from step 369d (28 mg, 0.035 mmol) in methanol (3 mL) was added palladium (0) on carbon (10 wt %, 10 mg) and hydrochloric acid (4N in water, 0.3 mL). The mixture was stirred under hydrogen (60 psi) for 12 hours before being filtered through Celite. The volatiles were removed by rotavap to afford the crude desired compound, which was used for the next step without further purification. ESIMS m/z=665.38 [M+H]$^+$.

Step 369f. In a mixture of compound from step 369e (0.035 mmol at most) in THF (3 mL) was added diisopropylethylamine (0.3 mL) and methyl chloroformate (0.05 mL). The mixture was stirred at rt for 1 hour before all volatiles were removed by rotavap. The residue was redissolved in methanol (2 mL) before being added potassium carbonate (20 mg). The mixture was stirred at rt for another 20 minutes and was filtered and concentrated to afford a brown oil, which was purified by HPLC(C-18, methanol-water) to afford the title compound as white solid (1.2 mg, 4.8% over 3 steps). ESIMS m/z=723.38 [M+H]$^+$.

Example 370

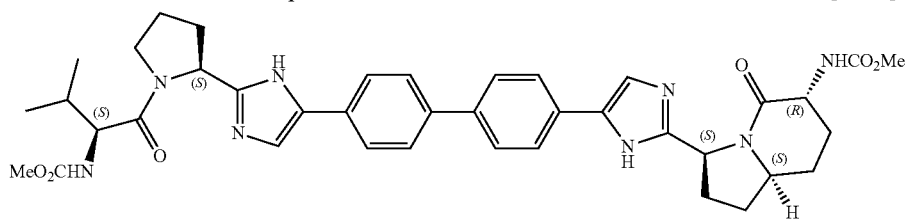

The title compound was prepared from compound (3S,6R,8aS)-6-(benzyloxycarbonylamino)-5-oxooctahydroindolizine-3-carboxylic acid (prepared according to *Tetrahedron.* 2000, 56, 4289) using procedures similar to that described in example 369. ESIMS m/z=723.37 [M+H]$^+$.

Example 371

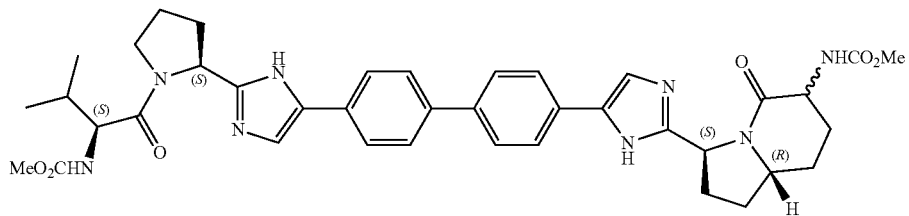

The title compounds were prepared as an 1:1 diastereomeric mixture from compound (3S,6S/R,8aR)-6-(methoxycarbonylamino)-5-oxooctahydroindolizine-3-carboxylic acid (prepared according to *Tetrahedron.* 2000, 56, 4289) using procedures similar to that described in example 369. ESIMS m/z=723.39 [M+H]$^+$.

Example 372

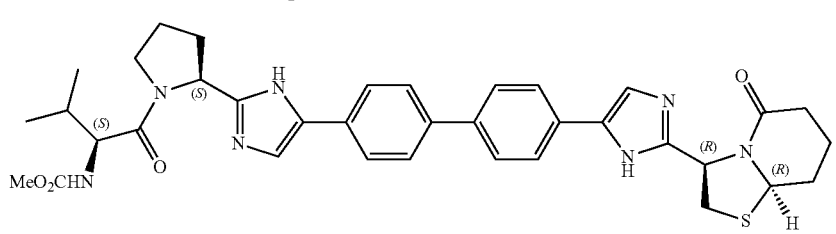

Step 372a. A solution of methyl 5-chloro-5-oxopentanoate (4.2 mL, 30 mmol) and 2,6-lutidine (3.85 ml, 33 mmol) in THF (60 ml) was charged Pd on carbon (5%, 1.0 g). It was stirred at rt under H$_2$ (30 psi) for 2 days and then filtered through Celite. The filtrate was concentrated and the residue was dissolved in methylene chloride and washed with water. The organics were dried (Na$_2$SO$_4$) and concentrated to give an aldehyde intermediate (4 g) as a pale yellow oil.

A solution of L-Cys-OMe.HCl (3.75 g, 21.8 mmol) in water (15 ml) and EtOH (10 ml) was charged NaHCO$_3$ (1.85 g, 22 mmol) and a solution of the above aldehyde (2.93 g, 22.5 mmol) in EtOH (15 ml). The mixture was stirred at rt for 2 hours and concentrated. The residue was dissolved in methylene chloride and washed with water. The organic layer was dried (Na$_2$SO$_4$) and concentrated. Column purification (EtOAc/hexanes 20% to 70%) gave a clear light yellow oil. This oil was dissolved in toluene (100 ml) and stirred at 105° C. for 18 hours. Removal of solvent followed by column purification afforded desired minor product (0.26 g), ESIMS m/z=216.05 [M+H]$^+$; and desired major product (2.1 g), ESIMS m/z=216.05 [M+H]$^+$.

Step 372b. A solution of the desired minor compound from step 372a (0.26 g, 1.21 mmol) in THF/MeOH (2:1, 4 ml) was treated with aqueous LiOH (1 M, 2.5 ml) for 16 hours at rt before being concentrated. The aqueous residue was acidified with 1 N HCl to pH 1 and saturated with ammonium chloride and extracted with EtOAc three times. The combined organics were concentrated to dryness. The white residue and 2,4'-Dibromoacetophenone (358 mg, 1.29 mmol) were dissolved in acetonitrile (10 ml). Diisopropyl ethyl amine (0.35 ml, 2.01 mmol) was added and the reaction mixture was stirred at rt for 16 hours and then concentrated. The residue was partioned (EtOAc-saturated NaHCO$_3$). The organics were dried (Na$_2$SO$_4$) and evaporated, followed by column purification (EtOAc/hexanes 1:2 to 2:1) to afford the desired product (370 mg, 77% yield for 2 steps) as an off-white solid. ESIMS m/z=398.06 [M+H]$^+$.

Step 372c. A solution of the compound from step 372b (358 mg, 0.9 mmol) in toluene (10 ml) was heated with ammonium acetate (1.43 g, 18.5 mmol) at 95° C. for 20 hours and then concentrated. The residue was partioned (EtOAc-saturated NaHCO$_3$). The organics were dried (Na$_2$SO$_4$) and evaporated, followed by column purification (EtOAc/hexanes 1:1 to 5:1) to afford the desired product (290 mg, 85% yield) as an off-white foam. ESIMS m/z=378.01 [M+H]$^+$.

Step 372d. A solution of the compound from step 372c (105 mg, 0.28 mmol) and the compound from step 368g (130 mg, 0.30 mmol) in DME/H$_2$O (3:1, 8 ml) was charged NaHCO$_3$ (80 mg, 0.95 mmol) and Pd(PPh$_3$)$_4$ (51 mg, 0.044 mmol). It was degassed before being stirred at 90° C. for 18 hours. It was partioned (EtOAc-saturated NaHCO$_3$). The organics were dried (Na$_2$SO$_4$) and evaporated, followed by column purification (EtOAc/hexanes 1:1 to 5:1) to afford the desired product 61 mg (36% yield) as a yellow foam. ESIMS m/z=611.23 [M+H]$^+$.

Step 372e. A solution of the compound from step 372d (59 mg, 0.097 mmol) in CH$_2$Cl$_2$ (1 ml) was treated with HCl in dioxane (4 M, 3 ml) at rt for 1.5 hours and then concentrated to dryness. The resulting yellow solid and (S)-2-(methoxycarbonylamino)-3-methylbutanoic acid (prepared according to WO 2008/021927, 19 mg, 0.11 mmol) were dissolved in DMF (1.5 ml). Diisopropylethyl amine (0.2 ml, 1.15 mmol) was added followed by HATU (37.5 mg, 0.099 mmol). The mixture was stirred at rt for 0.5 hour. The residue was partioned (EtOAc-saturated NaHCO$_3$). The organics were dried (Na$_2$SO$_4$) and evaporated, followed by reverse phase preparative HPLC purification afforded the title compound (57 mg, 88% yield for 2 steps) as a white solid. ESIMS m/z=668.33 [M+H]$^+$.

Example 373

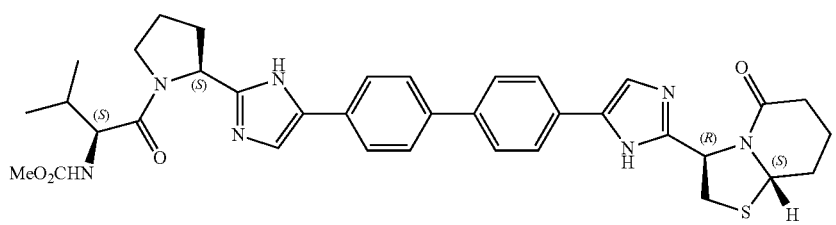

The title compound (10 mg as a white solid) was prepared from the desired major product in step 372a using procedures similar to that described in steps 372b-372e. ESIMS m/z=668.27 [M+H]$^+$.

Example 374

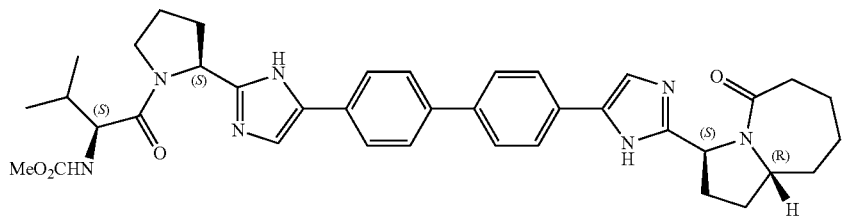

Step 374a. A solution of ethyl L-pyroglutamate (2.2 g, 14 mmol) and Boc$_2$O (4 g, 18 mmol) in methelene chloride (30 ml) was charged DMAP (1.7 g, 14 mmol) in portions. The mixture was stirred at rt for 1 hour. It was partioned (EtOAc-saturated NaHCO$_3$). The organics were dried (Na$_2$SO$_4$) and evaporated, followed by column purification (EtOAc/hexanes 2:1) gave a light yellow solid. This yellow solid was dissolved in methylene chloride (30 ml) and cooled to −78° C. DIBAL (1 M, 30 ml) was added dropwise. After 1 hour, isopropanol (2 ml) was added and the cooling batch was removed. The reaction mixture was concentrated and the residue was dissolved in EtOAc and washed with water twice. The organic was dried (Na$_2$SO$_4$) and concentrated to dryness. The residue was dissolved in EtOH (50 ml) and TsOH (50 mg) was added. The reaction mixture was stirred at room temperature for 17 hours and then concentrated. Column purification (EtOAc/hexanes 1:5 to 1:1) afforded the desired product 2.8 g (70% yield for 3 steps) as a clear oil.

Step 374b. A solution of the compound from step 374a (5.0 g, 17.4 mmol) and allyltrimethylsilane (4.97 g, 43.5 mmol) in methylene chloride (50 ml) at −78° C. was treated with BF$_3$OEt$_2$ (4.4 ml, 35 mmol) for 2 hours before water (5 ml) was added. It was partioned (EtOAc-saturated NaHCO$_3$). The organics were dried (Na$_2$SO$_4$) and evaporated, followed by column purification (EtOAc/hexanes 0-40%) afforded the desired C-allylated intermediate (3.4 g, 69% yield) as a clear oil. This oil (1.06 g, 3.74 mmol) and (E)-methyl pent-3-enoate (1.79 g, 15.68 mmol) were dissolved in methylene chloride (100 ml). Hovada-Grubbs 2nd generation catalyst (0.23 g, 0.37 mmol) was added and the reaction mixture was stirred at 40° C. for 6 hours. The solvent was removed and the residue was purified by column chromatography to afford the desired product 1.02 g (77% yield) as a yellow oil. ESIMS m/z=256.15 [M+H-Boc]$^+$.

Step 374c. A solution of the compound from step 374b (1.0 g, 2.81 mmol) in EtOAc (10 ml) was charged Pd/C (5%, 0.3 g) and the mixture was stirred at rt under H$_2$ (30 psi) for 2 hours. Silica gel filtration followed by removal of solvent gave a clear oil. This oil was treated with HCl in dioxane (4 M, 4 ml) and the reaction mixture was stirred at room temperature for 2 hours. Solvent was removed and the residue was dissolved in EtOAc and passed through a NaHCO₃ short column. The filtrated was concentrated to dryness. The residue was dissolved in toluene (10 ml) and stirred at 105° C. for 3 days. Removal of solvent followed by column purification afforded the desired product 108 mg (32% yield for 3 steps) as a white solid. ESIMS m/z=226.16 [M+H]⁺.

Step 374d. The desired compounds (2 isomers, 160 mg, 90% yield, as an off-white solid) was obtained from the compound of step 374c (108 mg, 0.48 mmol) using procedures similar to that described in step 5b. ESIMS m/z=394.03 [M+H]⁺.

Step 374e. A solution of the compounds from step 374d (160 mg, 0.41 mmol) in toluene (5 ml) was treated with ammonium acetate (0.65 g, 8.4 mmol) at 95° C. for 20 hours and then concentrated. It was partioned (EtOAc-saturated NaHCO₃). The organics were dried (Na₂SO₄) and evaporated, followed by column purification (EtOAc/hexanes 1:1 to 5:1) afforded the desired major product (110 mg) as off-white solid, ESIMS m/z=374.22 [M+H]⁺; and the desired minor product (20 mg) as off-white solid. ESIMS m/z=374.22 [M+H]⁺.

Step 374e. The desired compound (11 mg, as a yellow foam, 57% yield) was obtained from the minor compound of step 374d (12 mg, 0.032 mmol) and the compound from step 1g (15 mg, 0.034 mmol) using procedures similar to that described in step 372d. ESIMS m/z=607.37 [M+H]⁺.

Step 374f. The title compound (6 mg, as a white solid, 50% yield two steps) was obtained from the compound of step 374e (11 mg, 0.018 mmol) using procedures similar to that described in step 372e. ESIMS m/z=664.59 [M+H]⁺.

Example 375

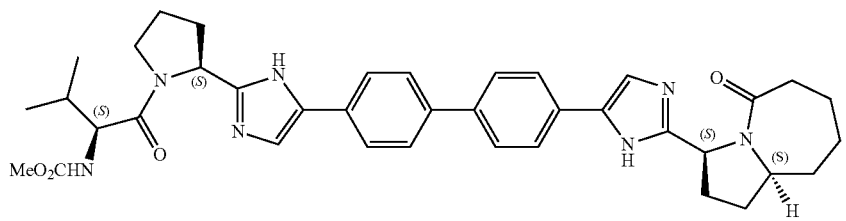

The title compound (28 mg, as an off-white solid, 33% yield three steps) was obtained from the major compound of step 374d (36 mg, 0.096 mmol) using procedures similar to that described in steps 374e and 374f. ESIMS m/z=664.26 [M+H]⁺.

Example 376

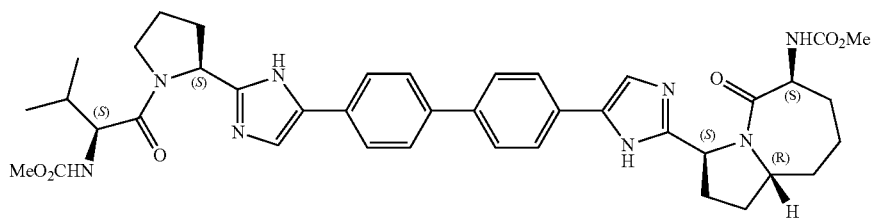

Step 376a. CuBr.Me₂S (4.93 g, 24 mmol) was suspended in THF (55 ml) and cooled to −40° C. (Z)-prop-1-enylmagnesium bromide (0.5 M in THF, 48 ml, 24 mmol) was added dropwise. After 45 minutes the resulting solution was further cooled to −78° C. and BF₃.OEt₂ (3 ml, 24 mmol) was added dropwise. After 30 minutes a THF (10 ml) solution of the starting material (1.76 g, 6.12 mmol) was added and the cooling batch was removed after 30 minutes. After 3 hours a 1:1 mixture (20 ml) of aqueous NH₄Cl(sat) and ammonia was added. After 2 hours the layers were separated. The aqueous layer was extracted with EtOAc twice. The combined organic layers were dried over Na₂SO₄ and concentrated. Column purification afforded the desired product 440 mg (25% yield) as a light yellow oil.

Step 376b. The compound from step 376a (440 mg, 1.55 mmol) was treated with HCl in dioxane (4 M, 3 ml) at room temperature for 1.5 hours and then concentrated to dryness. The resulting yellow solid and (S)-2-(tert-butoxycarbonylamino)pent-4-enoic acid (622 mg, 1.57 mmol) were dissolved in DMF (8 ml). Diisopropylethyl amine (0.9 ml, 5.16 mmol) was added followed by HATU (587 mg, 1.54 mmol). The reaction mixture was stirred at room temperature for an hour. It was partioned (EtOAc-saturated NaHCO₃). The organics were dried (Na₂SO₄) and evaporated, followed by column purification (EtOAc/hexanes 1:5 to 1:2) afforded the desired product 435 mg (73% yield for 2 steps) as a light yellow oil. ESIMS m/z=281.25 [M+H-Boc]⁺.

Step 376c. The compound from step 376b (425 mg, 1.12 mmol) was dissolved in methylene chloride (120 ml). Hovada-Grubbs 2nd generation catalyst (55 mg, 0.088 mmol) was added and the reaction mixture was stirred at 40° C. for 20 hours. The solvent was removed and the greenish oily residue was dissolved in EtOAc (10 ml). Pd/C (5%, 0.3 g) was added and the mixture was stirred at room temperature under H₂ (20 psi) for 16 hours. Silica gel filtration followed by removal of solvent and column purification (EtOAc/hex 1:5 to 2:1) afforded the desired product 322 mg (85% yield for 2 steps) as a yellow oil. ESIMS m/z=241.20 [M+H-Boc]⁺.

Step 376d. The compound from step 376c (315 mg, 0.93 mmol) was dissolved in THF/MeOH (2:1, 6 ml). Aqueous LiOH (1 M, 3 ml) was added. The reaction mixture was stirred for 16 hours at room temperature, and then concentrated to remove volatiles. The aqueous residue was acidified with 1 N hydrochloric acid to pH 1. The aqueous was saturated with ammonium chloride and extracted with EtOAc three times. The organic phases were combined and concentrated to dryness. The brown residue and 2,4'-Dibromoacetophenone (310 mg, 1.12 mmol) were dissolved in acetonitrile (10 ml). Diisopropyl ethyl amine (0.5 ml, 2.87 mmol) was added and the reaction mixture was stirred at room temperature for 16 hours and then concentrated. Standard EtOAc/NaHCO3(sat) workup followed by column purification (EtOAc/hex 1:2 to 2:1) gave a brown oil. This brown oil was dissolved in toluene (10 ml) and ammonium acetate (0.65 g, 8.4 mmol) was added. The mixture was stirred at 95° C. for 14 hours and then concentrated. It was partioned (EtOAc-saturated NaHCO$_3$). The organics were dried (Na$_2$SO$_4$) and evaporated, followed by column purification (EtOAc/hexanes 1:1 to 5:1) afforded the desired product 52 mg (15% yield for 3 steps) as a yellow solid. ESIMS m/z=489.05 [M+H]$^+$.

Step 376e. The compound from step 376d (52 mg, 0.11 mmol) was treated with HCl in dioxane (4 M, 3 ml) at room temperature for 1.5 hours and then concentrated to dryness. The resulting yellow solid was dissolved in THF (3.5 ml). DIPEA (0.1 ml, 0.57 mmol) was added followed by methyl chloroformate (2 drops). The reaction mixture was stirred at room temperature for 20 minutes and concentrated. The residue was dissolved in MeOH (3 ml) and K$_2$CO$_3$ (10 mg) was added at room temperature. After 3 minutes the reaction mixture was concentrated followed by column purification to afford the desired product 44 mg (93% yield for 2 steps) as an off-white solid. ESIMS m/z=446.98 [M+H]$^+$.

Step 376f. The compound from step 376e (44 mg, 0.098 mmol) and the compound from step 368g (44 mg, 0.1 mmol) were dissolved in DME/H$_2$O (3:1, 4 ml). Sodium bicarbonate (28 mg, 0.34 mmol) was added. The resulting mixture was degassed by bubbling dry nitrogen through. Tetrakis(triphenylphosphine)palladium(0) (17.5 mg, 0.015 mmol) was added and the reaction mixture was stirred at 90° C. for 18 hours. It was partioned (EtOAc-saturated NaHCO$_3$). The organics were dried (Na$_2$SO$_4$) and evaporated, followed by column purification (EtOAc/hexanes 1:1 to 5:1) afforded the desired product 37 mg (55% yield) as a yellow foam. ESIMS m/z=680.02 [M+H]$^+$.

Step 376g. The compound from step 376f (37 mg, 0.054 mmol) was dissolved in methylene chloride (1 ml). HCl in dioxane (4 M, 3 ml) was added. The reaction mixture was stirred at room temperature for 1.5 hours and then concentrated to dryness. The resulting yellow solid and (S)-2-(methoxycarbonylamino)-3-methylbutanoic acid (prepared according to WO 2008/021927, 10 mg, 0.057 mmol) were dissolved in DMF (1.5 ml). Diisopropylethyl amine (0.05 ml, 0.29 mmol) was added followed by HATU (21 mg, 0.055 mmol). The reaction mixture was stirred at room temperature for half an hour. It was partioned (EtOAc-saturated NaHCO$_3$). The organics were dried (Na$_2$SO$_4$) and evaporated, followed by reverse phase preparative HPLC purification afforded the desired product 25 mg (62% yield for 2 steps) as a white solid. ESIMS m/z=737.10 [M+H]$^+$.

Biological Activity
1. HCV Replicon Cell Lines

HCV replicon cell lines (kindly provided by R. Bartenschlager) isolated from colonies as described by Lohman et. al. (Lohman et al. (1999) Science 285: 110-113, expressly incorporated by reference in its entirety) and used for all experiments. The HCV replicon has the nucleic acid sequence set forth in EMBL Accession No.: AJ242651, the coding sequence of which is from nucleotides 1801 to 8406.

The coding sequence of the published HCV replicon was synthesized and subsequently assembled in a modified plasmid pBR322 (Promega, Madison, Wis.) using standard molecular biology techniques. One replicon cell line ("SGR 11-7") stably expresses HCV replicon RNA which consists of (i) the HCV 5'UTR fused to the first 12 amino acids of the capsid protein, (ii) the neomycin phosphotransferase gene (neo), (iii) the IRES from encephalomyocarditis virus (EMCV), and (iv) HCV NS2 to NS5B genes and the HCV 3'UTR. Another replicon cell line ("Huh-luc/neo-ET") described by Vrolijk et. al. (Vrolijk et. al. (2003) Journal of Virological Methods 110:201-209, expressly incorporated by reference in its entirety) stably expresses HCV replicon RNA which consists of (i) the HCV 5'UTR fused to the first 12 amino acids of the capsid protein, (ii) the firefly luciferase reporter gene, (iii) the ubiquitin gene, (iv) the neomycin phosphotransferase gene (neo), (v) the IRES from encephalomyocarditis virus (EMCV), and (vi) HCV NS3 to NS5B genes that harbor cell culture adaptive mutations (E1202G, T1280I, K1846T) and the HCV 3'UTR.

These cell lines were maintained at 37° C., 5% CO$_2$, 100% relative humidity in DMEM (Cat#11965-084, Invitrogen), with 10% fetal calf serum ("FCS", Invitrogen), 1% non-essential amino acids (Invitrogen), 1% of Glutamax (Invitrogen), 1% of 100× penicillin/streptomycin (Cat#15140-122, Invitrogen) and Geneticin (Cat#10131-027, Invitrogen) at 0.75 mg/ml or 0.5 mg/ml for 11-7 and Huh-luc/neo-ET cells, respectively.

2. HCV Replicon Assay—qRT-PCR

EC$_{50}$ values of single agent compounds and combinations were determined by HCV RNA detection using quantitative RT-PCR, according to the manufacturer's instructions, with a TAQMAN® One-Step RT-PCR Master Mix Reagents Kit (Cat# AB 4309169, Applied Biosystems) on an ABI Model 7500 thermocycler. The TaqMan primers used for detecting and quantifying HCV RNA were obtained from Integrated DNA Technologies. HCV RNA was normalized to GAPDH RNA levels in drug-treated cells, which is detected and quantified using the Human GAPDH Endogenous Control Mix (Applied Biosystems, AB 4310884E). Total cellular RNA is purified from 96-well plates using the RNAqueous 96 kit (Ambion, Cat# AM1812). Chemical agent cytotoxicity is evaluated using an MTS assay according to the manufacturer's directions (Promega).

3. HCV Replicon Assay—Luciferase

Since clinical drug resistance often develops in viral infections following single agent therapies, there is a need to assess the additive, antagonistic, or synergistic properties of combination therapies. We used the HCV replicon system to assess the potential use of the compound of the present invention or in combination therapies with Interferon alpha, cyclosporine analogs and inhibitors targeting other HCV proteins. The acute effects of a single or combinations of drugs are studied in the "Huh-luc/neo-ET" replicon with each chemical agent titrated in an X or Y direction in a 6 point two-fold dilution curve centered around the EC50 of each drug. Briefly, replicon cells are seeded at 7,000 cells per well in 90 ul DMEM (without phenol red, Invitrogen Cat.#31053-036) per well with 10% FCS, 1% non-essential amino acids, 1% of Glutamax and 1% of 100× penicillin/streptomycin and incubated overnight at 37° C., 5% CO$_2$, 100% relative humidity. 16-20 h after seeding cells, test compounds previously solubilized and titrated in dimethyl sulfoxide ("DMSO") from each X plate and Y plate are diluted 1:100 in DMEM (without phenol red, Invitrogen Cat.#31053-036) with 10% FCS, 1% non-essential amino acids, 1% of Glutamax and 1% of 100× penicillin/streptomycin and added directly to the 96-well plate containing cells and growth medium at a 1:10 dilution for a final dilution of compound and DMSO of 1:1000 (0.2% DMSO final concentration). Drug treated cells are incubated at 37° C., 5% CO$_2$, 100% relative humidity for 72 hours before performing a luciferase assay using 100 ul per well BriteLite Plus (Perkin Elmer) according to the manufacturer's instructions. Data analysis utilizes the method published by Prichard and Shipman (Antiviral Research, 1990. 14:181-205). Using this method, the combination data are analyzed for antagonistic, additive, or synergistic combination effects across the entire combination surface created by the diluted compounds in combination.

The compounds of the present invention may inhibit HCV by mechanisms in addition to or other than NS5A inhibition. In one embodiment, the compounds of the present invention inhibit HCV replicon and in another embodiment the compounds of the present invention inhibit NS5A.

The compounds of the present invention can be effective against the HCV 1b genotype. It should also be understood that the compounds of the present invention can inhibit multiple genotypes of HCV. In one embodiment compound of the present invention are active against the 1a, 1b, 2a, 2b, 3a, 4a, and 5a genotypes. Table 14 shows the EC$_{50}$ values of representative compounds of the present invention against the HCV 1b genotype from the above described qRT-PCR or luciferase assay. EC$_{50}$ ranges against HCV 1b are as follows: A>10 nM; B 1-10 nM; C<1 nM.

TABLE 14

| Genotype-1b replicon EC$_{50}$ | | | | | |
|---|---|---|---|---|---|
| Example | Range | Example | Range | Example | Range |
| 368 | C | 369 | C | 370 | C |
| 371 | C | 372 | C | 373 | C |
| 374 | C | 375 | C | 376 | C |

While this invention has been particularly shown and described with references to preferred embodiments thereof, it will be understood by those skilled in the art that various changes in form and details may be made therein without departing from the scope of the invention encompassed by the appended claims.

What is claimed is:
1. A compound represented by Formula (I):

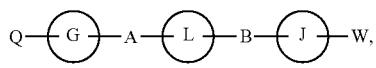

(I)

or a pharmaceutically acceptable salt thereof, wherein:
A and B are absent;
Ring L is a monocyclic or polycyclic group independently selected from the group consisting of aryl and heteroaryl, each optionally substituted;

Ring G and ring J are each independently selected from

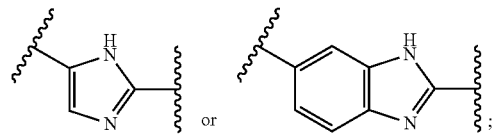 [SMILES: *c1cnc(*)[nH]1 ; *c1ccc2nc(*)[nH]c2c1]

wherein the 6-membered ring of said benzimidaolyl group is attached to ring L; wherein the said imidazolyl or benzimidazolyl groups are each optionally substituted;
W is selected from

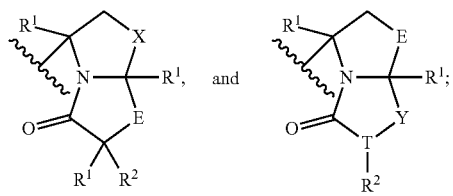

R$^1$ at each occurrence is independently hydrogen or optionally substituted C$_1$-C$_4$ alkyl;
R$^2$ at each occurrence is independently hydrogen, optionally substituted C$_1$-C$_8$ alkyl, or —NR$^a$R$^b$;
R$^a$ at each occurrence is independently hydrogen or optionally substituted C$_1$-C$_8$ alkyl;
R$^b$ at each occurrence is independently —C(O)—R$^{13}$, —C(O)—OR$^{13}$, —S(O)$_2$—R$^{13}$, —C(O)N(R$^{13}$)$_2$, or —S(O)$_2$N(R$^{13}$)$_2$;
R$^{13}$ at each occurrence is independently selected from the group consisting of C$_1$-C$_8$ alkyl, C$_2$-C$_8$ alkenyl, C$_2$-C$_8$ alkynyl, C$_3$-C$_8$ cycloalkyl, C$_3$-C$_8$ cycloalkenyl, heterocyclic, aryl, and heteroaryl, each optionally substituted;
E at each occurrence is independently O, S, OC(R$^1$)$_2$, SC(R$^1$)$_2$, OC(R$^1$)$_2$C(R$^1$)$_2$, or SC(R$^1$)$_2$C(R$^1$)$_2$;
X at each occurrence is independently absent, CH$_2$ or CH$_2$CH$_2$;
Y at each occurrence is independently absent or C(R$^1$)$_2$, C(R$^1$)$_2$C(R$^7$)$_2$, C(R$^1$)$_2$C(R$^7$)$_2$C(R$^7$)$_2$, C(R$^1$)$_2$OC(R$^1$)$_2$, or C(R$^1$)$_2$SC(R$^1$)$_2$;
R$^7$ at each occurrence is independently selected from the group consisting of hydrogen, halogen, cyano, hydroxy, O(C$_1$-C$_4$ alkyl), S(C$_1$-C$_4$ alkyl), amino optionally substituted with one or two C$_1$-C$_4$ alkyl, optionally substituted aryl, optionally substituted heteroaryl, and optionally substituted C$_1$-C$_4$ alkyl;
T at each occurrence is independently CH or C(C$_1$-C$_4$ alkyl); or alternatively, when Y is present, T-Y can be taken together to form C=CR$^1$, C=CR$^1$—CH$_2$, or C=CR$^1$—CH$_2$CH$_2$;
Q is selected from:

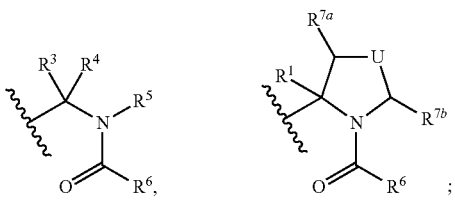

U is absent or selected from the group consisting of O, S, S(O), SO$_2$, NC(O)—(C$_1$-C$_4$ alkyl), C(O), protected carbonyl, OCH$_2$, OCH$_2$CH$_2$, SCH$_2$, SCH$_2$CH$_2$, C(R$^7$)$_2$, and C(R$^7$)$_2$C(R$^7$)$_2$;

235

R³ and R⁴ are each independently selected from the group consisting of hydrogen, optionally substituted $C_1$-$C_8$ alkyl, optionally substituted $C_2$-$C_8$ alkenyl, and optionally substituted $C_3$-$C_8$ cycloalkyl;

R⁵ is hydrogen, optionally substituted $C_1$-$C_8$ alkyl, or optionally substituted $C_3$-$C_8$ cycloalkyl;

R⁶ selected from the group consisting of optionally substituted $O(C_1$-$C_8$ alkyl), optionally substituted amino, —NR¹¹NR$^a$R$^b$ or R¹²;

R¹¹ is selected from the group consisting of hydrogen, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, heterocyclic, aryl, and heteroaryl, each optionally substituted;

R¹² at each occurrence is independently selected from the group consisting of hydrogen, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, heterocyclic, aryl, and heteroaryl, each optionally substituted; and R$^{7a}$ and R$^{7b}$ at each occurrence are each independently selected from the group consisting of hydrogen, optionally substituted aryl, and optionally substituted $C_1$-$C_4$ alkyl; or alternatively, CHR$^{7a}$—U or CHR$^{7b}$—U can be taken together to form a group selected from CH═CH, optionally substituted $C_3$-$C_8$ cycloalkyl, optionally substituted aryl, or optionally substituted heterocyclic.

2. A compound represented by Formula (I):

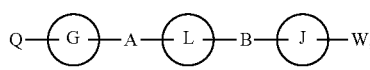

(I)

wherein A and B are absent;

Ring L is a monocyclic or polycyclic group independently selected from the group consisting of aryl and heteroaryl, each optionally substituted;

W is

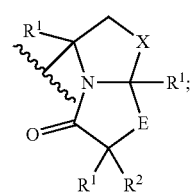

R¹ at each occurrence is independently hydrogen or optionally substituted $C_1$-$C_4$ alkyl;

R² at each occurrence is independently hydrogen, optionally substituted $C_1$-$C_8$ alkyl, or —NR$^a$R$^b$;

R$^a$ at each occurrence is independently hydrogen or optionally substituted $C_1$-$C_8$ alkyl;

R$^b$ at each occurrence is independently —C(O)—R¹³, —C(O)—OR¹³, —S(O)₂—R¹³, —C(O)N(R¹³)₂, or —S(O)₂N(R¹³)₂;

R¹³ at each occurrence is independently selected from the group consisting of $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, heterocyclic, aryl, and heteroaryl, each optionally substituted;

E at each occurrence is independently O, S, OC(R¹)₂, SC(R¹)₂, OC(R¹)₂C(R¹)₂, or SC(R¹)₂C(R¹)₂;

X at each occurrence is independently absent, CH₂ or CH₂CH₂;

236

Y at each occurrence is independently absent or C(R¹)₂, C(R¹)₂C(R⁷)₂C(R⁷)₂, C(R¹)₂OC(R¹)₂, or C(R¹)₂SC(R¹)₂;

R⁷ at each occurrence is independently selected from the group consisting of hydrogen, halogen, cyano, hydroxy, O($C_1$-$C_4$ alkyl), S($C_1$-$C_4$ alkyl), amino optionally substituted with one or two $C_1$-$C_4$ alkyl, optionally substituted aryl, optionally substituted heteroaryl, and optionally substituted $C_1$-$C_4$ alkyl;

T at each occurrence is independently CH or C($C_1$-$C_4$ alkyl); or alternatively, when Y is present, T-Y can be taken together to form C═CR¹, C═CR¹—CH₂, or C═CR¹—CH₂CH₂;

Q is selected from:

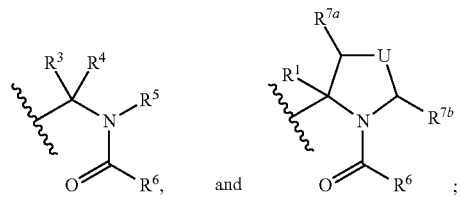

U is absent or selected from the group consisting of O, S, S(O), SO₂, NC(O)—($C_1$-$C_4$ alkyl), C(O), protected carbonyl, OCH₂, OCH₂CH₂, SCH₂, SCH₂CH₂, C(R⁷)₂, and C(R⁷)₂C(R⁷)₂;

R³ and R⁴ are each independently selected from the group consisting of hydrogen, optionally substituted $C_1$-$C_8$ alkyl, optionally substituted $C_2$-$C_8$ alkenyl, and optionally substituted $C_3$-$C_8$ cycloalkyl;

R⁵ is hydrogen, optionally substituted $C_1$-$C_8$ alkyl, or optionally substituted $C_3$-$C_8$ cycloalkyl;

R⁶ selected from the group consisting of optionally substituted $O(C_1$-$C_8$ alkyl), optionally substituted amino, —NR¹¹NR$^a$R$^b$ or R¹²;

R¹¹ is selected from the group consisting of hydrogen, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, heterocyclic, aryl, and heteroaryl, each optionally substituted;

R¹² at each occurrence is independently selected from the group consisting of hydrogen, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, heterocyclic, aryl, and heteroaryl, each optionally substituted; and R$^{7a}$ and R$^{7b}$ at each occurrence are each independently selected from the group consisting of hydrogen, optionally substituted aryl, and optionally substituted $C_1$-$C_4$ alkyl;

ring G and ring J are each independently selected from

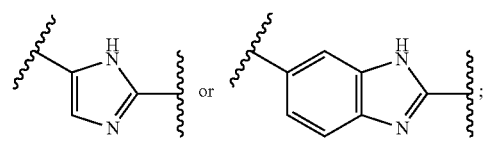 [SMILES: *c1cnc(*)[nH]1 ; *c1ccc2nc(*)[nH]c2c1]

wherein the 6-membered ring of said benzimidaolyl group is attached ring L; wherein the said imidazolyl or benzimidazolyl groups are each optionally substituted; or a pharmaceutically acceptable salt thereof.

3. The compound of claim 2, wherein Q is

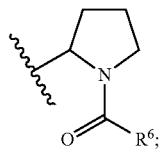

or a pharmaceutically acceptable salt thereof.

4. The compound of claim 3, wherein $R^6$ is $C_1$-$C_8$ alkyl optionally substituted with amino, hydroxy, protected amino, or O($C_1$-$C_4$ alkyl); and L is optionally substituted aryl or heteroaryl; or a pharmaceutically acceptable salt thereof.

5. The compound of claim 4, wherein L is optionally substituted bicyclic aryl or optionally substituted bicyclic heteroaryl; or a pharmaceutically acceptable salt thereof.

6. A compound selected from the group of compounds compiled in the following tables:

-continued
Compounds 1-219
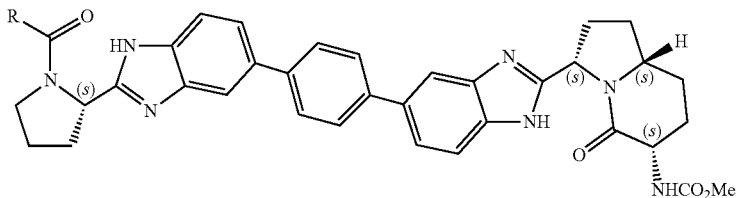
| Entry | |
|---|---|
| 8 | 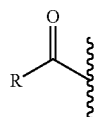 |
| 9 | 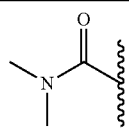 |
| 10 | 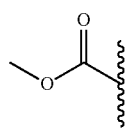 |
| 11 | 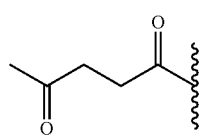 |
| 12 | 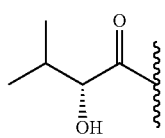 [SMILES: *C(=O)[C@H](O)CC] |
| 13 | 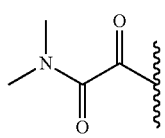 [SMILES: *C(=O)C(=O)N(C)C] |
| 14 | 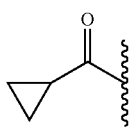 |
| 15 | 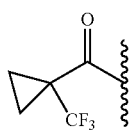 |
| 16 | 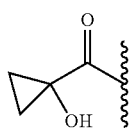 |

-continued
Compounds 1-219
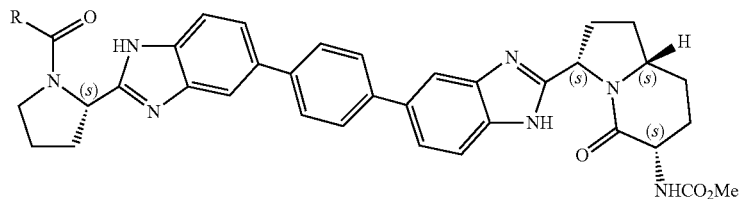
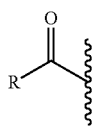
| Entry | |
|---|---|
| 17 | 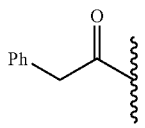 [SMILES: *C(=O)Cc1ccccc1] |
| 18 | 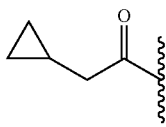 [SMILES: *C(=O)CC1CC1] |
| 19 | 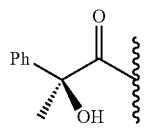 |
| 20 | 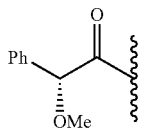 |
| 21 | 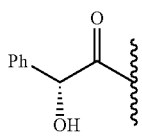 |
| 22 | 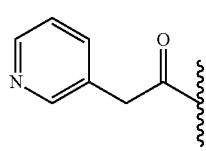 [SMILES: *C(=O)Cc1cccnc1] |
| 23 | 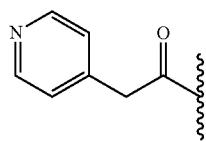 |
| 24 | 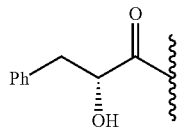 [SMILES: *C(=O)[C@H](O)Cc1ccccc1] |

-continued
Compounds 1-219
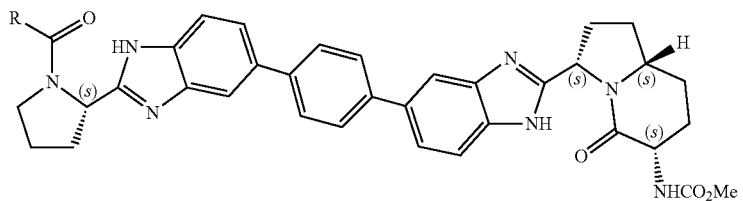
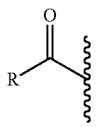
| Entry | |
|---|---|
| 25 | 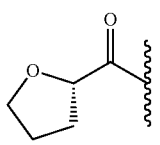 [SMILES: *C(=O)[C@@H]1CCCO1] |
| 26 | 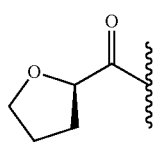 [SMILES: *C(=O)[C@H]1CCCO1] |
| 27 | 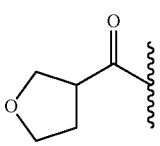 [SMILES: *C(=O)C1CCOC1] |
| 28 | 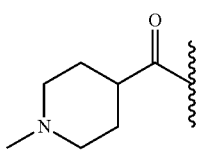 [SMILES: *C(=O)C1CCN(C)CC1] |
| 29 | 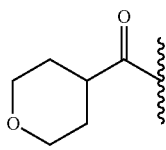 [SMILES: *C(=O)C1CCOCC1] |
| 30 | 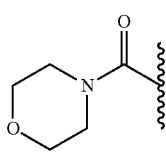 [SMILES: *C(=O)N1CCOCC1] |
| 31 | 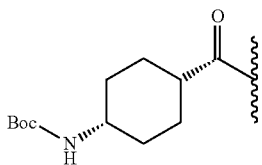 |

-continued
Compounds 1-219
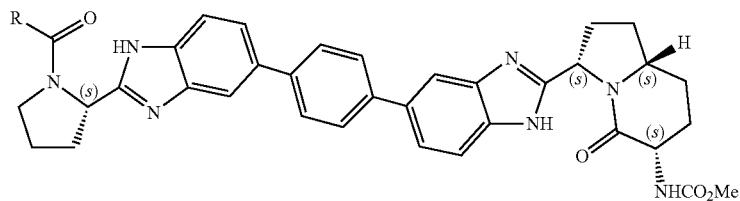
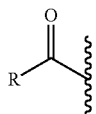
| Entry | |
|---|---|
| 32 | 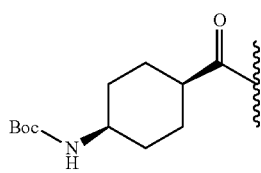 [SMILES: *C(=O)[C@H]1CC[C@@H](NC(=O)OC(C)(C)C)CC1] |
| 33 | 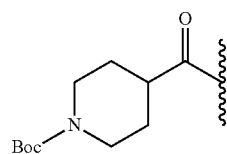 [SMILES: *C(=O)C1CCN(C(=O)OC(C)(C)C)CC1] |
| 34 | 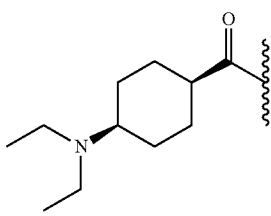 [SMILES: *C(=O)[C@H]1CC[C@@H](N(CC)CC)CC1] |
| 35 | 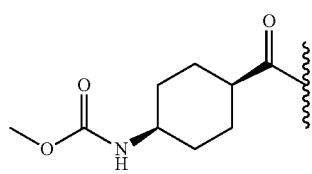 [SMILES: *C(=O)[C@H]1CC[C@@H](NC(=O)OC)CC1] |
| 36 | 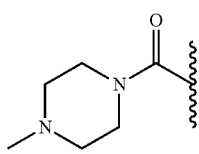 |
| 37 | 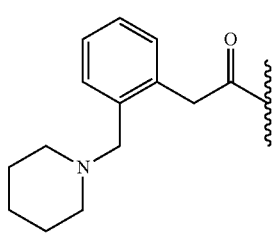 [SMILES: *C(=O)Cc1ccccc1CN1CCCCC1] |

-continued
Compounds 1-219
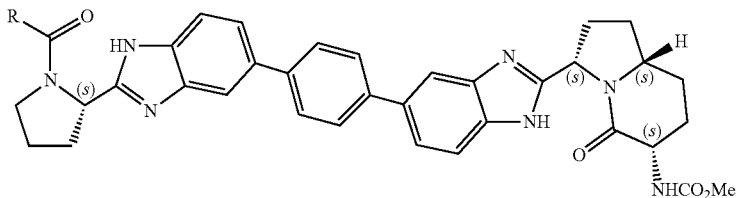
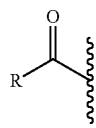
| Entry | |
|---|---|
| 38 | 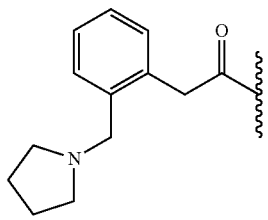 [SMILES: *C(=O)Cc1ccccc1CN1CCCC1] |
| 39 | 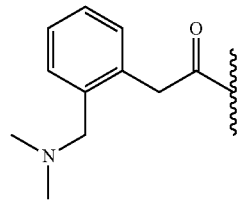 [SMILES: *C(=O)Cc1ccccc1CN(C)C] |
| 40 | 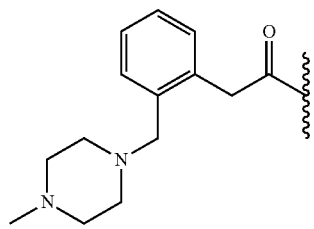 [SMILES: *C(=O)Cc1ccccc1CN1CCN(C)CC1] |
| 41 | 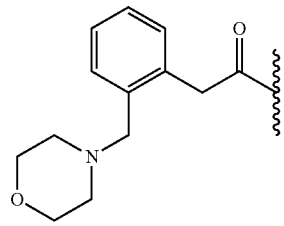 [SMILES: *C(=O)Cc1ccccc1CN1CCOCC1] |
| 42 | 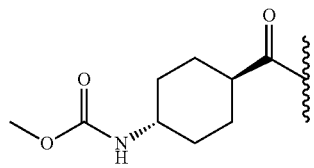 [SMILES: *C(=O)[C@H]1CC[C@H](NC(=O)OC)CC1] |
| 43 | 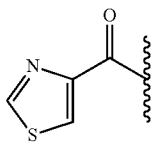 [SMILES: *C(=O)c1cscn1] |

-continued
Compounds 1-219
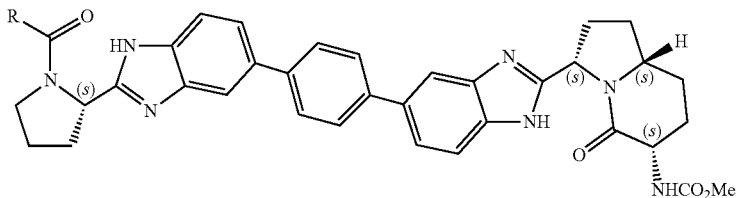
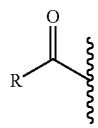
| Entry | |
|---|---|
| 44 | 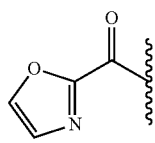 [SMILES: *C(=O)c1ncco1] |
| 45 | 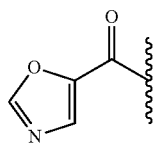 [SMILES: *C(=O)c1cnco1] |
| 46 | 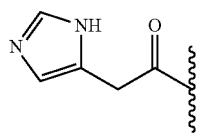 [SMILES: *C(=O)Cc1cnc[nH]1] |
| 47 | 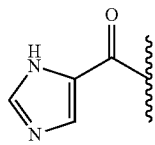 [SMILES: *C(=O)c1cnc[nH]1] |
| 48 | 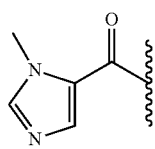 [SMILES: *C(=O)c1cncn1C] |
| 49 | 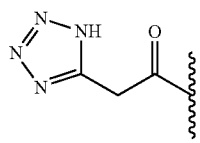 [SMILES: *C(=O)Cc1nnn[nH]1] |
| 50 | 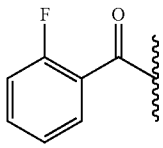 |
| 51 | 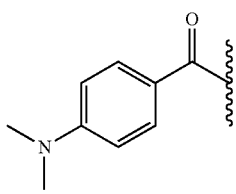 [SMILES: *C(=O)c1ccc(N(C)C)cc1] |

-continued
Compounds 1-219
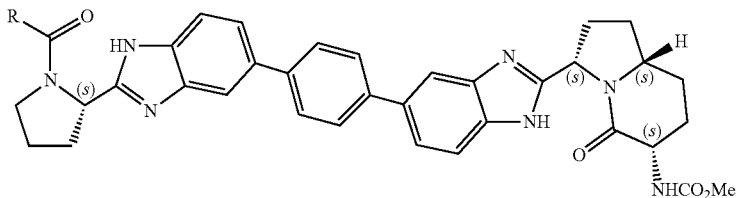
| Entry | 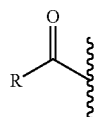 |
|---|---|
| 52 | 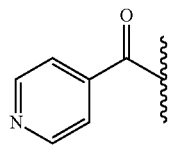 |
| 53 | 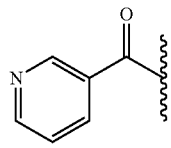 |
| 54 | 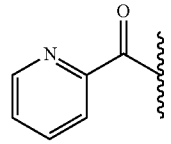 [SMILES: *C(=O)c1ccccn1] |
| 55 | 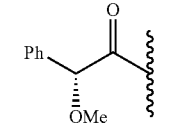 |
| 56 | 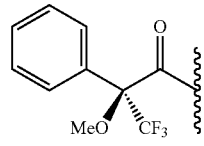 |
| 57 | 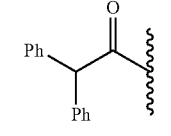 [SMILES: *C(=O)C(c1ccccc1)c1ccccc1] |
| 58 | 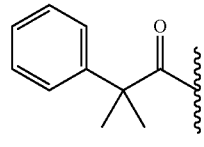 [SMILES: *C(=O)C(C)(C)c1ccccc1] |
| 59 | 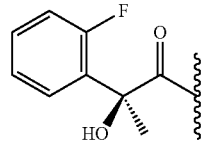 [SMILES: *C(=O)[C@@](C)(O)c1ccccc1F] |

-continued
Compounds 1-219
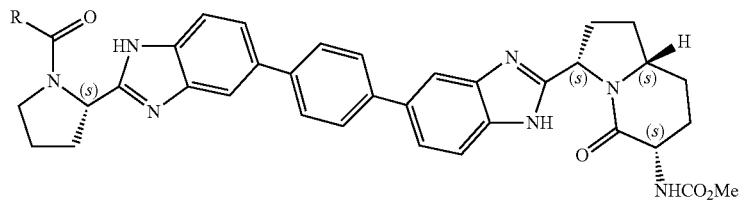
| Entry | |
|---|---|
| 60 | 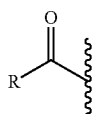 |
| 61 | 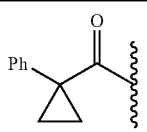 |
| 62 | 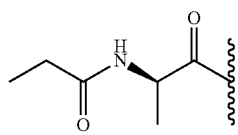 [SMILES: *C(=O)[C@@H](C)NC(=O)CC] |
| 63 | 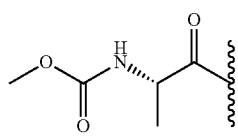 [SMILES: *C(=O)[C@H](C)NC(=O)OC] |
| 64 | 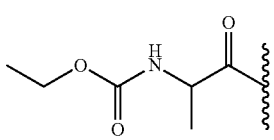 [SMILES: *C(=O)C(C)NC(=O)OCC] |
| 65 | 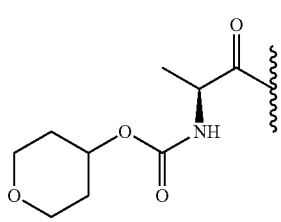 [SMILES: *C(=O)[C@H](C)NC(=O)OC1CCOCC1] |
| 66 | 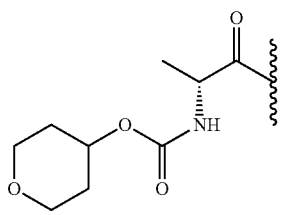 [SMILES: *C(=O)[C@@H](C)NC(=O)OC1CCOCC1] |

-continued
Compounds 1-219
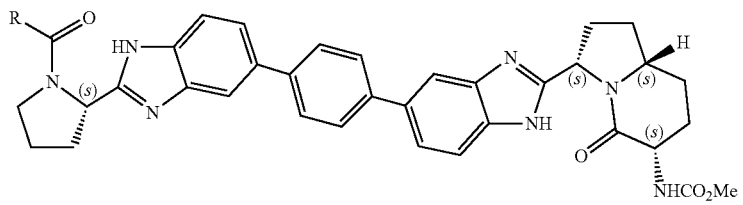
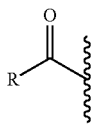
| Entry | |
|---|---|
| 67 | 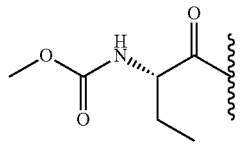 [SMILES: *C(=O)[C@H](CC)NC(=O)OC] |
| 68 | 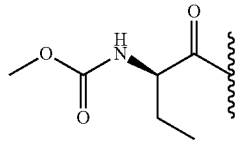 [SMILES: *C(=O)[C@@H](CC)NC(=O)OC] |
| 69 | 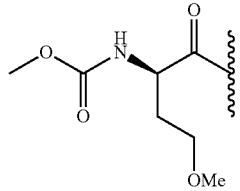 [SMILES: *C(=O)[C@@H](CCOC)NC(=O)OC] |
| 70 | 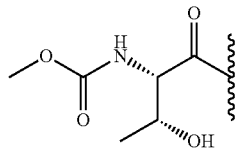 [SMILES: *C(=O)[C@@H](NC(=O)OC)[C@@H](C)O] |
| 71 | 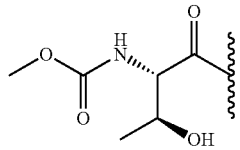 [SMILES: *C(=O)[C@@H](NC(=O)OC)[C@H](C)O] |
| 72 | 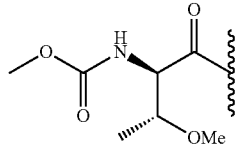 [SMILES: *C(=O)[C@H](NC(=O)OC)[C@@H](C)OC] |
| 73 | 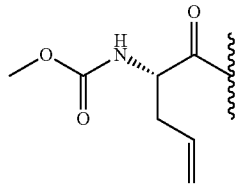 [SMILES: *C(=O)[C@H](CC=C)NC(=O)OC] |

-continued
Compounds 1-219
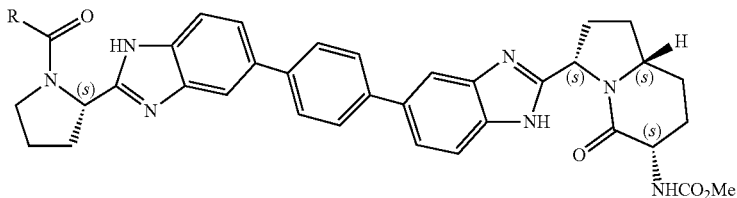
| Entry | 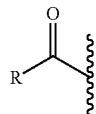 |
|---|---|
| 74 | 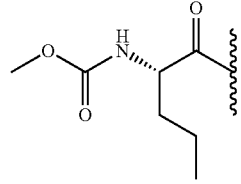 [SMILES: *C(=O)[C@H](CCC)NC(=O)OC] |
| 75 | 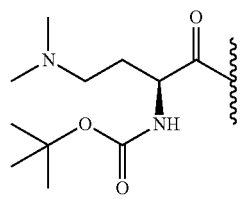 [SMILES: *C(=O)[C@H](CCN(C)C)NC(=O)OC(C)(C)C] |
| 76 | 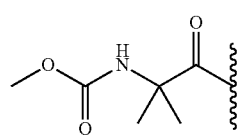 [SMILES: *C(=O)C(C)(C)NC(=O)OC] |
| 77 | 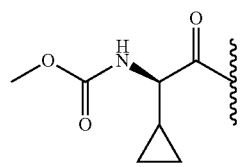 [SMILES: *C(=O)[C@H](NC(=O)OC)C1CC1] |
| 78 | 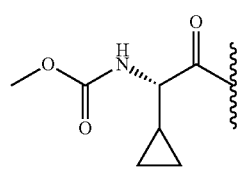 [SMILES: *C(=O)[C@@H](NC(=O)OC)C1CC1] |
| 79 | 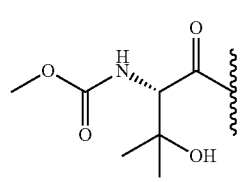 [SMILES: *C(=O)[C@@H](NC(=O)OC)C(C)(C)O] |
| 80 | 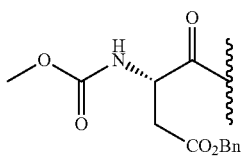 [SMILES: *C(=O)[C@H](CC(=O)OCc1ccccc1)NC(=O)OC] |

-continued
Compounds 1-219
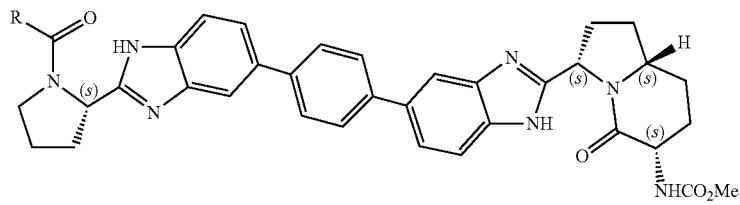
Entry
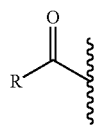
81
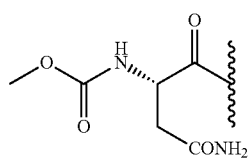 [SMILES: *C(=O)[C@H](CC(N)=O)NC(=O)OC]
82
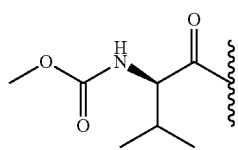 [SMILES: *C(=O)[C@H](NC(=O)OC)C(C)C]
83
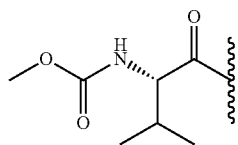 [SMILES: *C(=O)[C@@H](NC(=O)OC)C(C)C]
84
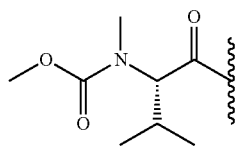 [SMILES: *C(=O)[C@H](C(C)C)N(C)C(=O)OC]
85
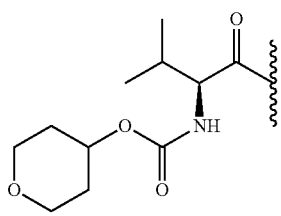 [SMILES: *C(=O)[C@@H](NC(=O)OC1CCOCC1)C(C)C]
86
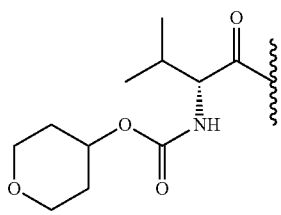 [SMILES: *C(=O)[C@H](NC(=O)OC1CCOCC1)C(C)C]

-continued
Compounds 1-219
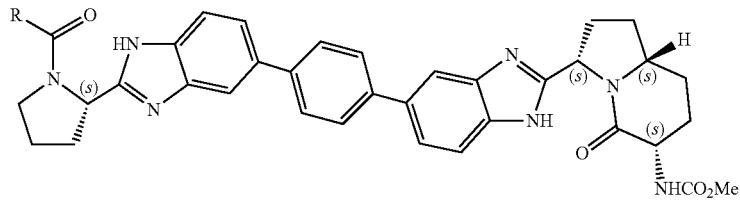
| Entry | 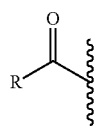 |
|---|---|
| 87 | 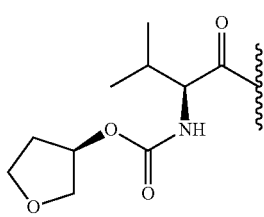 [SMILES: *C(=O)[C@@H](NC(=O)O[C@@H]1CCOC1)C(C)C] |
| 88 | 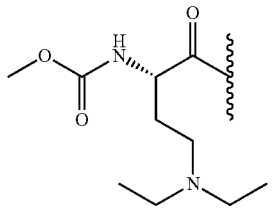 [SMILES: *C(=O)[C@H](CCN(CC)CC)NC(=O)OC] |
| 89 | 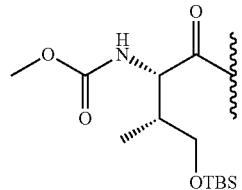 [SMILES: *C(=O)[C@@H](NC(=O)OC)[C@@H](C)CO[Si](C)(C)C(C)(C)C] |
| 90 | 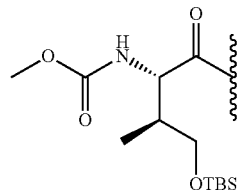 [SMILES: *C(=O)[C@@H](NC(=O)OC)[C@H](C)CO[Si](C)(C)C(C)(C)C] |
| 91 | 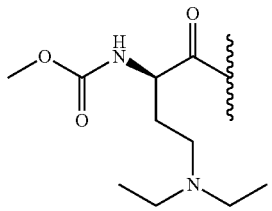 [SMILES: *C(=O)[C@@H](CCN(CC)CC)NC(=O)OC] |

-continued
Compounds 1-219
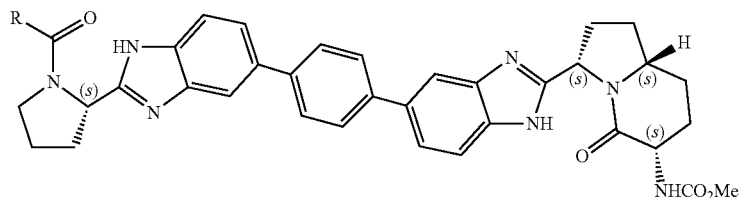
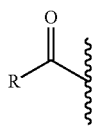
| Entry | |
|---|---|
| 92 | 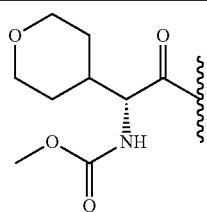 |
| 93 | 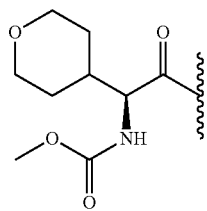 [SMILES: *C(=O)[C@@H](NC(=O)OC)C1CCOCC1] |
| 94 | 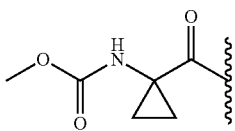 [SMILES: *C(=O)C1(NC(=O)OC)CC1] |
| 95 | 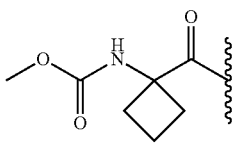 [SMILES: *C(=O)C1(NC(=O)OC)CCC1] |
| 96 | 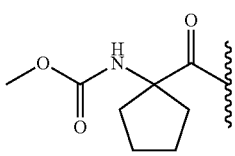 [SMILES: *C(=O)C1(NC(=O)OC)CCCC1] |
| 97 | 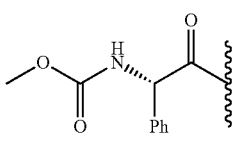 [SMILES: *C(=O)[C@@H](NC(=O)OC)c1ccccc1] |
| 98 | 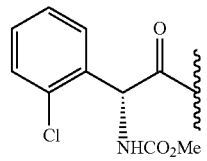 |

-continued
Compounds 1-219
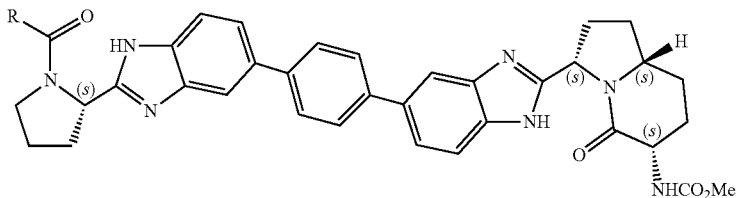
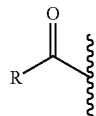
| Entry | |
|---|---|
| 99 | 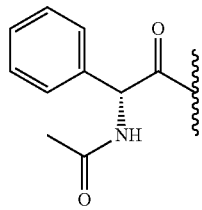 [SMILES: *C(=O)[C@H](NC(C)=O)c1ccccc1] |
| 100 | 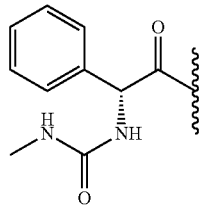 [SMILES: *C(=O)[C@H](NC(=O)NC)c1ccccc1] |
| 101 | 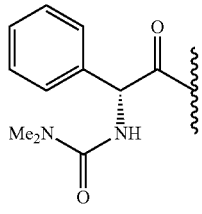 [SMILES: *C(=O)[C@H](NC(=O)N(C)C)c1ccccc1] |
| 102 | 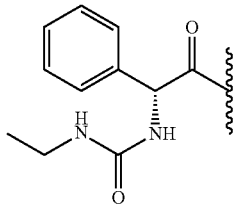 [SMILES: *C(=O)[C@H](NC(=O)NCC)c1ccccc1] |
| 103 | 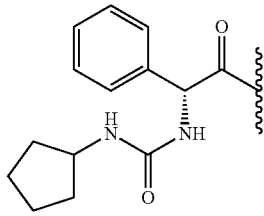 [SMILES: *C(=O)[C@H](NC(=O)NC1CCCC1)c1ccccc1] |
| 104 | 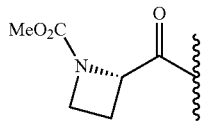 [SMILES: *C(=O)[C@@H]1CCN1C(=O)OC] |

Compounds 1-219
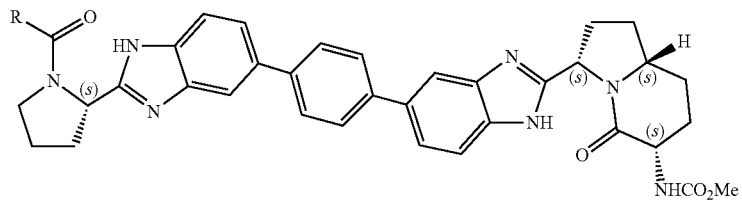
| Entry | |
|---|---|
| 105 | 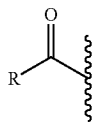 |
| 106 | 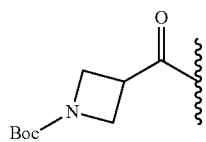 [SMILES: *C(=O)C1CN(C(=O)OC(C)(C)C)C1] |
| 107 | 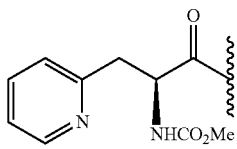 |
| 108 | 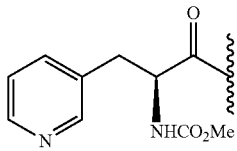 |
| 109 | 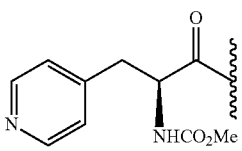 |
| 110 | 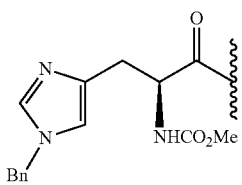 |
| 111 | 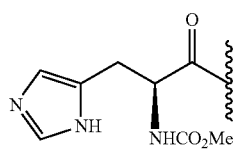 |

Compounds 1-219
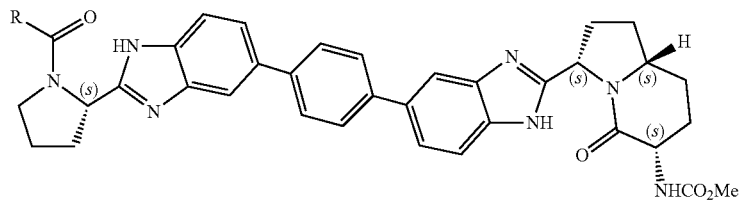
| Entry | 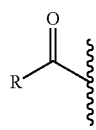 |
|---|---|
| 112 | 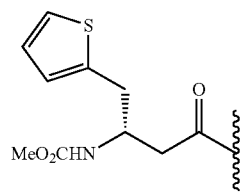 |
| 113 | 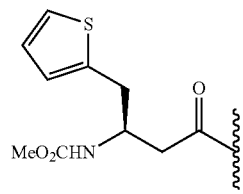 |
| 114 | 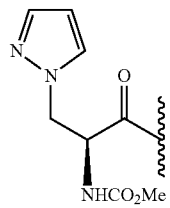 |
| 115 | 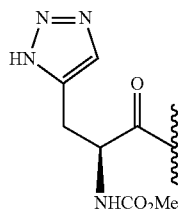 |
| 116 | 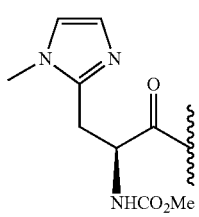 |

-continued
Compounds 1-219
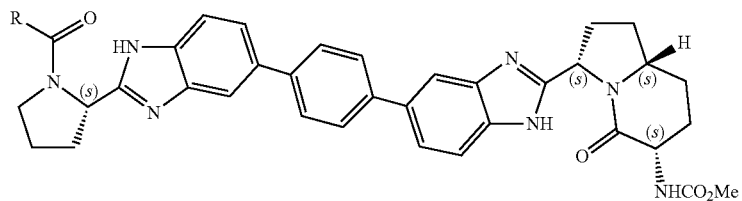
| Entry | 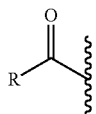 |
|---|---|
| 117 | 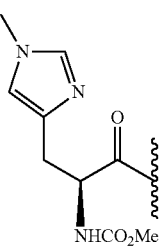 |
| 118 | 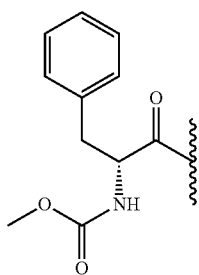 [SMILES: *C(=O)[C@@H](Cc1ccccc1)NC(=O)OC] |
| 119 | 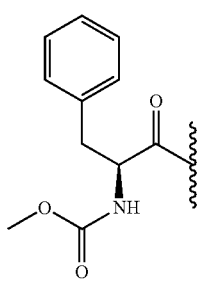 [SMILES: *C(=O)[C@H](Cc1ccccc1)NC(=O)OC] |
| 120 | 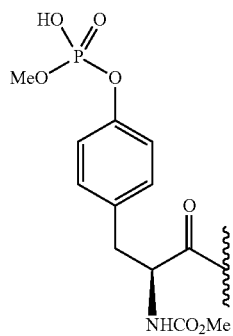 |

-continued
Compounds 1-219
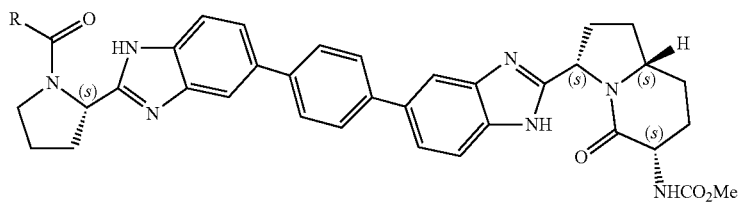
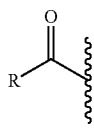
| Entry | |
|---|---|
| 121 | 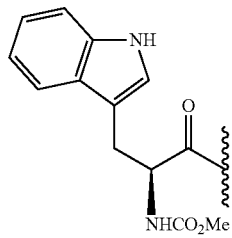 |
| 122 | 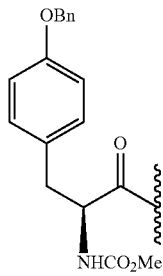 |
| 123 | 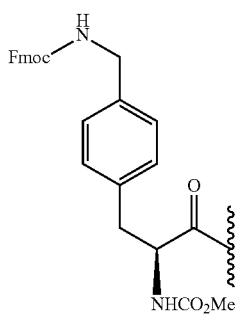 |
| 124 | 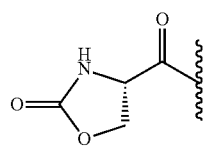 [SMILES: *C(=O)[C@@H]1COC(=O)N1] |
| 125 | 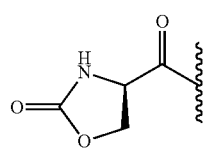 [SMILES: *C(=O)[C@H]1COC(=O)N1] |

-continued
Compounds 1-219
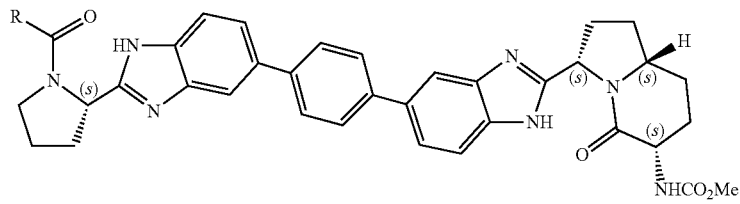
| Entry | 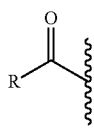 |
|---|---|
| 126 | 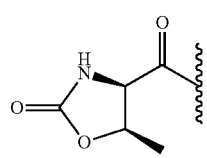 [SMILES: *C(=O)[C@@H]1NC(=O)O[C@@H]1C] |
| 127 | 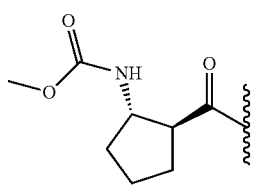 [SMILES: *C(=O)[C@H]1CCC[C@@H]1NC(=O)OC] |
| 128 | 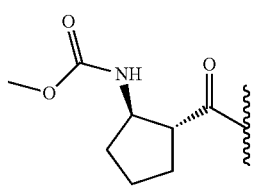 [SMILES: *C(=O)[C@@H]1CCC[C@H]1NC(=O)OC] |
| 129 | 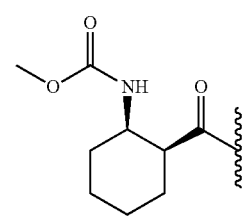 [SMILES: *C(=O)[C@H]1CCCC[C@H]1NC(=O)OC] |
| 130 | 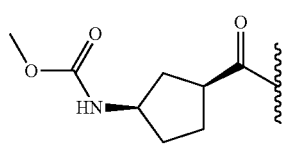 [SMILES: *C(=O)[C@H]1CC[C@@H](NC(=O)OC)C1] |
| 131 | 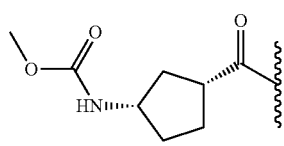 [SMILES: *C(=O)[C@@H]1CC[C@H](NC(=O)OC)C1] |

-continued
Compounds 1-219
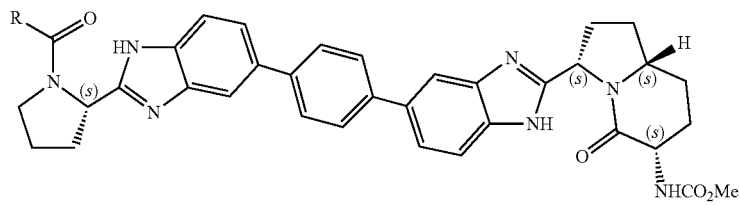
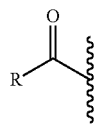
| Entry | |
|---|---|
| 132 | 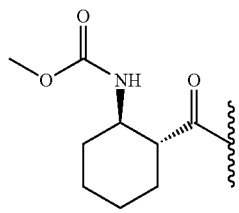 [SMILES: *C(=O)[C@@H]1CCCC[C@H]1NC(=O)OC] |
| 133 | 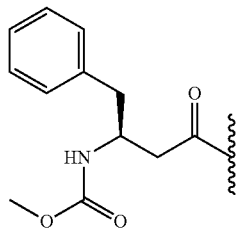 [SMILES: *C(=O)C[C@H](Cc1ccccc1)NC(=O)OC] |
| 134 | 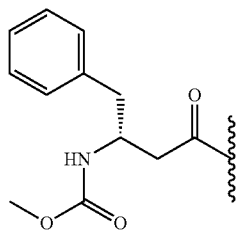 [SMILES: *C(=O)C[C@@H](Cc1ccccc1)NC(=O)OC] |
| 135 | 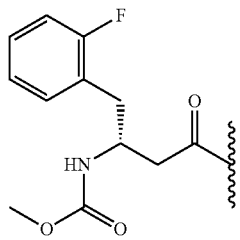 [SMILES: *C(=O)C[C@@H](Cc1ccccc1F)NC(=O)OC] |
| 136 | 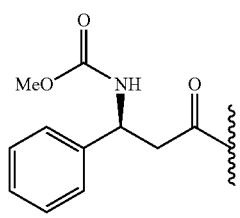 [SMILES: *C(=O)C[C@H](NC(=O)OC)c1ccccc1] |

-continued
Compounds 1-219
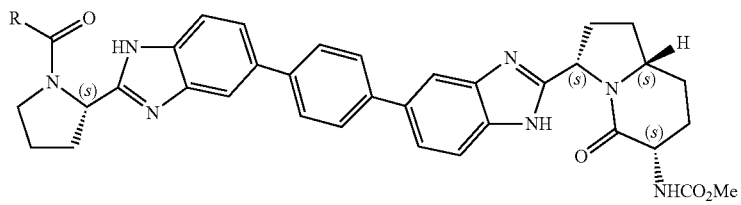
| Entry | 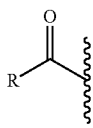 |
|---|---|
| 137 | 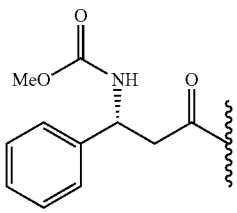 [SMILES: *C(=O)C[C@@H](NC(=O)OC)c1ccccc1] |
| 138 | 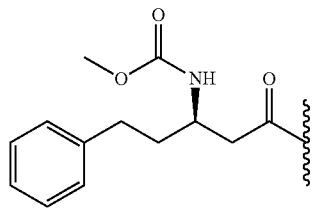 [SMILES: *C(=O)C[C@@H](CCc1ccccc1)NC(=O)OC] |
| 139 | 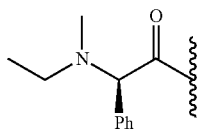 [SMILES: *C(=O)[C@@H](c1ccccc1)N(C)CC] |
| 140 | 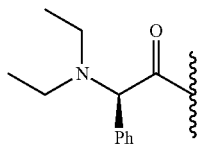 [SMILES: *C(=O)[C@@H](c1ccccc1)N(CC)CC] |
| 141 | 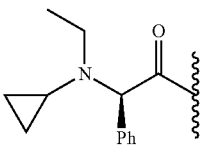 [SMILES: *C(=O)[C@@H](c1ccccc1)N(CC)C1CC1] |
| 142 | 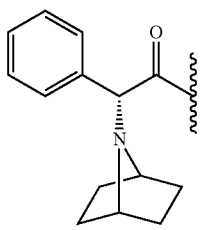 [SMILES: *C(=O)[C@@H](c1ccccc1)N1C2CCC1CC2] |

Compounds 1-219
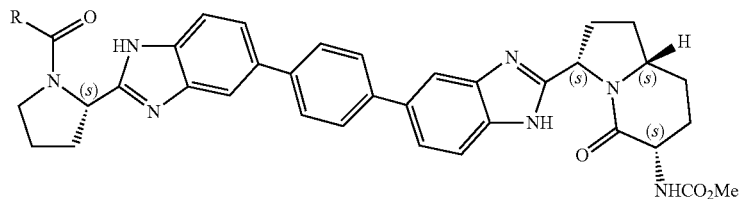
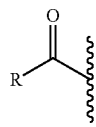
| Entry | |
|---|---|
| 143 | 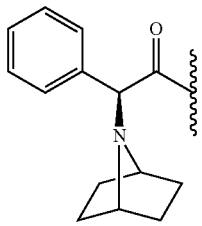 [SMILES: *C(=O)[C@H](c1ccccc1)N1C2CCC1CC2] |
| 144 | 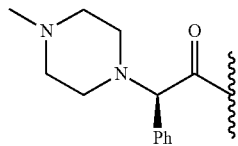 [SMILES: *C(=O)[C@@H](c1ccccc1)N1CCN(C)CC1] |
| 145 | 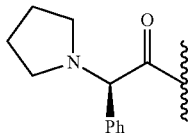 [SMILES: *C(=O)[C@@H](c1ccccc1)N1CCCC1] |
| 146 | 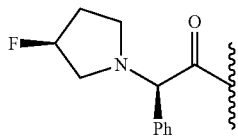 [SMILES: *C(=O)[C@@H](c1ccccc1)N1CC[C@H](F)C1] |
| 147 | 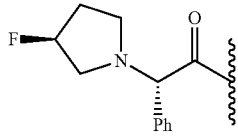 [SMILES: *C(=O)[C@H](c1ccccc1)N1CC[C@H](F)C1] |
| 148 | 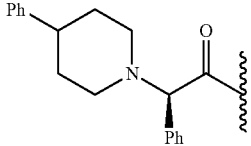 [SMILES: *C(=O)[C@@H](c1ccccc1)N1CCC(c2ccccc2)CC1] |
| 149 | 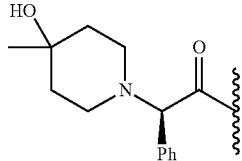 [SMILES: *C(=O)[C@@H](c1ccccc1)N1CCC(C)(O)CC1] |

-continued
Compounds 1-219
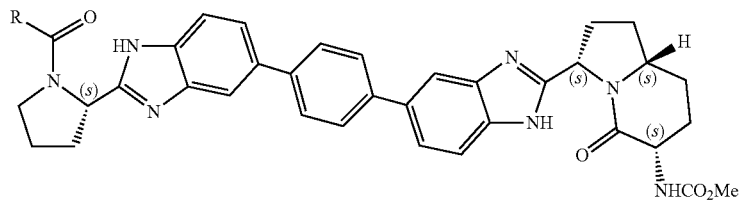
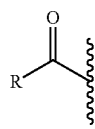
| Entry | |
|---|---|
| 150 | 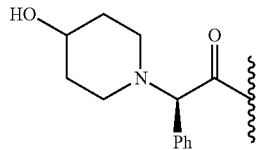 [SMILES: *C(=O)[C@@H](c1ccccc1)N1CCC(O)CC1] |
| 151 | 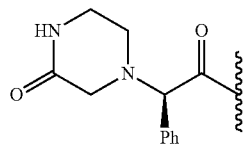 [SMILES: *C(=O)[C@@H](c1ccccc1)N1CCNC(=O)C1] |
| 152 | 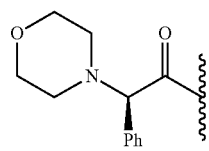 [SMILES: *C(=O)[C@@H](c1ccccc1)N1CCOCC1] |
| 153 | 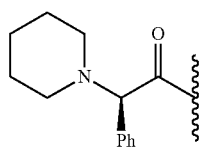 [SMILES: *C(=O)[C@@H](c1ccccc1)N1CCCCC1] |
| 154 | 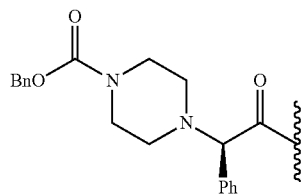 [SMILES: *C(=O)[C@@H](c1ccccc1)N1CCN(C(=O)OCc2ccccc2)CC1] |
| 155 | 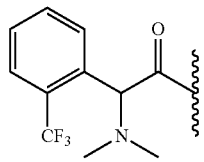 |
| 156 | 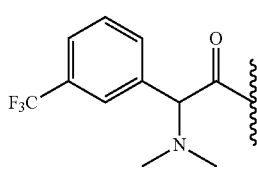 [SMILES: *C(=O)C(c1cccc(C(F)(F)F)c1)N(C)C] |

Compounds 1-219
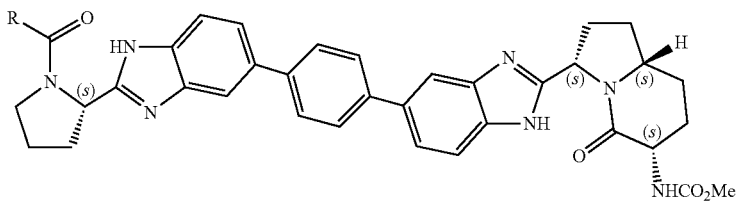
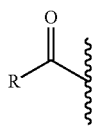
| Entry | |
|---|---|
| 157 | 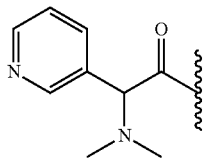 |
| 158 | 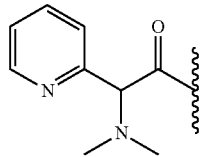 [SMILES: *C(=O)C(c1ccccn1)N(C)C] |
| 159 | 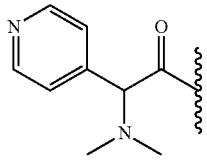 [SMILES: *C(=O)C(c1ccncc1)N(C)C] |
| 160 | 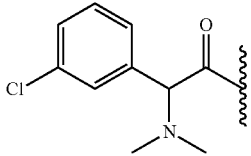 [SMILES: *C(=O)C(c1cccc(Cl)c1)N(C)C] |
| 161 | 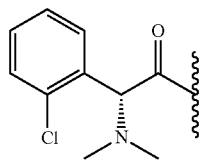 |
| 162 | 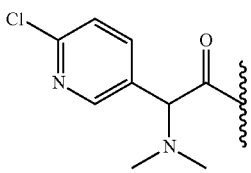 [SMILES: *C(=O)C(c1ccc(Cl)nc1)N(C)C] |
| 163 | 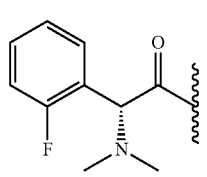 |

-continued
Compounds 1-219
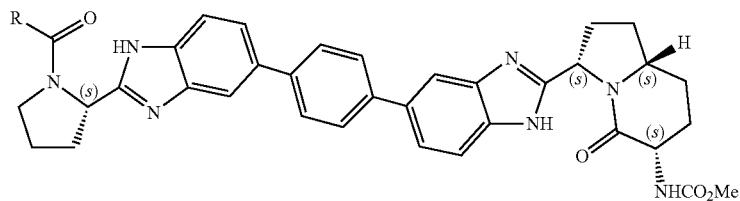
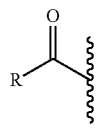
| Entry | |
|---|---|
| 164 | 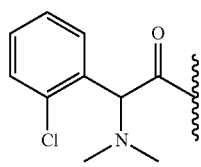 [SMILES: *C(=O)C(c1ccccc1Cl)N(C)C] |
| 165 | 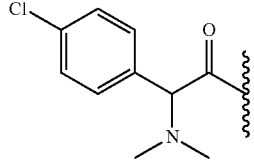 [SMILES: *C(=O)C(c1ccc(Cl)cc1)N(C)C] |
| 166 | 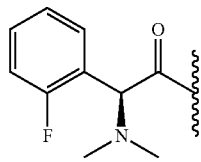 [SMILES: *C(=O)[C@H](c1ccccc1F)N(C)C] |
| 167 | 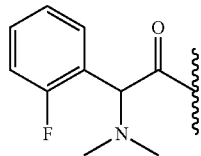 [SMILES: *C(=O)C(c1ccccc1F)N(C)C] |
| 168 | 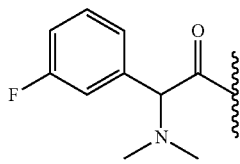 |
| 169 | 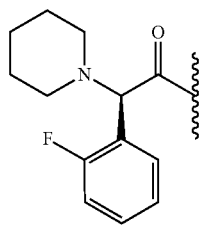 [SMILES: *C(=O)[C@@H](c1ccccc1F)N1CCCCC1] |

-continued
Compounds 1-219
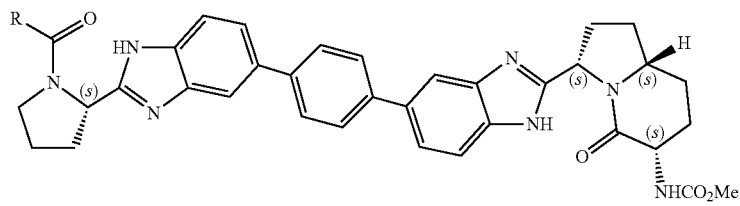
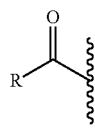
| Entry | |
|---|---|
| 170 | 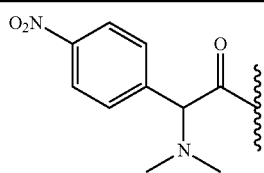 |
| 171 | 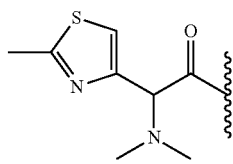 [SMILES: *C(=O)C(c1csc(C)n1)N(C)C] |
| 172 | 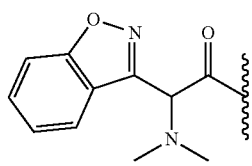 [SMILES: *C(=O)C(c1noc2ccccc12)N(C)C] |
| 173 | 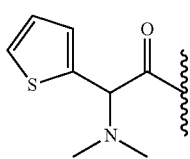 [SMILES: *C(=O)C(c1cccs1)N(C)C] |
| 174 | 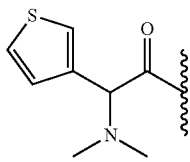 [SMILES: *C(=O)C(c1ccsc1)N(C)C] |
| 175 | 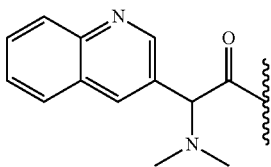 [SMILES: *C(=O)C(c1cnc2ccccc2c1)N(C)C] |
| 176 | 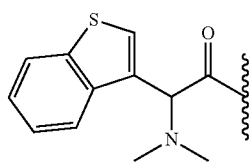 [SMILES: *C(=O)C(c1csc2ccccc12)N(C)C] |

-continued
Compounds 1-219
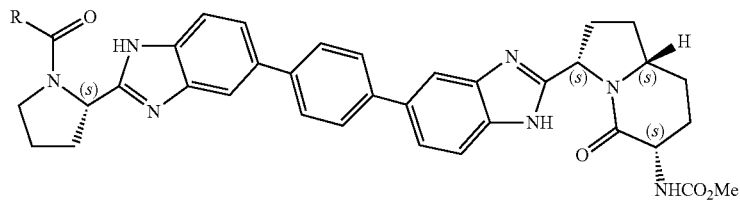
| Entry | 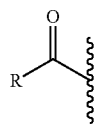 |
|---|---|
| 177 | 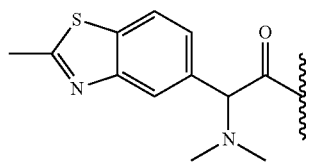 [SMILES: *C(=O)C(c1ccc2sc(C)nc2c1)N(C)C] |
| 178 | 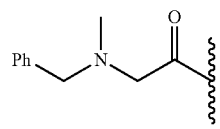 [SMILES: *C(=O)CN(C)Cc1ccccc1] |
| 179 | 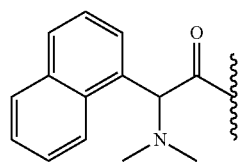 [SMILES: *C(=O)C(c1cccc2ccccc12)N(C)C] |
| 180 | 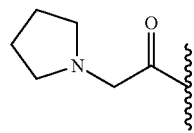 [SMILES: *C(=O)CN1CCCC1] |
| 181 | 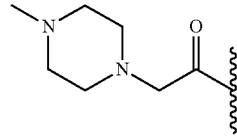 [SMILES: *C(=O)CN1CCN(C)CC1] |
| 182 | 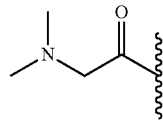 |
| 183 | 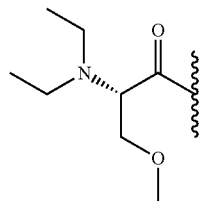 [SMILES: *C(=O)[C@H](COC)N(CC)CC] |

-continued
Compounds 1-219
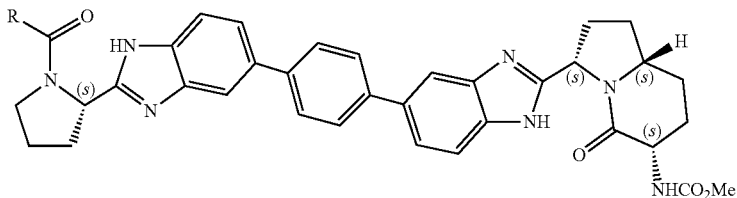
| Entry | |
|---|---|
| 184 | 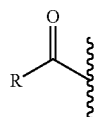 |
| 185 | 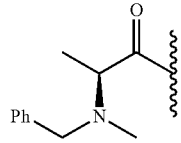 [SMILES: *C(=O)[C@H](C)N(C)Cc1ccccc1] |
| 186 | 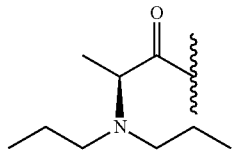 [SMILES: *C(=O)[C@H](C)N(CCC)CCC] |
| 187 | 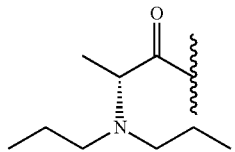 [SMILES: *C(=O)[C@@H](C)N(CCC)CCC] |
| 188 | 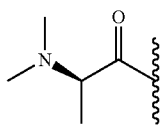 [SMILES: *C(=O)[C@@H](C)N(C)C] |
| 189 | 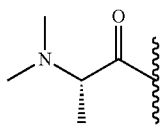 [SMILES: *C(=O)[C@H](C)N(C)C] |
| 190 | 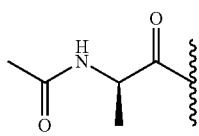 [SMILES: *C(=O)[C@@H](C)NC(C)=O] |
| 191 | 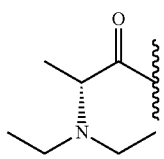 [SMILES: *C(=O)[C@@H](C)N(CC)CC] |

Compounds 1-219
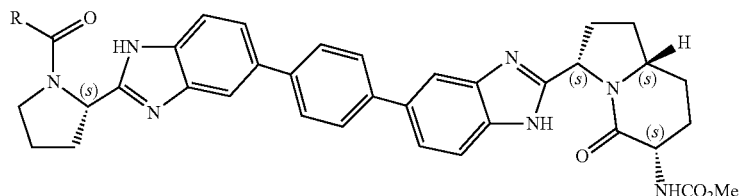
| Entry | 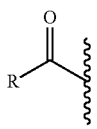 |
|---|---|
| 192 | 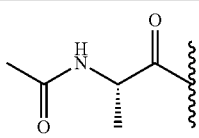 [SMILES: *C(=O)[C@H](C)NC(C)=O] |
| 193 | 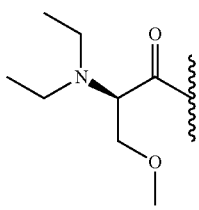 [SMILES: *C(=O)[C@@H](COC)N(CC)CC] |
| 194 | 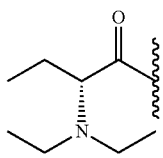 [SMILES: *C(=O)[C@@H](CC)N(CC)CC] |
| 195 | 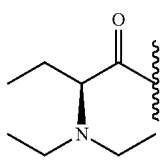 [SMILES: *C(=O)[C@H](CC)N(CC)CC] |
| 196 | 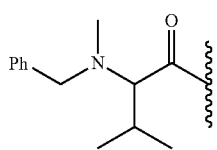 [SMILES: *C(=O)C(C(C)C)N(C)Cc1ccccc1] |
| 197 | 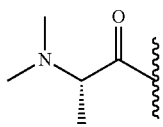 [SMILES: *C(=O)[C@H](C)N(C)C] |
| 198 | 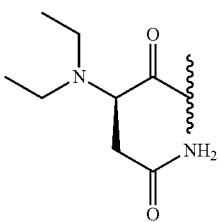 [SMILES: *C(=O)[C@@H](CC(N)=O)N(CC)CC] |

Compounds 1-219
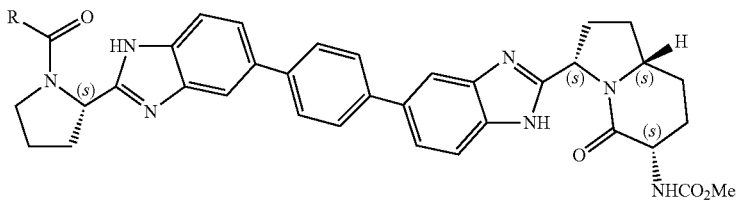
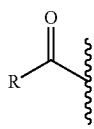
| Entry | |
|---|---|
| 199 | 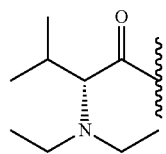 [SMILES: *C(=O)[C@@H](C(C)C)N(CC)CC] |
| 200 | 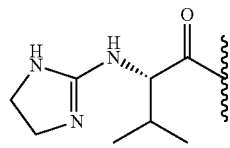 [SMILES: *C(=O)[C@@H](NC1=NCCN1)C(C)C] |
| 201 | 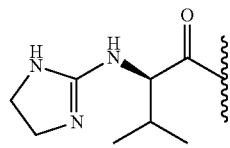 [SMILES: *C(=O)[C@H](NC1=NCCN1)C(C)C] |
| 202 | 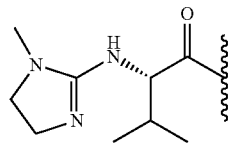 |
| 203 | 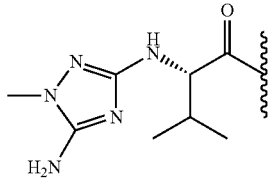 [SMILES: *C(=O)[C@@H](Nc1nc(N)n(C)n1)C(C)C] |
| 204 | 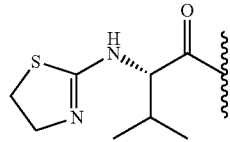 [SMILES: *C(=O)[C@@H](NC1=NCCS1)C(C)C] |
| 205 | 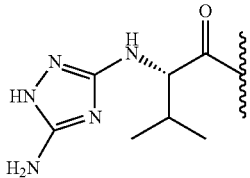 [SMILES: *C(=O)[C@@H](Nc1n[nH]c(N)n1)C(C)C] |

-continued
Compounds 1-219
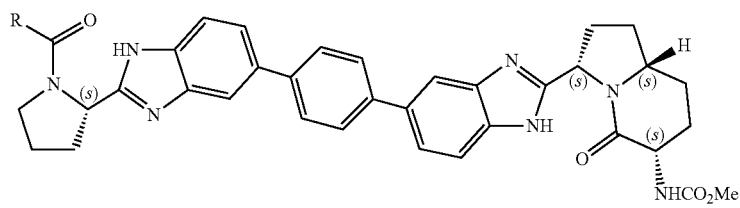
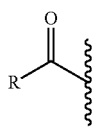
| Entry | |
|---|---|
| 206 | 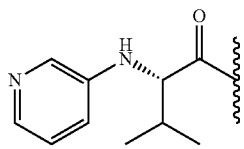 [SMILES: *C(=O)[C@@H](Nc1cccnc1)C(C)C] |
| 207 | 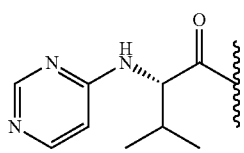 [SMILES: *C(=O)[C@@H](Nc1ccncn1)C(C)C] |
| 208 | 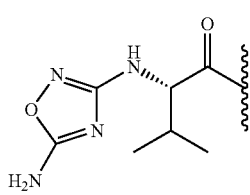 [SMILES: *C(=O)[C@@H](Nc1noc(N)n1)C(C)C] |
| 209 | 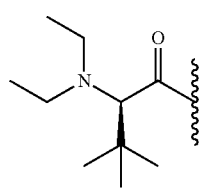 [SMILES: *C(=O)[C@H](N(CC)CC)C(C)(C)C] |
| 210 | 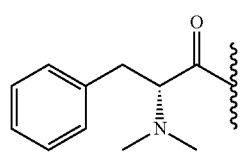 [SMILES: *C(=O)[C@@H](Cc1ccccc1)N(C)C] |
| 211 | 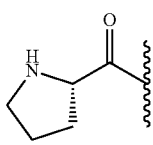 [SMILES: *C(=O)[C@@H]1CCCN1] |
| 212 | 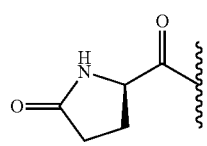 [SMILES: *C(=O)[C@H]1CCC(=O)N1] |

-continued
Compounds 1-219
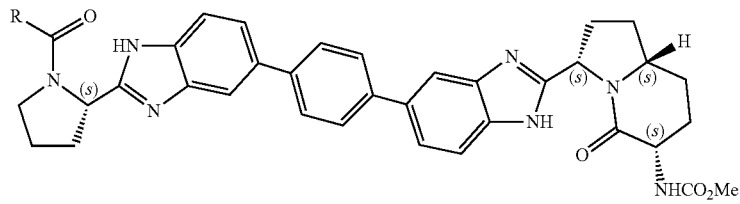
| Entry | 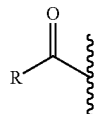 |
|---|---|
| 213 | 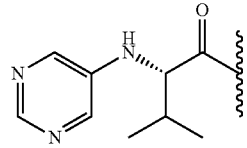 [SMILES: *C(=O)[C@@H](Nc1cncnc1)C(C)C] |
| 214 | 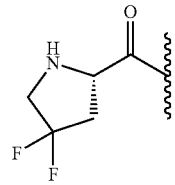 |
| 215 | 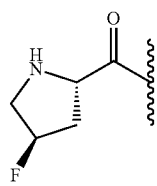 [SMILES: *C(=O)[C@@H]1C[C@@H](F)CN1] |
| 216 | 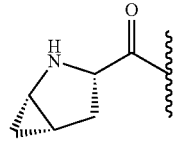 [SMILES: *C(=O)[C@@H]1C[C@@H]2C[C@@H]2N1] |
| 217 | 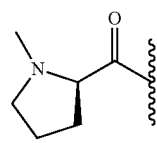 [SMILES: *C(=O)[C@H]1CCCN1C] |
| 218 | 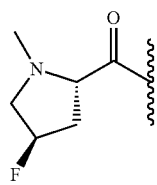 [SMILES: *C(=O)[C@@H]1C[C@@H](F)CN1C] |
| 219 | 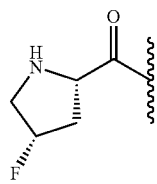 [SMILES: *C(=O)[C@@H]1C[C@H](F)CN1] |

Compounds 220-237

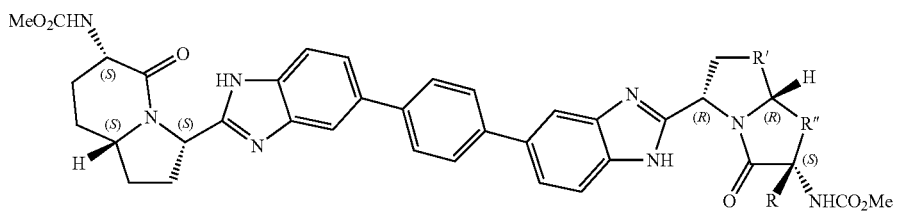

| Entry | R | R' | R" | Entry | R | R' | R" |
|---|---|---|---|---|---|---|---|
| 220 | H | CH$_2$ | CH$_2$CH$_2$ | 221 | H | CH$_2$ | CH$_2$ |
| 222 | Me | CH$_2$ | CH$_2$CH$_2$ | 223 | H | absent | CH$_2$ |
| 224 | H | O | CH$_2$CH$_2$ | 225 | H | CH$_2$ | absent |
| 226 | H | S | CH$_2$CH$_2$ | 227 | H | CH$_2$ | OCH$_2$ |
| 228 | H | O | CH$_2$OCH$_2$ | 229 | H | CH$_2$ | SCH$_2$ |
| 230 | H | S | CH$_2$CMe$_2$ | 231 | H | S | CH$_2$SCH$_2$ |
| 232 | H | CH$_2$ | CH$_2$CH$_2$CH$_2$ | 233 | H | CH$_2$ | OCH$_2$CH$_2$ |
| 234 | H | O | CH$_2$CH$_2$CH$_2$ | 235 | H | S | CH$_2$CH$_2$CH$_2$ |
| 236 | H | CH$_2$ | CH$_2$CMe$_2$ | 237 | CHMe$_2$ | O | CH$_2$CH$_2$ |

Compounds 238-247

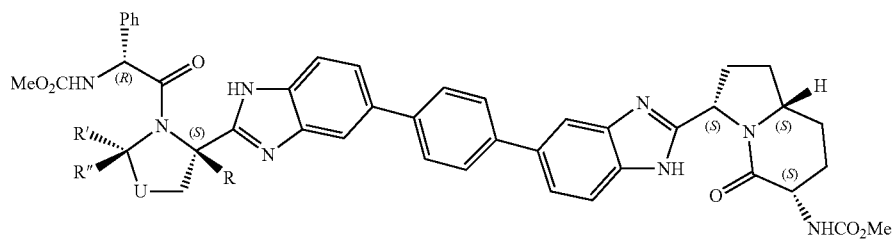

| Entry | R | R' | R" | U | Entry | R | R' | R" | U |
|---|---|---|---|---|---|---|---|---|---|
| 238 | Me | H | H | CH$_2$ | 239 | H | H | H | CF$_2$ |
| 240 | Me | H | H | S | 241 | H | H | H | ⟨CHF⟩ |
| 242 | Me | H | H | O | 243 | H | H | H | ⟨CHF⟩ |
| 244 | H | Ph | H | CH$_2$ | 245 | H | H | H | ⟨CHOH⟩ |
| 246 | H | H | Ph | CH$_2$ | 247 | H | H | H | ⟨CHOH⟩ |

| Compounds 248-251 |
|---|
| 248 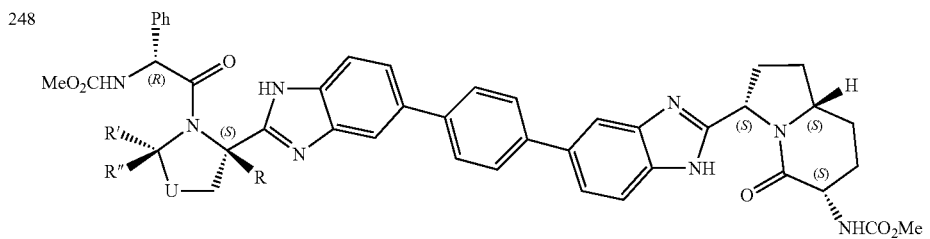 |
| 249 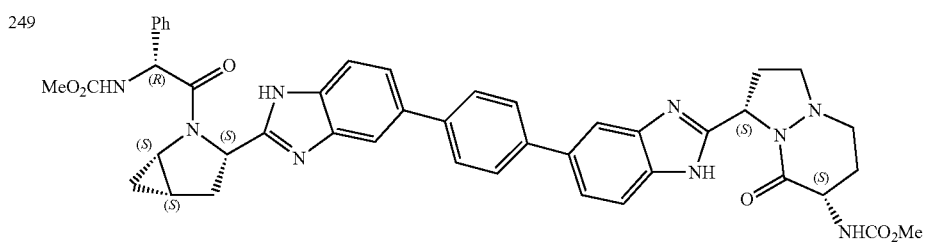 |
| 250 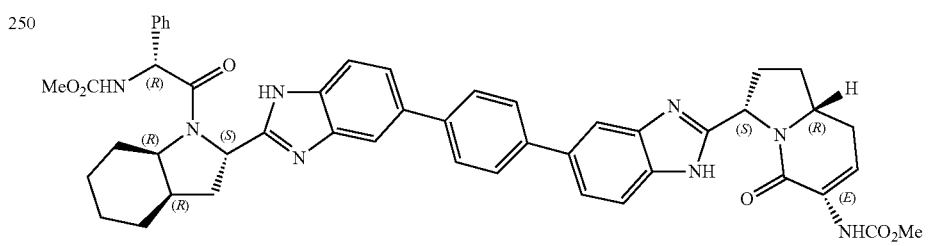 |
| 251 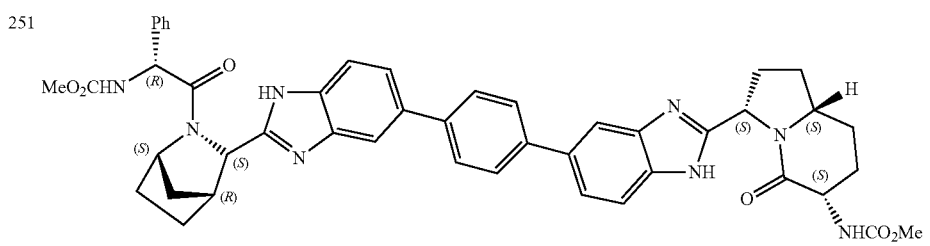 |
| Compounds 252-261 |
|---|
| 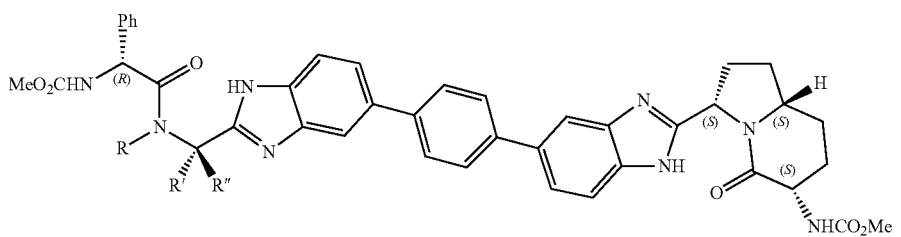 |
| Entry | R | R' | R" | Entry | R | R' | R" |
|---|---|---|---|---|---|---|---|
| 252 | Me | Me | H | 253 | H | Me | H |
| 254 | Me | H | Me | 255 | cyclopropyl | Me | H |
| 256 | Me | Me | Me | 257 | Me | cyclopropyl | H |
| 258 | Me | Allyl | H | 269 | Et | Me | H |
| 260 | Me | CHMe₂ | H | 261 | Me | Et | H |

Compounds 262-271
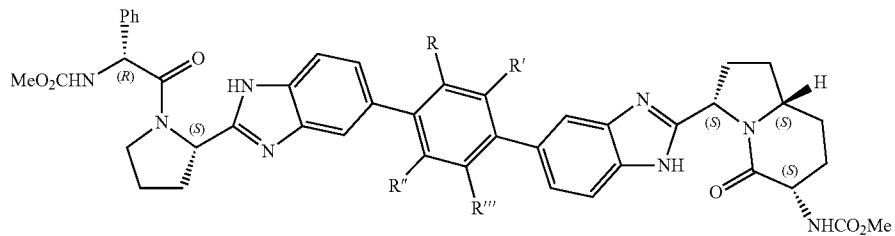
| Entry | R | R' | R" | R'" | Entry | R | R' | R" | R'" |
|---|---|---|---|---|---|---|---|---|---|
| 262 | F | H | H | H | 263 | F | F | H | H |
| 264 | Me | H | H | H | 265 | Me | Me | H | H |
| 266 | H | H | Me | Me | 267 | H | H | Et | Et |
| 278 | CF$_3$ | H | H | H | 269 | CF$_3$ | H | CF$_3$ | H |
| 270 | Cl | H | H | H | 271 | Cl | H | Cl | H |
Compounds 272-289
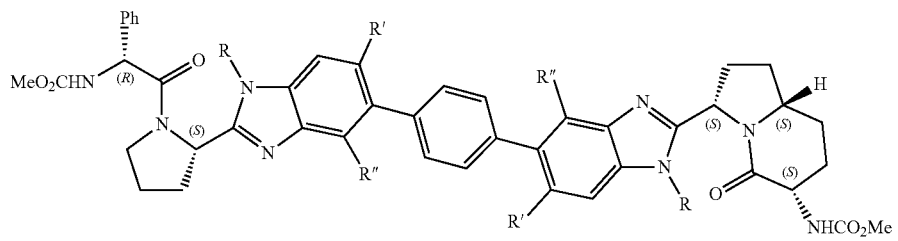
| Entry | R | R' | R" | Entry | R | R' | R" |
|---|---|---|---|---|---|---|---|
| 272 | Me | H | H | 273 | H | CO$_2$H | H |
| 274 | H | F | H | 275 | H | H | CO$_2$H |
| 276 | H | H | F | 277 | H | CO$_2$Me | H |
| 278 | H | Cl | H | 279 | H | H | CO$_2$Me |
| 280 | H | H | Cl | 281 | H | CONH$_2$ | H |
| 282 | H | Me | H | 283 | H | H | CONH$_2$ |
| 284 | H | H | Me | 285 | H | OMe | H |
| 286 | H | CF$_3$ | H | 287 | H | H | OMe |
| 288 | H | H | CF$_3$ | 289 | CO$_2$Me | H | H |
Compounds 290-319
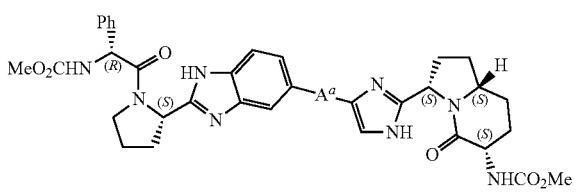
| Entry | A$^a$ |
|---|---|
| 293 | (2,6-naphthyl) |
-continued
Compounds 290-319
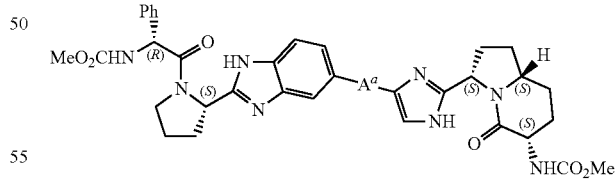
| Entry | A$^a$ |
|---|---|
| 294 | (quinolinyl) |
295

309 -continued

Compounds 290-319

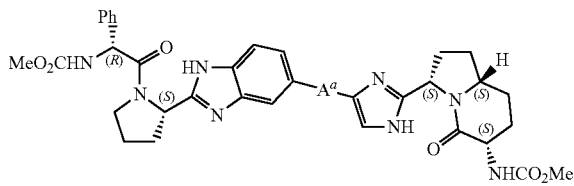

| Entry | $A^a$ |
|---|---|
| 296 | |
| 298 | ![1,4-phenylene] |
| 299 | ![azetidine-pyridine linker] |
| 300 | ![piperazine-pyrimidine linker] |
| 301 | ![pyrazole-pyridine linker] |
| 302 | ![biphenyl] |
| 303 | ![thiophene-phenyl] |
| 304 | ![isoindoline urea linker] |
| 305 | |
| 308 | ![trans-1,4-phenylene] |
| 315 | ![2,5-pyridine] |
| 316 | ![isoindole] |

310 -continued

Compounds 290-319

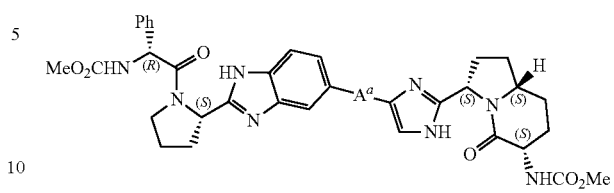

| Entry | $A^a$ |
|---|---|
| 319 | ![piperazine-oxazole linker] |

Compounds 320-343

[structure: MeO₂CHN(R)-Ph-C(O)-(S)-cyclopentyl-benzimidazole-$A^a$-benzimidazole-(S,S,S) bicyclic-NHCO₂Me]

| Entry | $A^a$ |
|---|---|
| 320 | ![1,3-phenylene] |
| 321 | ![1,4-phenylene] |
| 322 | ![2,5-pyridine] |
| 323 | ![2,5-thiophene] |
| 324 | ![pyrazine] |
| 325 | ![pyrimidine] |
| 326 | ![thiazole] |

311
-continued
Compounds 320-343
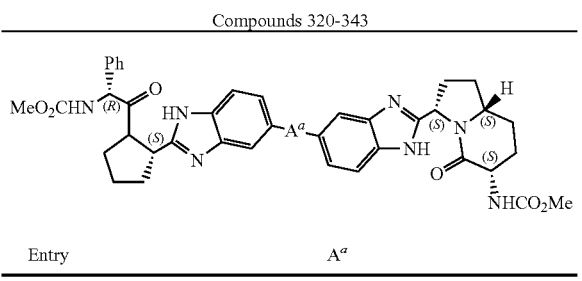
| Entry | $A^a$ |
|---|---|
| 327 | 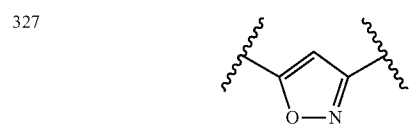 |
| 328 | 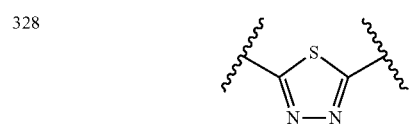 |
| 329 | 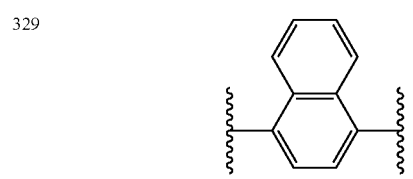 |
| 330 | 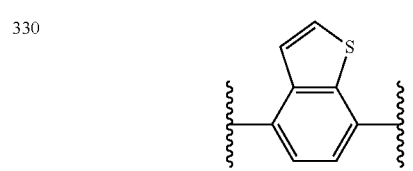 |
| 331 | 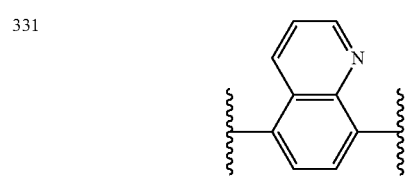 |
| 332 | 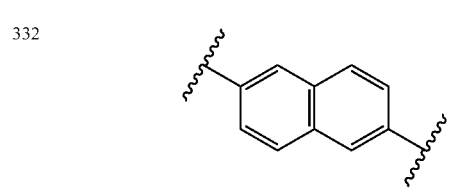 |
| 333 | 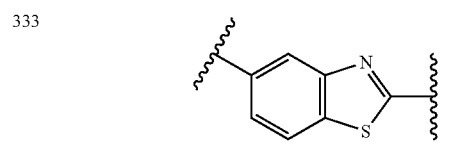 |
| 334 | 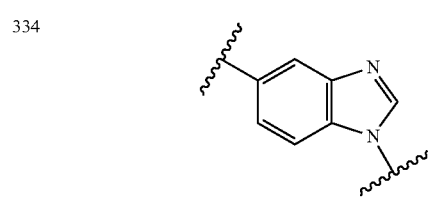 |
312
-continued
Compounds 320-343
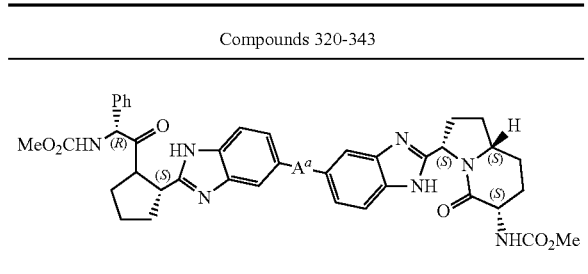
| Entry | $A^a$ |
|---|---|
| 336 | 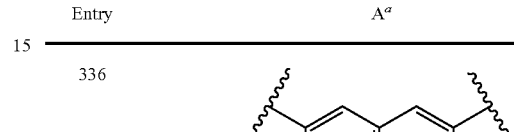 |
| 337 |  |
| 338 | 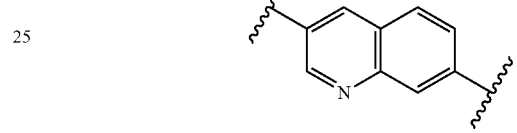 |
| 339 | 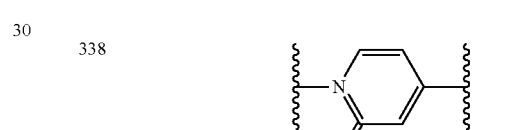 |
| 340 |  |
| 341 |  |
| 343 | 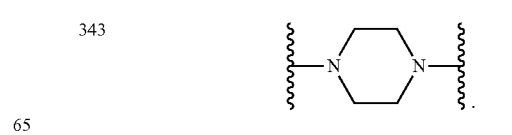 |

7. A compound selected from the group of compounds 368-376 shown below, or a pharmaceutically acceptable salt thereof:
| Compounds 368-376 |
|---|
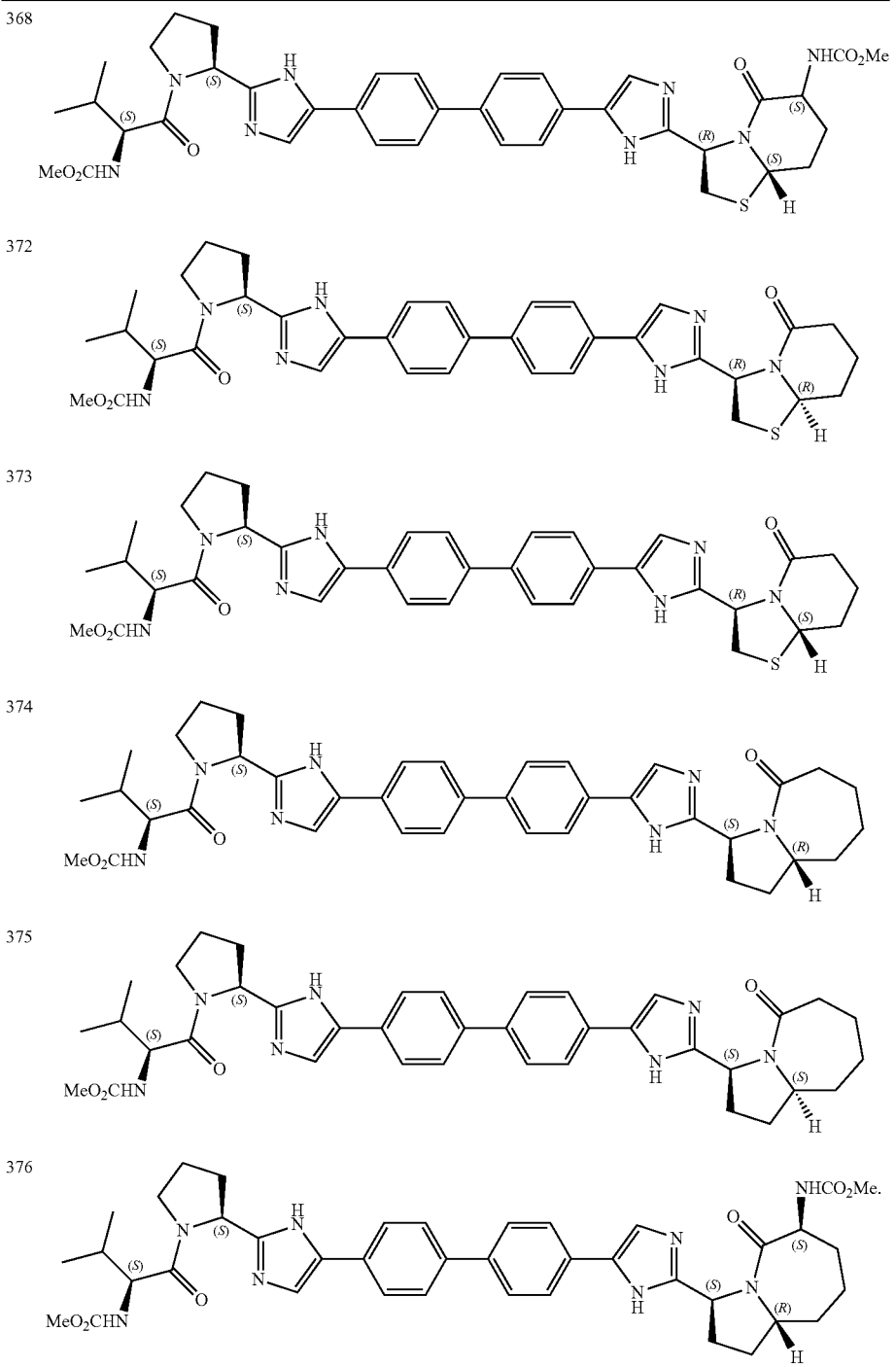
8. A pharmaceutical composition comprising a compound or a combination of compounds according to claim 1, or a pharmaceutically acceptable salt thereof, in combination with a pharmaceutically acceptable carrier or excipient.
* * * * *